(12) United States Patent
Yaver et al.

(10) Patent No.: US 8,940,502 B2
(45) Date of Patent: Jan. 27, 2015

(54) NUCLEIC ACID CONSTRUCTS AND METHODS OF MAKING PROTEIN

(75) Inventors: Debbie Yaver, Davis, CA (US); Mads Eskelund Bjornvad, Virum (DK); Barbara Cherry, Davis, CA (US)

(73) Assignees: Novozymes, Inc., Davis, CA (US); Novozymes A/S, Bagsvaerd (DK)

(*) Notice: Subject to any disclaimer, the term of this patent is extended or adjusted under 35 U.S.C. 154(b) by 266 days.

(21) Appl. No.: 12/373,715

(22) PCT Filed: Jul. 13, 2007

(86) PCT No.: PCT/US2007/073486
§ 371 (c)(1),
(2), (4) Date: Mar. 10, 2009

(87) PCT Pub. No.: WO2008/008967
PCT Pub. Date: Jan. 17, 2008

(65) Prior Publication Data
US 2009/0317866 A1 Dec. 24, 2009

Related U.S. Application Data

(60) Provisional application No. 60/831,151, filed on Jul. 14, 2006.

(51) Int. Cl.
| | | |
|---|---|---|
| C12P 21/06 | (2006.01) |
| C12N 15/00 | (2006.01) |
| C12N 1/00 | (2006.01) |
| C12N 15/09 | (2006.01) |
| C07H 21/04 | (2006.01) |
| C12N 15/81 | (2006.01) |
| C07K 14/395 | (2006.01) |

(52) U.S. Cl.
CPC ............ *C12N 15/81* (2013.01); *C07K 14/395* (2013.01)
USPC .................. 435/69.1; 435/320.1; 435/254.11; 435/69.3; 435/69.4; 536/23.1; 536/24.1

(58) Field of Classification Search
USPC ............. 435/69.1, 320.1, 254.11, 69.3, 69.4; 536/23.1, 24.1
See application file for complete search history.

(56) References Cited

U.S. PATENT DOCUMENTS

| | | | | |
|---|---|---|---|---|
| 5,922,569 A | * | 7/1999 | Heim et al. | 435/69.2 |
| 6,004,779 A | * | 12/1999 | Bradley et al. | 435/69.1 |
| 6,472,171 B1 | * | 10/2002 | Toman et al. | 435/69.1 |

FOREIGN PATENT DOCUMENTS

| | | |
|---|---|---|
| EP | 603128 | 12/1992 |
| EP | 1031628 A1 | 8/1993 |
| EP | 0662514 A1 | 12/1994 |

OTHER PUBLICATIONS

Bermingham-McDonogh et al., The coper, zinc-superoxide dismutase gene of *Saccharomyces cerevisiae:* Cloning, sequencing, and biological activity. PNAS., 1988, vol. 85: 4789-4793.*

Butt et al., Copper metallothionein of yeast, structure of the gene, and regulation of expression. PNAS., 1984, vol. 81: 3332-3336.*

Thiele et al., Tandemly Duplicated Upstream Control Sequences Mediate Copper-Induced Transcription of the *Saccarmonyces cerevisiae* Copper-Metallothionein Gene, 1986, Mol. Cell. Biol. 6: 1158-1163.

Zhou et al., Copper and Gene Regulation in Yeast,1993, Biofactors 4: 105-115.

Thiele et al., ACE1 regulates expression of the *Saccharomyces cerevisiae* metallothionein gene., Mol. Cell. Biol. 1988 8: 2745-2752.

Thiele et al., Tandemly duplicated upstream control sequences mediate copper-induced transcription of the *Saccharomyces cerevisiae* copper-metallothionein gene. Mol. Cell. Biol. 1986 6: 1158-1163.

Mehra et al., *Candida glabrata* metallothioneins. Cloning and sequence of the genes and characterization of proteins, J. Biol. Chem. 1989 264: 19747-19753.

Thorvaldsen et al., Regulation of metallothionein genes by the ACE1 and AMT1 transcription factors, J. Biol. Chem. 1993 268: 12512-12518.

Zhou et al., Isolation of a metal-activated transcription factor gene from *Candida glabrata* by complementation in *Saccharomyces cerevisiae*, PNAS 1991 88:6112-6116.

Gralla et al., 1991, ACE1, a copper-dependent transcription factor, activates expression of the yeast copper, zinc superoxide dismutase gene, PNAS USA 88: 8558-8562.

Macreadie et al., Versatile Cassettes Designed for the Copper Inducible Expression of Proteins in Yeast, 1989, Plasmid 21: 147-150.

(Continued)

*Primary Examiner* — Ganapathirama Raghu
(74) *Attorney, Agent, or Firm* — Robert L. Starnes

(57) ABSTRACT

The present invention relates to methods for producing a polypeptide, comprising: (a) cultivating a fungal host cell in a medium conducive for the production of the polypeptide, wherein the fungal host cell comprises a first polynucleotide comprising a nucleic acid sequence encoding the polypeptide operably linked to a copper-inducible promoter sequence comprising a copper-responsive upstream activation sequence activated by a copper-dependent trans-acting transcription factor and a second polynucleotide comprising one or more (several) additional copper-responsive upstream activation sequences operably linked upstream to the promoter sequence, wherein the promoter sequence is foreign to the nucleic acid sequence encoding the polypeptide and the copper-responsive upstream activation sequences are responsible for copper-induced transcription of the promoter sequence, and a third polynucleotide comprising at least one copy of a gene encoding the copper-dependent trans-acting transcription factor; and (b) isolating the polypeptide from the cultivation medium.

19 Claims, 15 Drawing Sheets

(56) References Cited

OTHER PUBLICATIONS

Hottiger et al., Physiological characterization of the yeast metallothionein (*CUP1*) promoter, and consequences of overexpressing its transcriptional activator, *ACE1*, 1994, *Yeasr* 10: 283-296.

Ward et al., Vectors for $Cu^{2+}$-inducible Production of Glutathione S-Transferase-Fusion Proteins for Single-step Purification from Yeast, 1994, Yeast 10: 441-449.

Macreadie et al., Improved shuttle vectors for cloning and high-level $Cu^{2+}$-mediated expression of foreign genes in yeast, 1991, Gene 104: 107-111.

Furst et al., Copper Activates Metallothionein Gene Transcription by Altering the Conformation of a Specific DNA Binding Protein, 1988, *Cell* 55: 705-717.

Mascorro-Gallardo et al., Construction of a *CUP1* promoter-based vector to modulate gene expression in *Saccharomyces cerevisiae*, 1996, *Gene* 172: 169-170.

\* cited by examiner

NUCLEIC ACID CONSTRUCTS AND METHODS OF MAKING PROTEIN

CROSS-REFERENCE TO RELATED APPLICATIONS

This application is a 35 U.S.C. 371 national application of PCT/US07/73486 filed on Jul. 13, 2007 and claims priority from U.S. provisional application Ser. No. 60/831,151 filed on Jul. 14, 2006, which applications are fully incorporated herein by reference.

BACKGROUND OF THE INVENTION

1. Field of the Invention

The present invention relates to methods for increasing expression of genes encoding polypeptides in a fungal cell.

2. Description of the Related Art

The recombinant production of a native or foreign polypeptide in a fungal host cell. e.g., a yeast or filamentous fungal cell, may provide for a more desirable vehicle for producing the polypeptide in commercially relevant quantities.

Recombinant production of a native or foreign polypeptide is generally accomplished by constructing an expression cassette in which the DNA coding for the polypeptide is placed under the expression control of a promoter from a regulated gene. The expression cassette is introduced into the host cell, usually by plasmid-mediated transformation. Production of the polypeptide is then achieved by culturing the transformed host cell under inducing conditions necessary for the proper functioning of the promoter contained on the expression cassette.

The development of new expression constructs and vectors for the recombinant production of polypeptides in a fungal host cell generally requires the availability of efficient promoters that are suitable for controlling expression of the polypeptides in the host cell. However, even the best known promoters can be inefficient for expressing a gene of interest.

Many promoters are susceptible to being modulated which can increase their efficiency. The *Saccharomyces cerevisiae* metallothionein gene, designated CUP1, is transcriptionally activated by copper through a specific promoter region, UAS-$_{CUP1}$ (upstream activation sequence), reportedly located between −105 and −230 with respect to the CUP1 transcription activation site (Thiele and Hamer, 1986, *Mol. Cell. Biol.* 6: 1158-1163; Zhou and Thiele, 1993, *Biofactors* 4: 105-115). The Ace1 protein (Ace1p) of *Saccharomyces cerevisiae* is responsible for induction of the yeast metallothionein gene CUP1, in the presence of copper ions (Thiele, 1988, *Mol. Cell. Biol.* 8: 2745-2752) or silver ions (Furst et al., 1988, *Cell* 55: 705-717). The amino-terminal half of the Ace1p is rich in basic amino acid residues and cysteines and specifically binds to the CUP1 upstream activator sequence in the presence, but not in the absence, of Cu(I) or Ag(I) (Furst et al., 1988, supra). Thiele and Hamer, 1986, *Molecular and Cellular Biology* 6: 1158-1163, disclose that tandemly duplicated upstream control sequences mediate copper-induced transcription of the *Saccharomyces cerevisiae* copper-metallothionein gene and a synthetic version of one of these elements confers copper induction on a heterologous promoter when present in two tandem copies.

Gralla et al., 1991, *PNAS USA* 88: 8558-8562, disclose that Ace1p activates expression of a yeast copper, zinc superoxide dismutase gene. Lapinskas et al., 1993, *Current Genetics* 24: 388-393, disclose that Ace1p activates expression of a *Saccharomyces cerevisiae* cytosolic catalase gene.

Mehra et al., 1989, *J. Biological Chemistry* 264: 19747-19753, describe the cloning and sequences of metallothionein genes from *Candida glabrata*. Zhou and Thiele, 1991, *PNAS USA* 88: 6112-6116, describe the isolation of a metal-activated transcription factor gene from *Candida glabrata*. Thorvaldsen et al., 1993, *J. Biological Chemistry* 268: 12512-12518, disclose the regulation of the *Candida glabrata* metallothionein genes, designated MTI, MTIIa, and MTIIb, by AMT1.

Mascorro-Gallardo et al., 1996, *Gene* 172: 169-170, disclose construction of a CUP1 promoter-based vector to modulate gene expression in *Saccharomyces cerevisiae*. Macreadie et al., 1989, *Plasmid* 21: 147-150, disclose a series of yeast expression vectors utilizing the CUP1 gene of *Saccharomyces cerevisiae*. Hottiger et al., 1994, *Yeast* 10: 283-296, disclose the physiological characterization of the CUP1 promoter and consequences of overexpressing its transcriptional activator Ace1p.

It is an object of the present invention to provide improved methods for producing a polypeptide in a fungal host cell.

SUMMARY OF THE INVENTION

The present invention relates to methods for producing a polypeptide, comprising: (a) cultivating a fungal host cell in a medium conducive for the production of the polypeptide, wherein the fungal host cell comprises a first polynucleotide comprising a nucleic acid sequence encoding the polypeptide operably linked to a copper-inducible promoter sequence comprising a copper-responsive upstream activation sequence activated by a copper-dependent trans-acting transcription factor and a second polynucleotide comprising one or more (several) additional copper-responsive upstream activation sequences operably linked upstream to the promoter sequence, wherein the promoter sequence is foreign to the nucleic acid sequence encoding the polypeptide and the copper-responsive upstream activation sequences are responsible for copper-induced transcription of the promoter sequence, and a third polynucleotide comprising at least one copy of a gene encoding the copper-dependent trans-acting transcription factor; and (b) isolating the polypeptide from the cultivation medium. The polypeptide may be native or foreign to the fungal host cell.

The present invention also relates to fungal host cells comprising a first polynucleotide comprising a nucleic acid sequence encoding a polypeptide operably linked to a copper-inducible promoter sequence comprising a copper-responsive upstream activation sequence activated by a copper-dependent trans-acting transcription factor and a second polynucleotide comprising one or more (several) additional copper-responsive upstream activation sequences operably linked upstream to the promoter sequence, wherein the promoter sequence is foreign to the nucleic acid sequence encoding the polypeptide and the copper-responsive upstream activation sequences are responsible for copper-induced transcription of the promoter sequence, and a third polynucleotide comprising at least one copy of a gene encoding the copper-dependent trans-acting transcription factor.

The present invention further relates to nucleic acid constructs and vectors comprising a first polynucleotide comprising a nucleic acid sequence encoding a polypeptide operably linked to a copper-inducible promoter sequence comprising a copper-responsive upstream activation sequence activated by a copper-dependent trans-acting transcription factor and a second polynucleotide comprising one or more (several) additional copper-responsive upstream activation sequences operably linked upstream to the promoter sequence, wherein the promoter sequence is foreign to the nucleic acid sequence encoding the polypeptide and the copper-responsive upstream activation sequences are responsible for copper-induced transcription of the promoter sequence.

BRIEF DESCRIPTION OF THE FIGURES

FIG. 1 shows a restriction map of pBM128a.
FIG. 3 shows a restriction map of pBM126a.
FIG. 10 shows a restriction map of pBM163a.
FIG. 11 shows a restriction map of pBM165a.
FIG. 12 shows a restriction map of pBM168a.
FIG. 13 shows a restriction map of pBM169a.
FIG. 14 shows a restriction map of pBM171a.
FIG. 15 shows a restriction map of pBM170a.

DETAILED DESCRIPTION OF THE INVENTION

Figure 1:
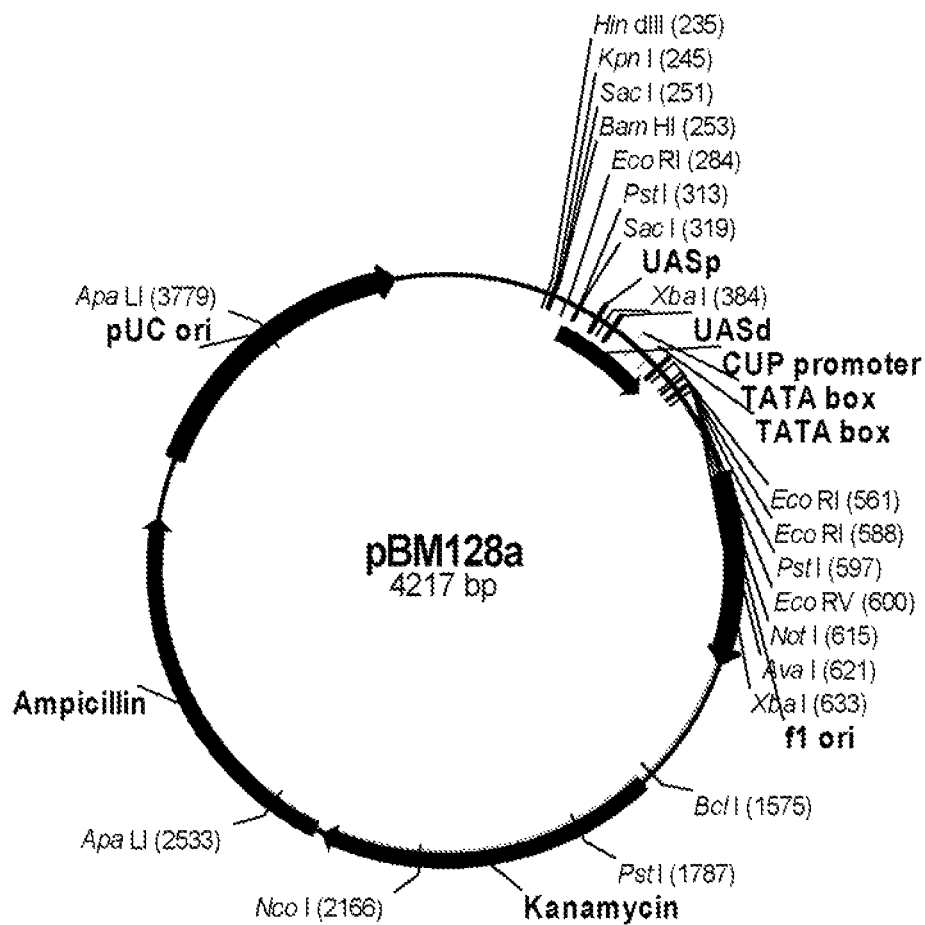

The present invention relates to methods for producing a polypeptide, comprising (a) cultivating a fungal host cell in a medium conducive for the production of the polypeptide, wherein the fungal host cell comprises a first polynucleotide comprising a nucleic acid sequence encoding the polypeptide operably linked to a copper-inducible promoter sequence comprising a copper-responsive upstream activation sequence activated by a copper-dependent trans-acting transcription factor and a second polynucleotide comprising one or more (several) additional copper-responsive upstream activation sequences operably linked upstream to the promoter sequence, wherein the promoter sequence is foreign to the nucleic acid sequence encoding the polypeptide and the copper-responsive upstream activation sequences are responsible for copper-induced transcription of the promoter sequence, and a third polynucleotide comprising at least one copy of a gene encoding the copper-dependent trans-acting transcription factor; and (b) isolating the polypeptide from the cultivation medium.

In the production methods of the present invention, the fungal host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors. The cultivation takes place in a suitable nutrient medium comprising carbon, nitrogen sources, inorganic salts, and copper ions (and/or silver ions), using procedures known in the art. Suitable media are available from commercial suppliers or may be prepared according to published compositions (e.g., in catalogues of the American Type Culture Collection). When copper ions are present in the medium, the medium contains at least 10 µM copper eons, preferably at least 50 µM copper ions, more preferably at least 100 µM copper ions, even more preferably at least 250 µM, and most preferably at least 500 µM copper ions. The copper ions can be added to the medium in the form of $CuSO_4$, $CuCl_2$, or any other suitable form. The medium can also or alternatively contain silver ions. When silver is present in the medium, the medium contains at least 10 µM silver ions, preferably at least 50 µM silver ions, more preferably at least 100 µM silver ions, even more preferably at least 250 µM silver ions, and most preferably at least 500 µM silver ions. The silver ions can be added to the medium in the form of $Ag_2SO_4$, AgCl, or any other suitable form.

The polypeptide may be detected using methods known in the art that are specific for the polypeptide. These detection methods may include use of specific antibodies, high performance liquid chromatography, capillary chromatography, formation of an enzyme product, disappearance of an enzyme substrate, or SDS-PAGE. For example, where the polypeptide is an enzyme, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990).

If the polypeptide is secreted into the nutrient medium, the substance can be recovered directly from the medium. If the polypeptide is not secreted, it can be recovered from cell lysates. The resulting polypeptide may be isolated using methods known in the art. For example, the polypeptide may be isolated from the cultivation medium by conventional procedures including, but not limited to, centrifugation, filtration, extraction, spray-drying, evaporation, and/or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989).

A fungal host cell of the present invention comprising a first polynucleotide comprising a nucleic acid sequence encoding the polypeptide operably linked to a copper-inducible promoter sequence comprising a copper-responsive upstream activation sequence activated by a copper-dependent trans-acting transcription factor and a second polynucleotide comprising one or more (several) additional copper-responsive upstream activation sequences operably linked upstream to the promoter sequence, wherein the promoter sequence is foreign to the nucleic acid sequence encoding the polypeptide and the copper-responsive upstream activation sequences are responsible for copper-induced transcription of the promoter sequence, and a third polynucleotide comprising at least one copy of a gene encoding the copper-dependent trans-acting transcription factor, produces at least 10%, preferably at least 25%, more preferably at least 50%, even more preferably at least 75%, most preferably at least 100%, and even most preferably at least 200% more polypeptide than a fungal host cell without a second polynucleotide comprising one or more (several) additional copper-responsive upstream activation sequences operably linked upstream to the promoter sequence, and/or a third polynucleotide comprising at least one copy of a gene encoding the copper-dependent trans-acting transcription factor.

Promoters

The term "promoter" is defined herein as a DNA sequence that binds RNA polymerase and directs the polymerase to the correct downstream transcriptional start site of a polynucleotide comprising a nucleic acid sequence encoding a polypeptide to initiate transcription, RNA polymerase effectively catalyzes the assembly of messenger RNA complementary to the appropriate DNA strand of the coding region. The term "promoter" will also be understood to include the 5' non-coding region (between promoter and translation start) for translation after transcription into mRNA, cis-acting transcription control elements such as transcriptional activators, and other nucleotide sequences capable of interacting with transcription factors.

The term "copper-inducible promoter sequence" is defined herein as a promoter that is induced by copper ions via a cis-acting element as a component of the promoter, which possesses binding sites for transcriptional regulatory factors that are responsible for copper-induced transcription of the promoter.

The term "tandem promoter" is defined herein as two or more promoter sequences each of which is operably linked to a coding sequence and mediates transcription of the coding sequence into mRNA. The components of the tandem promoter may be the same promoter or a combination of different promoters. The promoters can be obtained from genes encoding extracellular or intracellular polypeptides either native or foreign to the host cell. At least one of the promoters contained in the tandem promoter is a copper-inducible promoter. In a preferred aspect, the tandem promoter is composed of copper-inducible promoters.

The term "hybrid promoter" is defined herein as a promoter sequence that is composed of portions of two or more promoters operably linked to a coding sequence and mediates transcription of the coding sequence into mRNA. The promoters can be obtained from genes encoding extracellular or intracellular polypeptides either native or foreign to the host cell. At least one portion of the hybrid promoter is a portion of a copper-inducible promoter. In a preferred aspect, the hybrid promoter is composed of portions of two or more copper-inducible promoters.

The term "operably linked" is defined herein as a configuration in which a control sequence, e.g., a promoter sequence, is appropriately placed at a position relative to a coding sequence such that the control sequence directs the production of a polypeptide encoded by the coding sequence.

The term "coding sequence" is defined herein as a nucleic acid sequence that is transcribed into mRNA which is translated into a polypeptide, e.g., enzyme, when placed under the control of the appropriate control sequences. The boundaries of the coding sequence are generally determined by an open reading frame, which usually begins with the ATG start codon or alternative start codons such as GTG and TTG, and ends with a stop codon such as TAA, TAG and TGA. A coding sequence can include, but is not limited to, genomic DNA, cDNA, semisynthetic, synthetic, and recombinant nucleic acid sequences.

In practicing the methods of the present invention, a copper-inducible promoter can be obtained from a *Saccharomyces cerevisiae* metallothienein gene, *Saccharomyces cerevisiae* superoxide dismutase gene, *Saccharomyces cerevisiae* cytosolic catalase gene, *Saccharomyces cerevisiae* copper resistant suppressor gene, *Candida glabrata* metallothionein gene, *Neurospora crassa* metallothionein gene, *Yarrowia lipolytica* metallothionein gene, *Agaricus bisporus* metallothionein gene, *Magnaporthe grisea* metallothionein gene, and *Podospora anserina* metallothionein gene.

In a preferred aspect, the copper-inducible promoter sequence is obtained from a *Saccharomyces cerevisiae* metallothionein gene. In a more preferred aspect, the copper-inducible promoter sequence is obtained from a *Saccharomyces cerevisiae* CUP1 gene (Accession number P07215) (Butt et al. 1984, *PNAS USA* 76: 3332-3336) (SEQ ID NO: 1 for DNA and SEQ ID NO: 2 for the deduced amino acid sequence).

In another preferred aspect, the copper-inducible promoter sequence is obtained from a *Saccharomyces cerevisiae* superoxide dismutase gene. In a more preferred aspect, the copper-inducible promoter sequence is obtained from a *Saccharomyces cerevisiae* SOD1 gene (Accession number P00445) (Gralla et al., 1991, *PNAS USA* 88: 8558-8562) (SEQ ID NO: 3 for DNA and SEQ ID NO: 4 for the deduced amino acid sequence).

In another preferred aspect, the copper-inducible promoter sequence is obtained from a *Saccharomyces cerevisiae* cytosolic catalase gene. In a more preferred aspect, the copper-inducible promoter sequence is obtained from a *Saccharomyces cerevisiae* CTT1 gene (Accession number P06115) (Lapinskas et al., 1993, *Current Genetics* 24: 388-393) (SEQ ID NO: 5 for DNA and SEQ ID NO: 6 for the deduced amino acid sequence).

In another preferred aspect, the copper-inducible promoter sequence is obtained from a *Saccharomyces cerevisiae* copper resistant suppressor gene. In a more preferred aspect, the copper-inducible promoter sequence is obtained from a *Saccharomyces cerevisiae* CRS5 gene (Accession number P41902) (Culotta et al., 1994, *J. Biol. Chem.* 269: 25295-252302) (SEQ ID NO: 7 for DNA and SEQ ID NO: 8 for the deduced amino acid sequence).

In another preferred aspect, the copper-inducible promoter sequence is obtained from a *Candida glabrata* metallothionein gene. In a more preferred aspect, the copper-inducible promoter sequence is obtained from a *Candida glabrata* MT gene. In a most preferred aspect, the copper-inducible promoter sequence is obtained from a *Candida glabrata* MTI gene (Accession number P15113) (Mehra et al., 1989, *J. Biological Chemistry* 264: 19747-19753; Mehra et al., 1992, *Gene* 114: 75-80; Mehra et al., 1990, *Gene* 265: 6369-6375) (SEQ ID NO: 9 for DNA and SEQ ID NO: 10 for the deduced amino acid sequence). In another most preferred aspect, the copper-inducible promoter sequence is obtained from a *Candida glabrata* MTII gene (Accession number J05398) (Mehra et al., 1989, supra; Mehra et al., 1992, supra; Mehra et al., 1990, supra) (SEQ ID NO: 11 for DNA and SEQ ID NO: 12 for the deduced amino acid sequence).

In the methods of the present invention, the copper-inducible promoter may also be a tandem promoter comprising two or more promoters or a hybrid promoter comprising portions of two or more promoters, at least one of which is a copper-inducible promoter or a portion of a copper-inducible promoter.

Examples of promoters that are not copper-inducible promoters but useful in the construction of tandem or hybrid promoters with the copper-inducible promoter(s) include, but are not limited to, the promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase, *Fusarium venenatum* Daria promote, *Fusarium venenatum* Quinn promoter, *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Sac-* charomyces cerevisiae 3-phosphoglycerate kinase; as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof. Other useful promoters for yeast host cells are described by Romanos et al., 1992, *Yeast* 8: 423-488.

In the methods of the present invention, the hybrid or tandem promoter will be understood to be foreign to a nucleic acid sequence encoding a polypeptide, even if a wild-type promoter or a portion thereof as a component of the tandem or hybrid promoter is native to the nucleic acid sequence. For example, in a tandem promoter consisting of at least two promoters, one or more (several) of the promoters may be a wild-type promoter of the nucleic acid sequence encoding a polypeptide.

Upstream Activation Sequences (UAS)

The term "copper-responsive upstream activation sequence" is defined herein as a region of a promoter comprising a DNA sequence, designated a cis-acting element, which serves as a binding site for transcriptional regulatory factors which are responsible for copper-induced transcription of a promoter. For yeast and filamentous fungal genes, a promoter region containing such a cis-acting element is referred to as an upstream activation sequence, which is abbreviated UAS. (Thiele, 1992, *Nucleic Acids Research* 20: 1183-1191). Identification and isolation of such a UAS can be accomplished according to the procedures described by Thiele and Hamer, 1986, supra; Zhou and Thiele, 1993, supra; and Thiele, 1992, supra.

In the methods of the present invention, any cis-acting promoter element responsible for copper-induced gene transcription can be used. The copper-responsive upstream activation sequence can be obtained from a copper-inducible promoter of a gene selected from the group consisting of a *Saccharomyces cerevisiae* metallothienein gene, *Saccharomyces cerevisiae* superoxide dismutase gene, *Saccharomyces cerevisiae* cytosolic catalase gene, *Saccharomyces cerevisiae* copper resistant suppressor gene, *Candida glabrata* metallothionein gene, *Neurospora crassa* metallothionein gene, *Yarrowia lipolytica* metallothionein gene, *Agaricus bisporus* metallothionein gene. *Magnaporthe grisea* metallothionein gene, and *Podospora anserina* metallothionein gene.

In a preferred aspect, the copper-responsive upstream activation sequence is obtained from the promoter of a *Saccharomyces cerevisiae* metallothionein gene. In a more preferred aspect, the copper-responsive upstream activation sequence is obtained from the promoter of a *Saccharomyces cerevisiae* CUP1 gene (Accession number P07215) (Butt et al., 1984, supra).

In another preferred aspect, the copper-responsive upstream activation sequence is obtained from the promoter of a *Saccharomyces cerevisiae* cytosolic catalase gene. In a more preferred aspect, the copper-responsive upstream activation sequence is obtained from the promoter of a *Saccharomyces cerevisiae* CTT1 gene (Accession number P06115) (Lapinskas et al., 1993, supra).

In another preferred aspect, the copper-responsive upstream activation sequence is obtained from a *Saccharomyces cerevisiae* superoxide dismutase gene. In a more preferred aspect, the copper-responsive upstream activation sequence is obtained from the promoter of a *Saccharomyces cerevisiae* SOD1 gene (Accession number P00445) (Gralla et al., 1991, supra).

In another preferred aspect, the copper-responsive upstream activation sequence is obtained from a *Saccharomyces cerevisiae* copper resistant suppressor gene. In a more preferred aspect, the copper-responsive upstream activation sequence is obtained from the promoter of a *Saccharomyces cerevisiae* CRS5 gene (Accession number P41902) (Culotta et al., 1994, supra).

In another preferred aspect, the copper-responsive upstream activation sequence is obtained from a *Candida glabrata* metallothionein gene. In a more preferred aspect, the copper-responsive upstream activation sequence is obtained from a *Candida glabrata* MT gene. In a most preferred aspect, the copper-responsive upstream activation sequence is obtained from a *Candida glabrata* MTI gene (Accession number P15113) (Mehra et al., 1989, supra; Mehra et al., 1992, supra; Mehra et al., 1990, supra). In another most preferred aspect, the copper-responsive upstream activation sequence is obtained from a *Candida glabrata* MTIIa gene (Accession number P15113) (Mehra et al., 1989, supra; Mehra et al., 1992, supra; Mehra et al., 1990, supra). In another most preferred aspect, the copper-responsive upstream activation sequence is obtained from a *Candida glabrata* MTIIb gene (Accession number P15114; SEQ ID NO: 48) (Mehra et al., 1989, supra; Mehra et al., 1992, supra; Mehra et al., 1990, supra).

In the methods of the present invention, one or more (several) additional copper-responsive upstream activation sequences (UASs) are operably linked upstream to the copper-inducible promoter. It is understood that the copper-inducible promoter will contain its own copper-responsive upstream activation sequencers), and, consequently, the one or more (several) additional copper-responsive upstream activation sequences operably linked upstream to the promoter can be the same UAS region as that contained in the promoter, can be a different UAS region from that contained in the promoter, or can be a combination thereof. Depending on the number of copper-responsive elements associated with the upstream activation sequence. i.e., the correlation of the number of copper-responsive elements and the copper-dependent transcriptional potency, more than one upstream activation sequence may be placed upstream of the promoter. Consequently, depending on the number of copper-responsive cis-acting elements contained in an upstream activation sequence, multiple copies of a specific upstream activation sequence can be used, combinations of different upstream activation sequences can be used, or a combination of each of the preceding can be used. The total number of copper-responsive cis-acting elements is at least 2, preferably at least 3, more preferably at least 4, even more preferably at least 5, and most preferably at least 6.

In a preferred aspect, one of the additional copper-responsive upstream activation sequences is SEQ ID NO: 46. In another preferred aspect, one of the additional copper-responsive upstream activation sequences is SEQ ID NO: 47.

Transcriptional Activator Genes

The term "copper-dependent trans-acting transcription factor gene" is defined herein as a gene which encodes a transcription factor that activates gene transcription via a copper-responsive upstream activation sequence (UAS) coupled to a copper-inducible promoter sequence in a copper-dependent manner. Such genes are also called copper metallo-regulatory transcription factor (MRTF) genes. It will be understood that encompassed within the term "copper-dependent trans-acting transcription factor gene", as used herein, are truncated and/or mutated versions of such a gene.

In the methods of the present invention, any transcriptional activator gene which encodes a transcription factor that activates gene transcription via a copper-responsive upstream activation sequence (UAS) can be used. The transcriptional activator gene can be selected from the group consisting of a

*Saccharomyces cerevisiae* ACE1 gene, *Candida glabrata* AMT1 gene, *Yarrowia lipolytica* CRF1 gene (Accession number P45815), *Schizosaccharomyces pombe* CUF2 gene (Accession number O094588), *Saccharomyces cerevisiae* HAA1 gene (Accession Number Q12753), and *Aspergillus fumigatus* copper fist DNA binding domain protein gene (Accession number Q4WN33).

In a preferred aspect, the transcriptional activator gene is a *Saccharomyces cerevisiae* ACE1 gene (Accession number P15315) (Thiele and Hamer, 1986, *Mol. Cell. Biol.* 6: 1158-1163) (SEQ ID NO: 13 for DNA and SEQ ID NO: 14 for the deduced amino acid sequence).

In another preferred aspect, the transcriptional activator gene is a *Candida glabrata* AMT1 gene (Accession number P41772) (Zhou and Thiele, 1991, *PNAS USA* 88: 6112-6116) (SEQ ID NO: 15 for DNA and SEQ ID NO: 16 for the deduced amino acid sequence).

In another preferred aspect, the transcriptional activator gene is a *Yarrowia lipolytica* CRF1 gene (Accession number P45815) (SEQ ID NO: 17 for DNA and SEQ ID NO: 18 for the deduced amino acid sequence).

In another preferred aspect, the transcriptional activator gene is a *Schizosaccharomyces pombe* CUF2 gene (Accession number O94588) (SEQ ID NO: 19 for DNA and SEQ ID NO: 20 for the deduced amino acid sequence).

In another preferred aspect, the transcriptional activator gene is a *Saccharomyces cerevisiae* HAA1 gene (Accession Number Q12753) (SEQ ID NO: 21 for DNA and SEQ ID NO: 22 for the deduced amino acid sequence).

In another preferred aspect, the transcriptional activator gene is an *Aspergillus fumigatus* copper fist DNA binding domain protein gene (Accession number Q4WN33) (SEQ ID NO: 23 for DNA and SEQ ID NO: 24 for the deduced amino acid sequence).

In the methods of the present invention, the fungal host cell comprises at least one transcriptional activator gene. The transcriptional activator gene can be native or foreign to the host cell. In a preferred aspect, multiple copies of a transcriptional activator gene are present in the host. Alternatively, a combination of at least two different transcriptional activator genes each present in one or more (several) copies may be present in the fungal host cell. The genes may be native or foreign to the host cell, or a combination thereof.

An increase in the copy number of a transcriptional activator gene can be obtained by integrating at least one additional copy of the gene into the host cell genome or by including an amplifiable selectable marker gene with the transcriptional activator gene where cells containing amplified copies of the selectable marker gene, and thereby additional copies of the transcriptional activator gene, can be selected for by cultivating the cells in the presence of the appropriate selectable agent.

The transcriptional activator gene(s) may be integrated into the chromosome of the host cell or may be present as extrachromosomal elements, or a combination thereof. In a preferred aspect, the transcriptional activator gene(s) is integrated into the chromosome of the host cell.

Polypeptides

The polypeptide may be native or heterologous to the fungal host cell of interest. The term "heterologous polypeptide" is defined herein as a polypeptide which is not native to the host cell, or a native polypeptide in which structural modifications have been made to alter the native polypeptide.

The polypeptide may be any polypeptide having a biological activity of interest. The term "polypeptide" is not meant herein to refer to a specific length of the encoded product and, therefore, encompasses peptides, oligopeptides, and proteins.

The term "polypeptide" also encompasses hybrid polypeptides, which comprise a combination of partial and/or complete polypeptide sequences obtained from at least two different polypeptides wherein one or more (several) may be heterologous to the fungal cell. Polypeptides further include naturally occurring allelic and engineered variations of a polypeptide.

In a preferred aspect, the polypeptide is an antibody, antigen, antimicrobial peptide, enzyme, growth factor, hormone, immunodilator, neurotransmitter, receptor, reporter protein, structural protein, and transcription factor.

In a more preferred aspect, the polypeptide is an oxidoreductase, transferase, hydrolase, lyase, isomerase, or ligase. In a most preferred aspect, the polypeptide is an alpha-glucosidase, aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another preferred aspect, the polypeptide is an albumin, collagen, tropoelastin, elastin, or gelatin.

The nucleic acid sequence encoding a polypeptide may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The techniques used to isolate or clone a nucleic acid sequence encoding a polypeptide are known in the art and include isolation from genomic DNA, preparation from cDNA, or a combination thereof. The cloning of the nucleic acid sequence from such genomic DNA can be effected, e.g., by using the polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleic acid sequence encoding the polypeptide, insertion of the fragment into a vector molecule, and incorporation of the recombinant vector into the fungal cell where multiple copies or clones of the nucleic acid sequence will be replicated. The nucleic acid sequence may be of genomic, cDNA, RNA, semisynthetic, synthetic origin, or any combinations thereof.

Nucleic Acid Constructs

The present invention also relates to nucleic acid constructs comprising a first polynucleotide comprising a nucleic acid sequence encoding a polypeptide of interest operably linked to a copper-Inducible promoter sequence activated by a copper-dependent trans-acting transcription factor and a second polynucleotide comprising at least one copper-responsive upstream activation sequence (UAS) upstream of the promoter, and one or more (several) control sequences which direct the expression of the coding sequence of the polynucleotide in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains a coding sequence and all the control sequences required for expression of the coding sequence.

An isolated polynucleotide encoding a polypeptide or a copper-dependent trans-acting transcription factor can also be manipulated to provide for improved expression of the polypeptide or the transcription factor. Manipulation of the nucleic acid sequence prior to its insertion into a vector may be desirable or necessary depending on the expression vector. The techniques for modifying nucleic acid sequences utilizing recombinant DNA methods are well known in the art.

In the methods of the present inventions the nucleic acid sequence encoding a polypeptide or a copper-dependent trans-acting transcription factor may comprise one or more (several) native control sequences or one or more (several) of the native control sequences may be replaced with one or more (several) control sequences foreign to the nucleic acid sequence for improving expression of the coding sequence in a host cell.

The term "control sequences" is defined herein to include all components which are necessary or advantageous for the expression of a polypeptide. Each control sequence may be native or foreign to the nucleic acid sequence encoding the polypeptide. In addition to the copper-inducible promoter(s) and copper-responsive upstream activation sequence(s) described herein, such control sequences include, but are not limited to, a promoter, leader, polyadenylation sequence, propeptide sequence, signal peptide sequence, and transcription terminator. At a minimum, the control sequences include a copper-inducible promoter(s), copper-responsive upstream activation sequencers), and transcriptional and translational stop signals. The control sequences may be provided with linkers for the purpose of introducing specific restriction sites facilitating ligation of the control sequences with the coding region of the nucleic acid sequence encoding a polypeptide.

Manipulation of the promoter of a polynucleotide encoding a polypeptide of interest has already been discussed herein. For the copper-dependent trans-acting transcription factor, the control sequence may be an appropriate promoter sequence, a nucleotide sequence which is recognized by a host cell for expression of a polynucleotide encoding the transcription factor. The promoter sequence contains transcriptional control sequences which mediate the expression of the transcription factor. The promoter may be any nucleotide sequence which shows transcriptional activity in the host cell of choice including mutant, truncated, and hybrid promoters, and may be obtained from genes encoding extracellular or intracellular polypeptides either native or foreign to the host cell.

Examples of suitable promoters for directing transcription in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA). *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), Fusarium oxysporum trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, Trichoderma reesei xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may be a suitable transcription terminator sequence, a sequence recognized by a host cell to terminate transcription. The terminator sequence is operably linked to the 3' terminus of the nucleic acid sequence encoding the polypeptide. Any terminator which is functional in the fungal host cell of choice may be used in the present invention.

Preferred terminators for filamentous fungal host cells are obtained from the genes for *Aspergillus oryzae* TAKA amylase. *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase, *Aspergillus nidulans* triose phosphate isomerase, *Fusarium venenatum* trypsin, and *Fusarium venenatum* glucoamylase.

Suitable leaders for yeast host cells are obtained from the genes for *Saccharomyces cerevisiae* enolase (ENO1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the fungal host cell of choice may be used in the present invention.

Preferred polyadenylation sequences for filamentous fungal host cells are obtained from the genes for *Aspergillus oryzae* TAKA amylase. *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a fungal host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide or the copper-dependent trans-acting transcription factor relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, *Aspergillus oryzae* glucoamylase promoter, and *Fusarium venenatum* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a first polynucleotide comprising a nucleic acid sequence encoding a polypeptide of interest operably linked to a copper-inducible promoter sequence comprising a copper-responsive upstream activation sequence activated by a copper-dependent trans-acting transcription factor and a second polynucleotide comprising one or more (several) additional copper-responsive upstream activation sequences operably linked upstream to the promoter sequence, wherein the promoter sequence is foreign to the nucleic acid sequence encoding the polypeptide and the copper-responsive upstream activation sequences are responsible for copper-induced transcription of the promoter. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence may be expressed by inserting the first polynucleotide and the second polynucleotide into an appropriate vector for expression. In creating the expression vector, the coding sequence is located in the vector so that the coding sequence is operably linked to a copper-inducible promoter, a copper-responsive upstream activation sequence, and one or more appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g. a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*. Preferred for use in a *Fusarium* cell is the bar, amdS, pyrG, or hygB gene.

The vectors of the present invention preferably contain an element(s) that permits stable integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell. Examples of a plasmid replicator useful in a yeast cell are the 2 micron origin of replication, ARS1, ARS4, the combination of ARS1 and CEN3, and the combination of ARS4 and CEN6. Examples of a plasmid replicator useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence encoding a polypeptide may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Fungal Host Cells

The present invention also relates to recombinant fungal host cells, comprising a first polynucleotide comprising a nucleic acid sequence encoding a polypeptide of interest operably linked to a copper-inducible promoter sequence comprising a copper-responsive upstream activation sequence activated by a copper-dependent trans-acting transcription factor and a second polynucleotide comprising one or more (several) additional copper-responsive upstream activation sequences operably linked upstream to the promoter sequence, wherein the promoter sequence is foreign to the nucleic acid sequence encoding the polypeptide and the copper-responsive upstream activation sequences are responsible for copper-induced transcription of the promoter sequence, and further comprising a third polynucleotide comprising at least one copy of a gene encoding the copper-dependent trans-acting transcription factor. An expression vector or nucleic acid construct, as described herein, is introduced into a host cell so that the vector or construct is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the polynucleotide encoding the polypeptide and its source as well as the polynucleotide encoding the copper-dependent trans-acting transcription factor.

The host cell may be any fungal cell useful in the methods of the present invention. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No: 9, 1980).

In a more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In an even most preferred aspect, the yeast host cell is *Saccharomyces carlsbergensis cerevisiae* JG169 (MAT-α, ura3-52, leu2-3, pep4-1137, his3Δ2, prb1::leu2, Δpre1::his3) (U.S. Pat. No. 5,770,406).

In another preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichotheciodes,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable procedures for transformation of *Trichoderma reesei* host cells is described in Penttila et al., 1987, *Gene* 61: 155-164, and Gruber et al., 1990, *Curr Genet.* 18(1):71-6. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

The present invention is further described by the following examples which should not be construed as limiting the scope of the invention.

EXAMPLES

Chemicals used as buffers and substrates were commercial products of at least reagent grade.
DNA Sequencing
DNA sequencing was performed using an Applied Biosystems Model 3130X Genetic Analyzer (Applied Biosystems, Foster City, Calif., USA) using dye terminator chemistry (Giesecke et al., 1992, *Journal of Virol. Methods* 38: 47-60). Sequences were assembled using phred/phrap/consed (University of Washington, Seattle, Wash., USA) with sequence specific primers.

Strain
*Saccharomyces cerevisiae* JG169 (MAT-α, ura3-52, leu2-3, pep4-1137, his3Δ2, prb1::leu2, Δpre1::his3) (U.S. Pat. No. 5,770,406) was used as the host strain in the Examples herein.
Culture Media
YPD medium was composed per liter of 10 g of yeast extract, 20 g of Bacto peptone, and 2% glucose.

CUP minus ura medium (pH 7.0) (original medium) was composed per liter of 1 ml of 100 mM $CuSO_4.5H_2O$, 1.7 g of yeast nitrogen base (YNB) without amino acids and ammonium sulfate (BIO101, Carlsbad, Calif., USA), 0.8 g of CSM-ura with 40 mg of adenine (BIO101, Carlsbad, Calif., USA), 5 g of Casamino acids (Becton, Dickenson and Company, Sparks, Md., USA), 100 ml of 50% glucose, 50 ml of 0.5 M $K_2HPO_4$, and 1 ml of 100 mg/ml ampicillin.

Yeast ura minus optimized medium (optimal medium) was composed per liter of 1 ml of 100 mM $CuSO_4.5H_2O$, 6.7 g of yeast nitrogen base (YNB) with ammonium sulfate, 0.8 g of CSM-ura with 40 mg of adenine, 5.9 g of succinic acid (Sigma Chemical Co., St. Louis, Mo., USA), 20 g of galactose, 10 g of glucose, and 1 ml of 100 mg/ml ampicillin.

Yeast ura minus selection medium was composed per liter of 6.7 g of yeast nitrogen base (YNB) with ammonium sulfate, 5 g of Casamino acids, 100 ml of 0.5 M succinic acid pH 5, 40 ml of 50% glucose, and 2 ml of 10 mg/ml chloramphenicol.

Yeast ura minus selection plates were composed of yeast ura minus selection medium supplemented with 20 g of Noble agar per liter.

SC ura minus medium was composed per liter of 7.5 g of yeast nitrogen base without amino acids (Fluka, Buchs, Switzerland), 11.3 g of succinic acid, 6.8 g of sodium hydroxide, 5.6 g of Casamino acids, and 0.1 g of L-tryptophan, and 100 ml of a sterile solution of 50% fructose and 400 µl of a sterile solution of 250 mg/ml of ampicillin, both added after autoclaving.

SC ura minus plates were composed of SC ura minus medium, except 100 ml of sterile 20% fructose is used, and 20 g of agar (Sigma Chemical Co., St. Louis, Mo., USA).

SDMUA medium was composed per liter of 1.7 g of yeast nitrogen base without amino acids, 5.0 g of Casamino acids, 0.8 g of CMS-Ura with 40 mg/l ADE (MP Biomedicals, Irvine, Calif., USA), 10 ml of 10 mM $CuSO_4.5H_2O$, and 10 ml of 1 M $K_2HPO_4$, and 100 ml of sterile 50% fructose and 400 µl of sterile 250 mg/ml of ampicillin, both added after autoclaving.

LB medium was composed per liter of 10 g of tryptone, 5 g of yeast extract, and 5 g of sodium chloride LB plates were composed of LB medium and 15 g of Bacto agar per liter.

SOC medium was composed of 2% tryptone, 0.5% yeast extract, 10 mM NaCl, 2.5 mM KCl, 10 mM $MgCl_2$, and 10 mM $MgSO_4$, sterilized by autoclaving and then filter-sterilized glucose was added to 20 mM.

2×YT plates were composed per liter of 16 g of tryptone, 10 g of yeast extract, 5 g of NaCl, and 15 g of bacto agar.

Example 1

PCR Amplification of a Copper-Inducible Promoter (CUP1 Promoter)

PCR primers 997247 and 997248, shown below, were designed to amplify the *Saccharomyces cerevisiae* copper-inducible promoter (CUP1 promoter) from plasmid pCu426 (Labbe and Thiele, 1999, *Methods in Enzymology* 306: 145-153). Restriction enzyme sites, Age I and Eco RI, were incorporated into the primer design for cloning into the *Saccharomyces cerevisiae* expression plasmid pMB1537 (see Example 2).

```
Primer 997247:
                                          (SEQ ID NO: 25)
5'-CACCGGTGCATGCCTGCAGGAGCTCCTAGTTAGAAA-3'
    Age I Primer 997248:
                                          (SEQ ID NO: 26)
5'-AACTATTCTTGAATGGAATTCTAGTCGATGACTTCT-3'
                 Eco RI
```

The CUP promoter fragment was amplified by PCR using an EXPAND® High Fidelity PCR System (Roche, Indianapolis, Ind., USA). The PCR amplification reaction mixture contained approximately 50 ng of pCu426 plasmid DNA, 1 µl of primer 997247 (50 pmol/µl), 1 µl of primer 997248 (50 pmol/µl), 5 µl of 10×PCR buffer (Roche, Indianapolis, Ind., USA) with 15 mM MgCl$_2$, 1 µl of dNTP mix (10 mM each), 40.25 µl of water, and 0.75 µl (3.5 U/µl) of DNA polymerase mix (Roche, Indianapolis, Ind., USA). An EPPENDORF®, MASTERCYCLER® 5333 (Eppendorf, Westbury, N.Y., USA) was used to amplify the fragment programmed for 1 cycle at 94° C. for 2 minutes, 10 cycles each at 94° C. for 15 seconds, 55° C. for 30 seconds, and 72° C. for 15 seconds; 15 cycles each at 94° C. for 15 seconds, 55° C. for 30 seconds, and 72° C. for 15 seconds plus a 5 second elongation at each successive cycle; 1 cycle at 72° C. for 7 minutes; and a 10° C. hold.

A PCR product of 246 bp was purified by 1.5% agarose gel electrophoresis using TAE buffer (4.84 g of Tris Base, 1.14 ml of glacial acetic acid, and 2 ml of 0.5 M EDTA pH 8.0 per liter) and further purified using a QIAQUICK® Gel Extraction Kit (QIAGEN Inc., Valencia, Calif., USA). The 246 bp PCR product was ligated with pCR2.1-TOPO® (Invitrogen Corporation, Carlsbad, Calif., USA) according to the manufacturer's instructions. After the incubation, 2 µl of the mixture was used to transform ONE SHOT® TOP10 chemically competent *E. coli* cells (Invitrogen Corporation, Carlsbad, Calif. USA). A 2 µl volume of the ligation mixture was added to the *E. coli* cells and incubated on ice for 5 minutes. Subsequently, the cells were heat shocked for 30 seconds at 42° C., and then placed on ice for 2 minutes. A 250 µl volume of SOC medium was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Eight colonies that grew on the plates were picked with sterile toothpicks and grown overnight at 37° C., 250 rpm in a 15 ml FALCON® tube containing 3 ml of LB medium supplemented with 100 µg of ampicillin per ml. The plasmids were isolated using a BioRobot 9600 (QIAGEN Inc., Valencia, Calif., USA).

Four µl volumes of the resulting plasmid minipreps were digested with Eco RI. The digestion reactions were analyzed by agarose gel chromatography and UV analysis as previously described for the PCR reaction. Isolated plasmids containing an insert were sequenced using 1 µl of plasmid template, 1.6 ng of M13 primer (forward or reverse) (MWG Biotech, High Point, N.C., USA), and water to 6 µl. The resulting plasmid with the correct sequence was designated pBM128a (FIG. 1).

Example 2

Construction of Expression Vector pMB1537

Expression vector pMB1537 contains the yeast TPI promoter driving expression of a wild-type gene encoding a *Thermomyces lanuginosus* lipase (SEQ ID NO: 27 is the DNA sequence and SEQ ID NO: 28 is the deduced amino acid sequence; Accession Number O59952), the CYC1 terminator, and the URA3 gene as a selectable marker.

Yeast expression plasmid pSTED226 (WO 05/045018) was PCR amplified using an EXPAND® Long Template PCR System (Roche, Germany) with pSTED226 as template and the following two primers.

```
Primer 319137:
                                          (SEQ ID NO: 29)
5'-TCTAGAGGGCCGCATCATGTAATTAG-3'

Primer 19138:
                                          (SEQ ID NO: 30)
5'-GACGCCATGGTG AAGCTTTCTTTTAATCGT-3'
```

The PCR amplification reaction mixture contained approximately 50 ng of pSTED226 plasmid DNA, 1 µl of primer 319137 (50 pmol/µl), 1 µl of primer 19138 (50 pmol/µl), 5 µl of 10×PCR buffer (Roche, Indianapolis, Ind., USA) with 15 mM MgCl$_2$, 1 µl of dNTP mix (10 mM each), 40.25 µl of water, and 0.75 µl (3.5 U/µl) of DNA polymerase mix (Roche, Indianapolis, Ind., USA). A PTC Peltier Thermal Cycler (Bio-Rad Laboratories, Hercules, Calif., USA) was used to amplify the fragment programmed for 1 cycle at 94° C. for 2 minutes; 10 cycles each at 94° C. for 15 seconds, 55° C. for 30 seconds, and 72° C. for 15 seconds; 15 cycles each at 94° C. for 15 seconds, 55° C. for 30 seconds, and 72° C. for 15 seconds plus a 5 second elongation at each successive cycle; 1 cycle at 72° C. for 7 minutes; and a 10° C. hold. After termination of the PCR procedure a PCR fragment of 5826 bp was purified and eluted with a GFX® PCR DNA and Gel Band Purification Kit according to the manufacturer's instructions (Amersham Biosciences, United Kingdom).

A gene fragment containing the *Thermomyces lanuginosus* wild-type lipase gene was PCR amplified using an EXPAND® High Fidelity PCR System with pENI1298 (WO 00/24883) as template and the following two primers:

```
Primer 349699:
                                          (SEQ ID NO: 31)
5'-CAAGAAGATTACAAACTATCAATTTCATACACAATATAAACGATTAA

AAGAAAGCTCACCATGAGGAGCTCCCTTGTGCTGTTCTTTGTCTCTG-3'

Primer 353031:
                                          (SEQ ID NO: 32)
5'-GAGGGCGTGAATGTAAGCGTGACATAACTAATTACATGATGCGGCCC

TCTAGATTATCAAAGACATGTCCCAATTAACCCGAAGTAC-3'
```

The PCR amplification reaction mixture contained approximately 50 ng of pENI1298 plasmid DNA, 1 µl of primer 349699 (50 pmol/µl), 1 µl of primer 353031 (50 pmol/µl), 5 µl of 10×PCR buffer (Roche, Indianapolis, Ind., USA) with 15 mM MgCl$_2$, 1 µl of dNTP mix (10 mM each), 40.25 µl of water, and 0.75 µl (3.5 U/µl) of DNA polymerase mix (Roche, Indianapolis, Ind., USA). A PTC Pettier Thermal Cycler was used to amplify the fragment programmed for 1 cycle at 94° C. for 2 minutes; 10 cycles each at 94° C. for 15 seconds, 55° C. for 30 seconds, and 72° C. for 15 seconds; 15 cycles each at 94° C. for 15 seconds, 55° C. for 30 seconds, and 72° C. for 15 seconds plus a 5 second elongation at each successive cycle; 1 cycle at 72° C. for 7 minutes; and a 10° C. hold. After termination of the PCR procedure a PCR fragment of 927 bp was purified and eluted with a GFX® PCR DNA and Gel Band Purification Kit according to the manufacturer's instructions.

The resulting two fragments, 5826 bp and 927 bp were transformed into *Saccharomyces cerevisiae* JG169 by electroporation using a GENE PULSER® and Pulse Controller (Bio-Rad, Hercules, Calif., USA) at 1.5 kvolts with a 2 mm gap cuvette according to the manufacturer's procedure. Transformation reactions contained 100 ng of PCR amplified vector DNA mixed with 100 ng of the PCR product containing the lipase gene. Transformation reactions were plated onto yeast ura minus selection plates and incubated for 5 days at 30° C.

Figure 2:
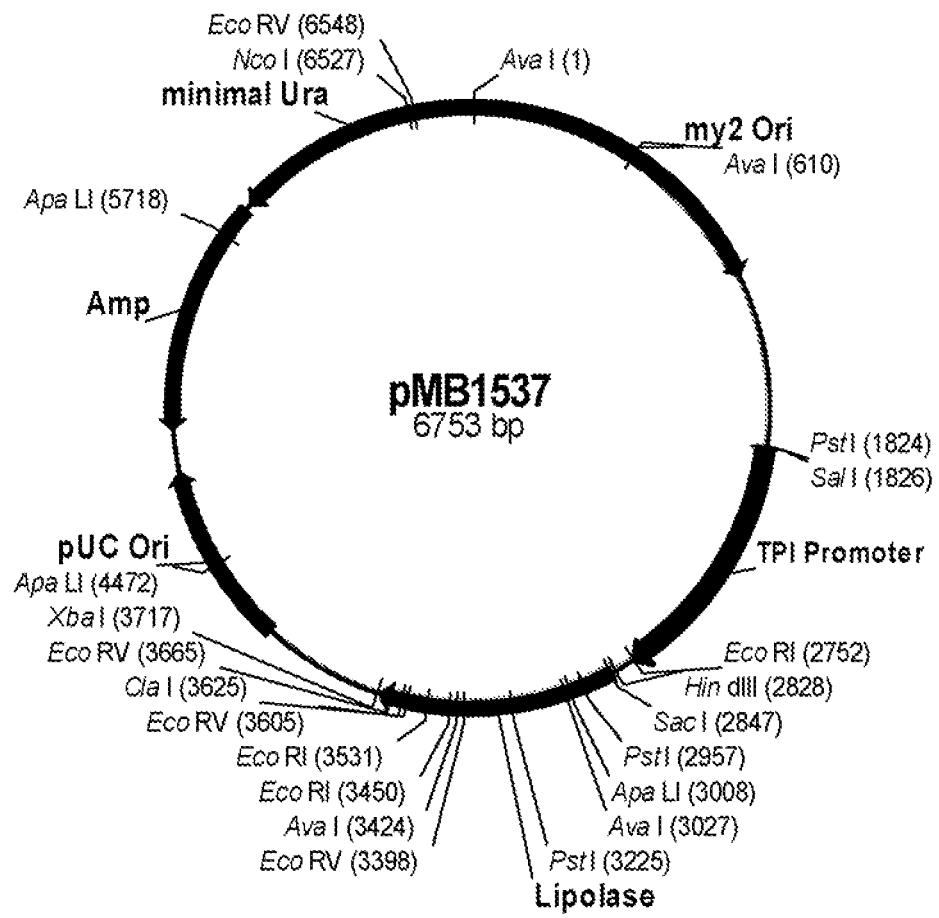
FIG. 2 shows a restriction map of pMB1537.

One yeast clone from the procedure above was restreaked on SC ura minus plates and one single yeast colony was inoculated into 10 ml of SC ura minus medium in a 50 ml shake flask and incubated overnight at 30° C., 250 rpm. Two ml of culture broth was used in a plasmid preparation using a QIAPREP® Spin Miniprep Kit (QIAGEN Inc., Germany) for yeast plasmid preparation. The plasmid was later sequenced and the expected DNA sequence was verified. The plasmid was designated pMB1537 (FIG. 2).

Example 3

Construction of Expression Vector pBM126a

Plasmid pBM128a was digested with Age I and Eco RI, and plasmid pMB1537 was digested with Eco RI and Nde I and the fragments, 265 bp and 661 bp, respectively, were purified by 1.8% and 0.7% agarose get electrophoresis using TAE buffer in conjunction with a QIAQUICK® Gel Extraction Kit. To create the vector fragment, pMB1537 was digested with Age I and Nde I. The resulting 5148 bp fragment was purified by 0.7% agarose gel electrophoresis using TAE buffer in conjunction with a QIAQUICK® Gel Extraction Kit.

Figure 3:
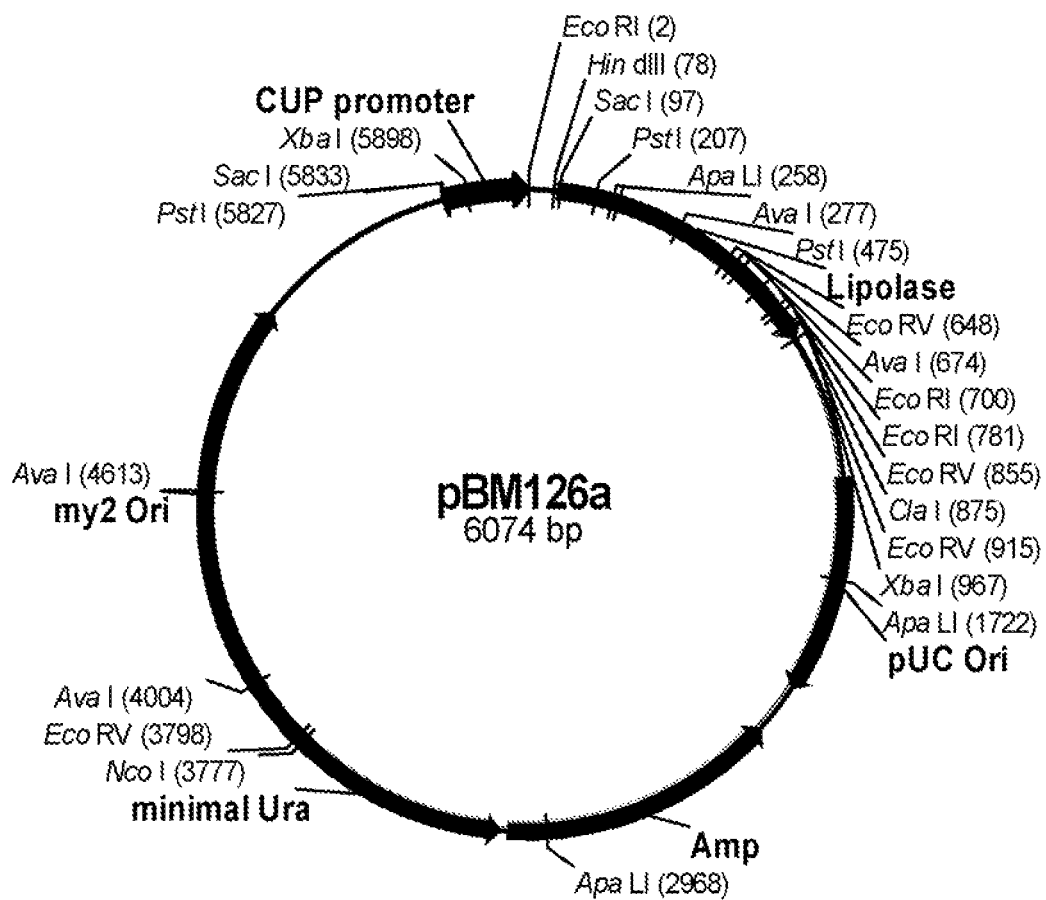

All three fragments were subsequently ligated using a Rapid DNA Ligation Kit (Roche Diagnostics Corporation, Indianapolis, Ind., USA). Two μl of the reaction were used to transform *E. coli* XL10-GOLD® Ultracompetent Cells (Stratagene, La Jolla, Calif., USA) according to manufacturer's instructions. Plasmid DNA was prepared from *E. coli* transformants using a BioRobot 9600. Isolated plasmids containing an insert were sequenced using 1 μl of plasmid template, 1.6 ng of M13 primer (forward or reverse), and water to 6 μl. The resulting plasmid identified as having the correct sequence was designated pBM126a (FIG. 3).

Example 4

Construction of Expression Vector pMB1539

Plasmid pMB1539 was constructed to contain a gene encoding a *Thermomyces lanuginosus* lipase variant (SEQ ID NO: 33 is the DNA sequence and SEQ ID NO: 34 is the deduced amino acid sequence) under control of the TPI promoter.

A gene fragment containing the *Thermomyces lanuginosus* lipase variant gene was prepared by PCR using pENi1298 (WO 00/24883) containing the *Thermomyces lanuginosus* wild-type lipase gene (SEQ ID NO: 27) as template using an EXPAND® High Fidelity PCR System, and primers 349699 and 353031, shown below.

```
Primer 349699:
                                         (SEQ ID NO: 35)
5'-CAAGAAGATTACAAACTATCAATTTCATACACAATATAAACGATTAA

AAGAAAGCTTCACCATGAGGAGCTCCCTTGTGCTGTTCTTTGTCTCT

G-3'
```

```
Primer 353031:
                                         (SEQ ID NO: 36)
5'-GAGGGCGTGAATGTAAGCGTGACATAACTAATTACATGATGCGGCCC

TCTAGATTATCAAAGACATGTCCCAATTAACCCGAAGTAC-3'
```

The PCR amplification reaction mixture contained approximately 50 ng of pENi1298 plasmid DNA, 1 μl of primer 349699 (50 pmol/μl), 1 μl of primer 353031 (50 pmol/μl), 5 μl of 10×PCR buffer (Roche, Indianapolis, Ind., USA) with 15 mM $MgCl_2$, 1 μl of dNTP mix (10 mM each), 40.25 μl of water, and 0.75 μl (3.5 U/μl) of DNA polymerase mix (Roche, Indianapolis, Ind., USA). A PTC Pettier Thermal Cycler was used to amplify the fragment programmed for 1 cycle at 94° C. for 2 minutes; 10 cycles each at 94° C. for 15 seconds, 55° C. for 30 seconds, and 72° C. for 15 seconds; 15 cycles each at 94° C. for 15 seconds, 55° C. for 30 seconds, and 72° C. for 15 seconds plus a 5 second elongation at each successive cycle, 1 cycle at 72° C. for 7 minutes; and a 10° C. hold.

After PCR amplification, a DNA fragment of 993 bp was purified using a GFX® PCR DNA and Gel Band Purification Kit. The resulting fragment (100 ng) was mixed with the pSTED226 vector fragment (100 ng) described in Example 2 and transformed into electrocompetent *Saccharomyces cerevisiae* JG169 cells by electroporation using a GENE PULSER® and Pulse Controller at 1.5 kvolts with a 2 mm gap cuvette according to the manufacturer's procedure. Transformed cells were then plated onto yeast ura minus selection plates and incubated for 5 days at 30° C.

Figure 4:
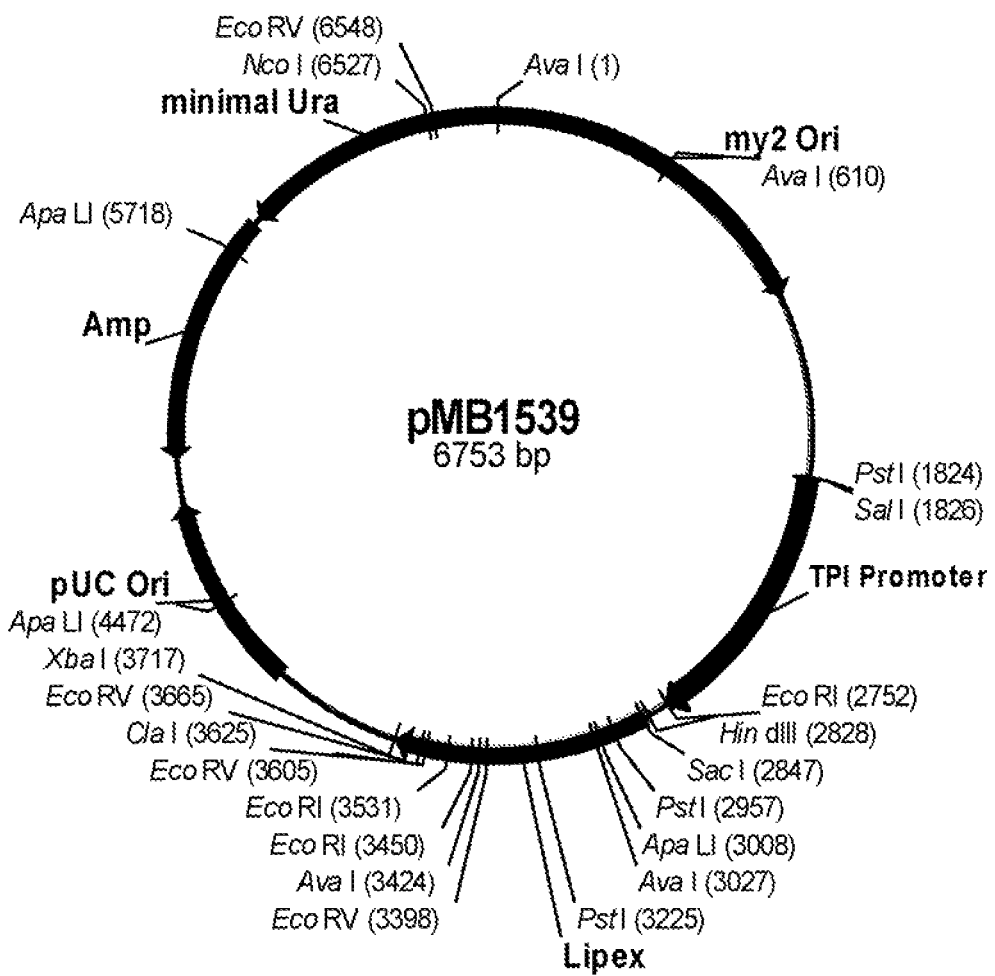
FIG. 4 shows a restriction map of pMB1539.

One yeast clone from the procedure above was restreaked on SC ura minus plates and one single yeast colony was used to inoculate 10 ml of SC ura minus medium in a 50 ml shake flask and incubated overnight at 30° C., 250 rpm. From this culture 2 ml of culture broth were used in a plasmid preparation using a QIAPREP® Spin Miniprep Kit for yeast plasmid preparation. The plasmid was later sequenced and the expected DNA sequence was verified. The plasmid was designated pMB1539 (FIG. 4).

Example 5

Construction of Expression Vector pJLin168

Figure 5:
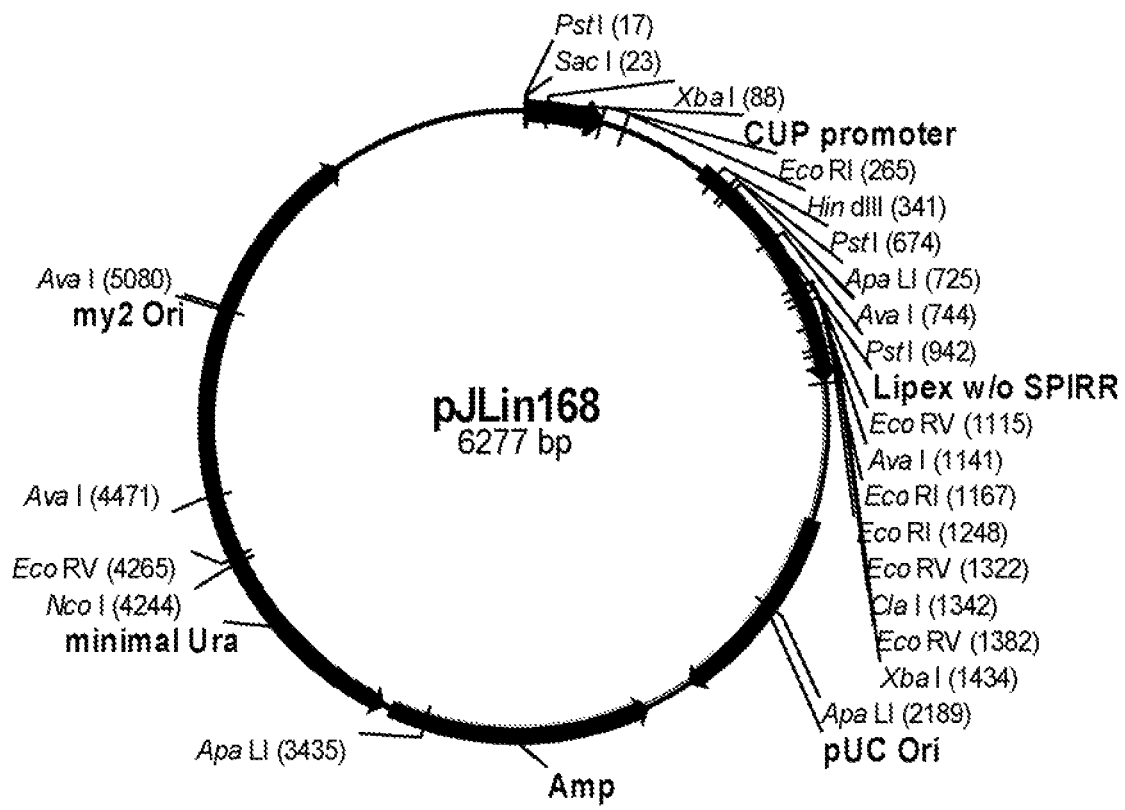
FIG. 5 shows a restriction map of pJLin168.

Construction of a *Thermomyces lanuginosus* lipase variant expression vector utilizing the CUP1 promoter was accomplished by swapping the *Thermomyces lanuginosus* wild-type lipase gene in pBM126a (containing the *Thermomyces lanuginosus* wild-type lipase gene under control of CUP1 promoter) with the *Thermomyces lanuginosus* lipase variant gene from pMB1539. First, both pBM126a and pMB1539 were digested with Hind III and Mlu I, and a 5 kb fragment from pBM126a and a 1.1 kb fragment from pMB1539 were gel-purified using a QIAQUICK® Gel Extraction Kit. Both fragments were subsequently ligated using a Rapid DNA Ligation Kit in molar ratios of vector:insert at 1:2, 1:3, and 1:4 with the vector amount set at 50 ng. The resulting plasmid, designated pJLin168 (FIG. 5), contained the *Thermomyces lanuginosus* lipase variant gene under control of the CUP1 promoter.

Example 6

Construction of Expression Vectors pBM142c and pBM143b

The following primers were designed to remove the last five codons encoding amino acids SPIRR from the propeptide sequence of the *Thermomyces lanuginosus* variant lipase in pJLin168 using a QUIKCHANGE® Site-Directed Mutagenesis Kit (Stratagene, La Jolla, Calif., USA):

Primer 998570:
(SEQ ID NO: 37)
5'-CTCTGCGTGGACGGCCTTGGCCGAGGTCTCGCAGGATCTGTTTAAC-3'

Primer 998571:
(SEQ ID NO: 38)
5'-TTAAACAGATCCTGCGAGACCTCGGCCAAGGCCGTCCACGCAGAG-3'

Figure 6:
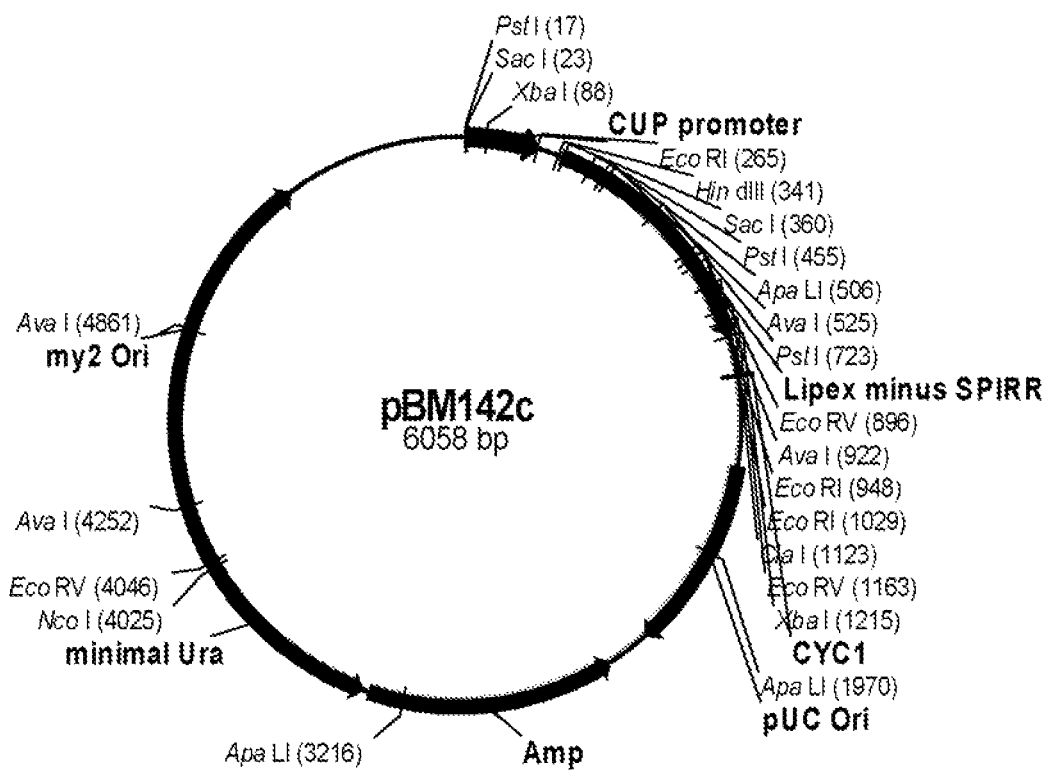
FIG. 6 shows a restriction map of pBM142c.

One hundred picomoles of each primer were used in a PCR reaction containing 73 ng of pJLin168, 1× QUIKCHANGE® reaction buffer (Stratagene, La Jolla, Calif., USA), 4 μl of QUIKSOLUTION® (Stratagene, La Jolla, Calif., USA), 1 μl of XL dNTP mix (Stratagene, La Jolla, Calif. USA), and 1 μl of 2.5 U/μl PfuUltra™ DNA polymerase (Stratagene, La Jolla, Calif., USA), in a final volume of 50 μl. An EPPENDORF® MASTERCYCLER® was programmed for one cycle at 95° C. for 1 minute; 18 cycles each at 95° C. for 50 seconds, 60° C. for 50 seconds, and 68° C. for 6 minutes, and a 10° C. hold. One microliter of Dpn I was added directly to the amplification reaction and incubated at 37° C. for 1 hour. A 2 μl volume of the Dpn I digestion reaction was used to transform *E. coli* XL10-GOLD® Ultracompetent Cells (Stratagene, La Jolla, Calif., USA) according to the manufacturer's instructions. One of the clones without 15 bp corresponding to the SPIRR-coding region was confirmed by DNA sequencing and was designated pBM142c (FIG. 6).

Figure 7:
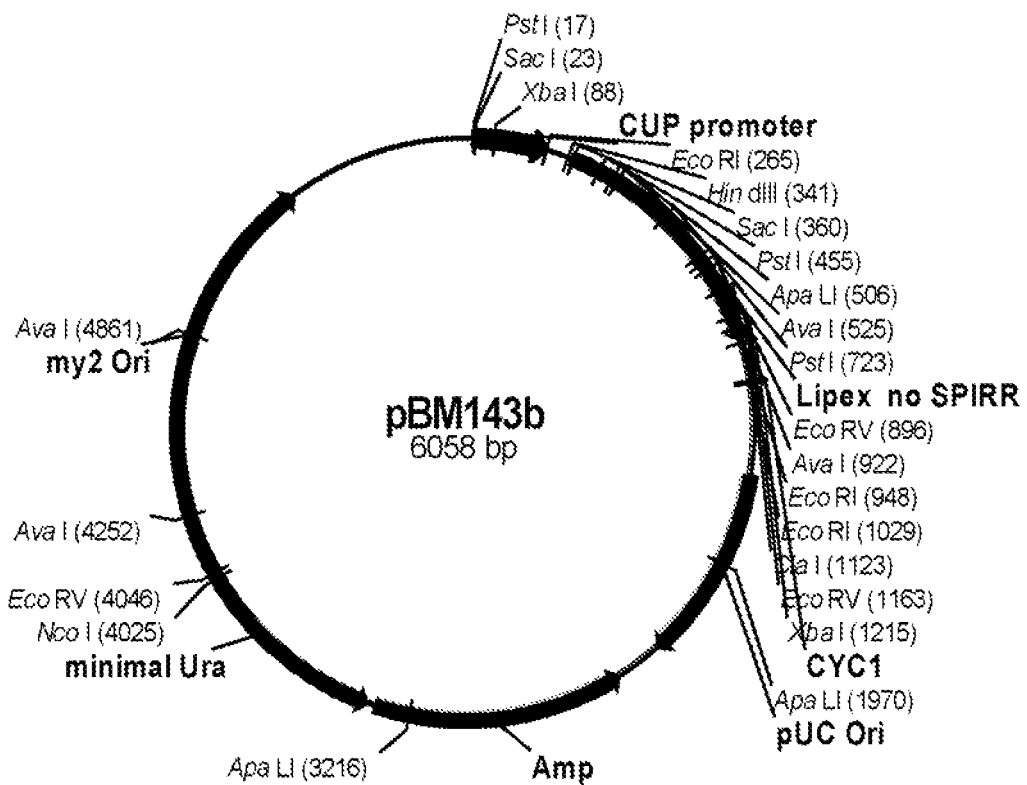
FIG. 7 shows a restriction map of pBM143b.

To avoid additional mutations being generated in pBM142c, the 5' region of *Thermomyces lanuginosus* variant lipase gene from pBM142c was cloned back into pJLin168. Plasmid pBM142c was digested with Hind III and Nde I, and the 0.6 kb fragment was purified by 1.5% agarose gel electrophoresis using TAE buffer in conjunction with a QIAQUICK® Gel Extraction Kit. Plasmid pJLin168 was digested with Hind III and Nde I, and the resulting 5.5 kb fragment was purified by 0.7% agarose gel electrophoresis using TAE buffer in conjunction with a QIAQUICK® Gel Extraction Kit. The two fragments were subsequently ligated using a Rapid DNA Ligation Kit. The resulting expression plasmid, designated pBM143b (FIG. 7), contained the CUP1 promoter driving expression of *Thermomyces lanuginosus* variant lipase gene. Thus, the 22 amino acid signal/propeptide sequence was changed to 17 amino acids by removing the last five amino acids (SPIRR).

Example 7

Construction of Expression Vector pMB1682

Plasmid pMB1537 containing the *Thermomyces lanuginosus* wild-type lipase gene was used to construct a random mutagenized library of the *Thermomyces lanuginosus* lipase signal peptide. The random mutagenized PCR fragment of the signal peptide coding sequence and flanking DNA regions were amplified by PCR using an EXPAND® High Fidelity PCR System and the primers (DNA-Technology, Aarhus, Denmark) below.

Primer 309787:
(SEQ ID NO: 39)
5'-CTAGGAACCCATCAGGTTGGTGGAAG-3'

Primer 373172:
(SEQ ID NO: 40)
5'-CTGTGCAAAGAGATTGAACTGGTTAAACAGATCCTGCGANNNNNNNNNNNNNNNNNNNNNNNNNNNNNNNNNNNNNNNNNNNNNNNNNNNNNNNNNCATGGTGAAGCTTTCTTTTAA-3' where N at positions 41, 50, 51, 60, 64, 66, 68, 70, 71, 72, 74, 75, 77, 80, 82, 83, and 87 of SEQ ID NO: 40 is 99% A and 1% G, C or T;
N at positions 40, 46, 47, 52, 53, 56, 62, 65, 67, 73, 78, 84, 85, 86, and 88 of SEQ ID NO: 40 is 99% G and 1% A, C, or T;
N at positions 42, 43, 45, 48, 49, 54, 55, 58, 59, 61, 63, 69, 76, 79, 81, 89, 91, and 92 of SEQ ID NO: 40 is 99% C and 1% A, G, or T; and
N at positions 44, 57, 90, and 93 of SEQ ID NO: 40 is 99% T and 1% A, C, or G.

The primer introducing the diversity was designed after the following rules: The wild-type base at the randomized positions was always present at 99% and the other three bases were present at 1% and all three were equally represented.

The mutagenized fragment of the signal peptide coding sequence was amplified by PCR using an EXPAND® High Fidelity PCR System. The PCR amplification reaction mixture contained approximately 50 ng of pMB1537, 1 μl of primer 309787 (50 pmol/μl), 1 μl of primer 373172 (50 pmol/μl), 5 μl of 10×PCR buffer (Roche, Indianapolis, Ind., USA) with 15 mM MgCl₂, 1 μl of dNTP mix (10 mM each), 40.25 μl of water, and 0.75 μl (3.5 U/μl) of DNA polymerase mix (Roche, Indianapolis, Ind., USA), A PTC Peltier Thermal Cycler was used to amplify the fragment programmed for 1 cycle at 94° C. for 2 minutes; 10 cycles each at 94° C. for 15 seconds, 55° C. for 30 seconds, and 72° C. for 15 seconds; 15 cycles each at 94° C. for 15 seconds, 55° C. for 30 seconds, and 72° C. for 15 seconds plus a 5 second elongation at each successive cycle; 1 cycle at 72° C. for 7 minutes; and a 10° C. hold.

A gene fragment of the *Thermomyces lanuginosus* wild-type lipase gene was prepared by PCR using pMB1537 as template in a PCR reaction using an EXPAND® High Fidelity PCR System. The primers used in the PCR were primers 309787 and 373172 described above.

After PCR amplification, a PCR fragment of 600 bp was purified using a GFX® PCR DNA and Gel Band Purification Kit according to the manufacturer's protocol and eluted in 50 μl of 10 mM Tris-HCl pH 8.0.

Plasmid pMB1537 was linearized by digestion with Sac I at a DNA position within the signal peptide coding sequence. The linearized vector was used as the recipient DNA in a transformation of *Saccharomyces cerevisiae* JG169 using a PCR fragment of the signal peptide coding sequence with flanking DNA regions (100% homologous to the recipient DNA of the recipient plasmid) as the donor DNA.

Specifically, approximately 3 μg of Sac I digested pMB1537 together with approximately 1 μg of the 600 bp PCR fragment were electroporated into 100 μl of electrocompetent *Saccharomyces cerevisiae* JG169 cells using a GENE PULSER® and Pulse Controller at 1.5 kvolts with a 2 mm gap cuvette. After electroporation the transformed cells were supplied with 1 ml of 1 M sorbitol, and incubated for 1 hour at 30° C. after which 1.1 ml were plated onto SC ura minus plates supplemented with 100 μg of ampicillin per ml.

A total of 8400 colonies from the SC ura minus plates supplemented with 100 μg of ampicillin per ml were picked and transferred to 96-well polystyrene microwell plates, applying the picked clones to the wells in rows B-H and columns 1-12 leaving row A free, which was inoculated with the wild-type plasmid construct in *Saccharomyces cerevisiae* JG169 as the wild-type reference. All wells contained SD Medium-URA with 40 mg of adenine added per liter (called SDMUA) (following recommendations from the manufacturer, Qbiogene, Inc., BIO 101® System, supplied by AH Diagnostics, Aarhus, Denmark). The plates were incubated at 30° C. and 250 rpm for 5 days. After 5 days the plates were kept at 4° C. before measuring lipase activity using a p-nitrophenyl valerate assay described below.

Lipase activities of culture supernatants were measured using p-nitrophenyl valerate as a substrate in the following assay. Culture supernatants were diluted in 50 mM Tris pH 7, 10 mM $CaCl_2$, 0.4% TRITON® X-100 (4-(1,1,3,3-tetramethylbutyl)phenyl-polyethylene glycol) buffer (dilution buffer). A LIPOLASE™ standard (Novozymes A/S, Bagsværd, Denmark) was diluted using two-fold steps starting with a 1.0 LU/ml concentration and ending with a 0.125 LU/ml concentration in the sample buffer. In polystyrene microwell plates, 10 μl of supernatant were mixed with 90 μl of the dilution buffer. One hundred microliters of a p-nitrophenyl valerate substrate solution (117 μl of p-nitrophenyl valerate dissolved in 10 ml of isopropanol) was added to each well, briefly mixed, and then the absorbance at 405 nm was measured for 3 minutes every 12 seconds. The assay data was evaluated to identify all samples having higher activity than the pMB1539 construct in *Saccharomyces cerevisiae* JG169 (in the A-row wells).

All clones with higher activity than the reference were collected as positive hits, which were reanalyzed in the same set-up and all clones still having higher activity than the reference were used as inoculation material with fresh SDMUA medium in microwell plates. The A-row was again used for the reference strain. The plates were incubated as above, and analyzed as described above.

All clones with higher activity than the reference were removed from their wells and restreaked on SC-agar plates. Single colonies of all clones were collected for regrowth in microwell plates in 200 μl of SDMUA medium and 50 ml tubes containing 10 ml of SDMUA medium and incubated at 3000 for 5 days after which yields were compared to that of the reference strain using the p-nitrophenyl valerate assay described above.

Each clone was grown in three adjacent microwells and 3 individual 60 ml tubes. Mean values of the three growth experiments were used for the comparison of activity levels.

Finally the clones with the highest lipase activity in both microwell plates and 50 ml tubes were inoculated in shake flasks (250 ml conical baffled shake flasks with two baffles) containing 10 ml of SDMUA medium and incubated at 250 rpm for 5 days at 30° C. Supernatants were assayed for lipase activity using the p-nitrophenyl valerate assay described above. Clones with the highest lipase activity were DNA sequenced.

The clone showing the highest activity was designated MB1665, which had a R2K substitution in the signal peptide of the lipase (second codon of the signal peptide was altered from AGG to AAG).

By using the same principle as described in Example 4, DNA encoding this signal peptide was transferred to the pMB1539 construct encoding the *Thermomyces lanuginosus* lipase variant. In this case the smaller PCR fragment was made using the same procedure as described in Example 4. However, the larger fragment was made also according to Example 4 but using plasmid DNA from MB1539 as the template. GAP-repair and transformation of the *Saccharomyces cerevisiae* JG169 was performed as described above. This cloning resulted in a clone with higher expression of the *Thermomyces lanuginosus* lipase variant. This clone was designated *Saccharomyces cerevisiae* MB1681.

Figure 8:
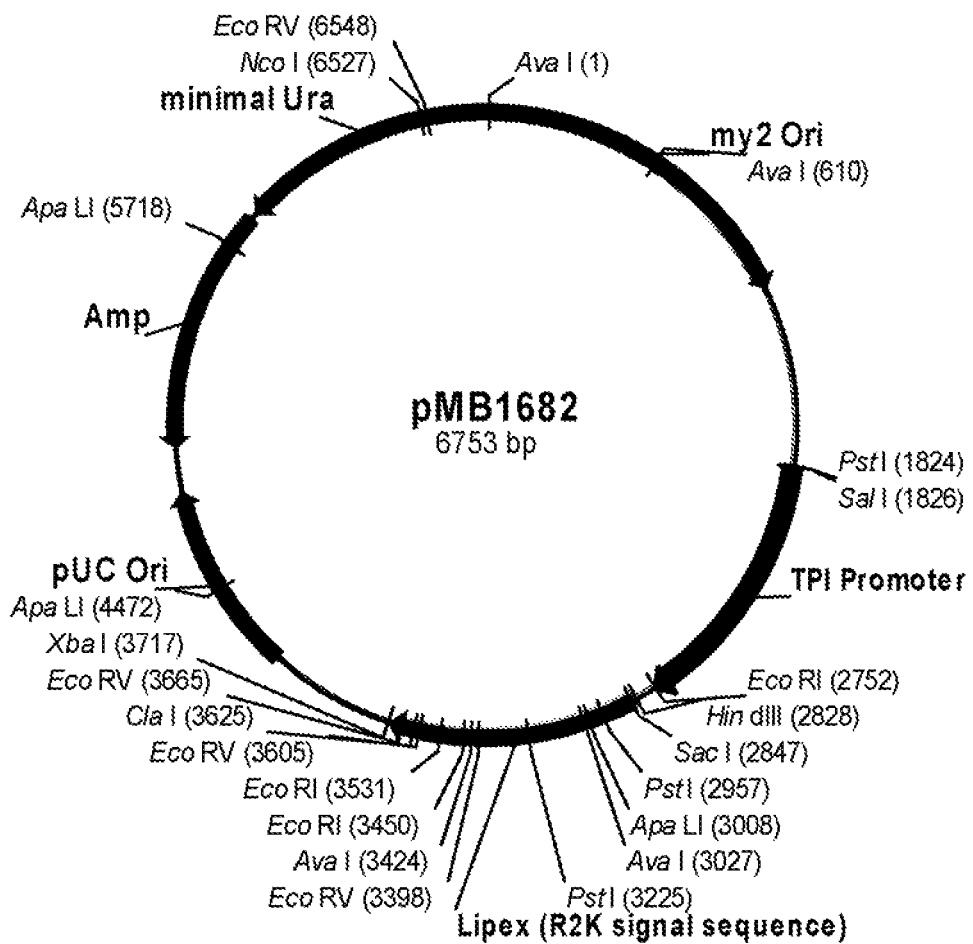
FIG. 8 shows a restriction map of pMB1682.

*Saccharomyces cerevisiae* MB1681 cell material from a SC-agar plate (grown 5 days at 30° C.) was used to inoculate 10 ml of SC ura minus medium in a 50 ml shake flask and incubated overnight at 30° C., 250 rpm. From this culture 2 ml of culture broth was used in a plasmid preparation using a QIAPREP® Spin Miniprep Kit for yeast plasmid preparation The purified plasmid was transformed into *E. coli* Top10F' (Invitrogen, Carlsbad, Calif., USA) according to manufacturer's instructions. Transformed *E. coli* cells were plated onto LB plates supplemented with 100 μg of ampicillin per ml. A single colony was isolated, restreaked, inoculated into LB medium, and incubated overnight at 30° C. One ml of the overnight culture was used for plasmid preparation using a QIAPREP® Spin Miniprep Kit. Finally, the isolated plasmid was used as template for DNA sequencing, verifying the sequence of the variant signal sequence (SEQ ID NO: 41) and the *Thermomyces lanuginosus* lipase variant coding region (SEQ ID NO: 33 with the deduced amino acid sequence of SEQ ID NO: 34). The resulting plasmid was designated pMB1682 (FIG. 8). Plasmid pMB1682 comprised the TPI promoter and the *Thermomyces lanuginosus* lipase variant coding region (without SPIRR with a R2K change).

Example 8

Construction of Expression Vector pJLin195

Plasmid pJLin195 was constructed to contain the *Thermomyces lanuginosus* lipase variant (with signal sequence containing a R2K change and without SPIRR) expression vector utilizing the *Saccharomyces cerevisiae* CUP1 promoter.

Figure 9:
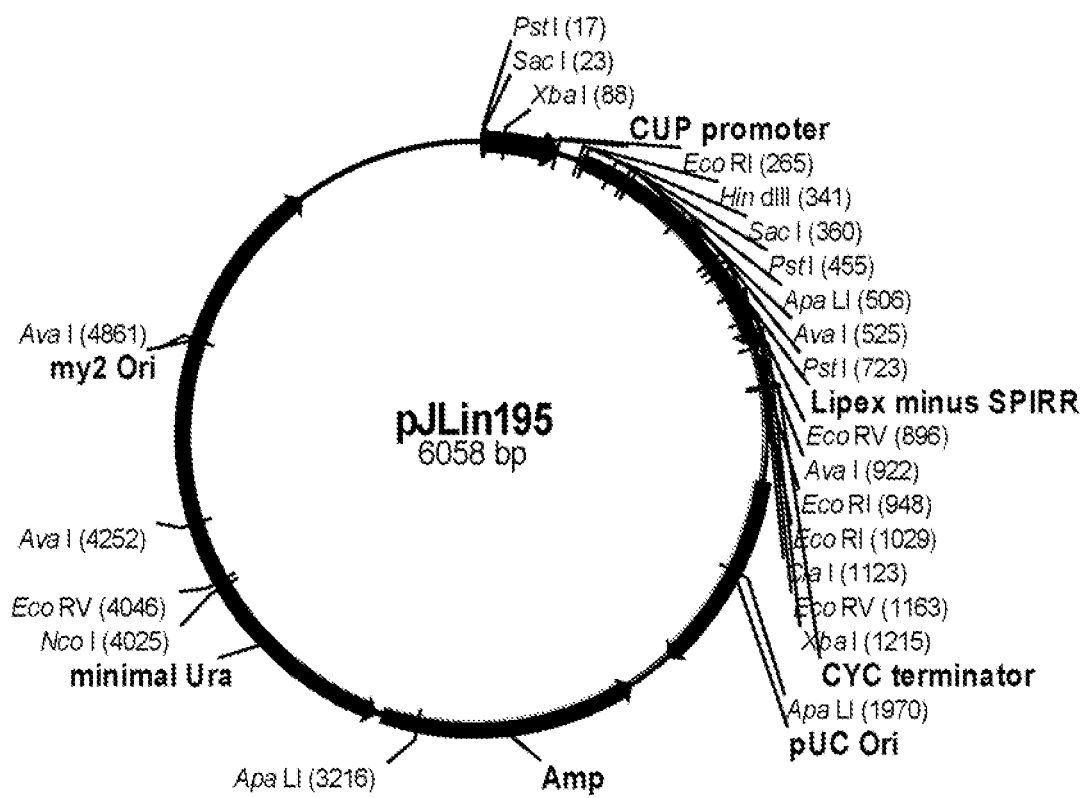
FIG. 9 shows a restriction map of pJLin195.

The Hind III-Nde I fragment of pMB1682 was cloned into pBM143b digested with Hind III and Nde I, replacing the coding sequence of the second amino acid Arg (AGG) with the coding sequence of Lys (AAG). Both pMB1682 and pBM143b were digested with Hind III and Nde I, and a 1 kb fragment from pMB1682 and a 5 kb fragment from pBM143b were gel extracted with a QIAQUICK® Gel Extraction column. The fragments were ligated together in a molar ratio of vector to insert at 1:2, 1:1, and 3:1 with a vector amount of 50 ng using a Rapid DNA Ligation Kit according to the manufacturer's instructions. The resulting plasmid, confirmed by DNA sequencing, was designated pJLin195 (FIG. 9).

Example 9

Construction of Expression Vector pBM165a

The following primers were used to generate a PCR fragment for constructing an expression vector containing four *Saccharomyces cerevisiae* upstream activating sequences (UAS):

```
Primer 999003:
5'-CCGGTGCATGCCTGCAGGAGCTCCT-3'      (SEQ ID NO: 42)
     Sph I Primer 999005:
5'-ACCGGTCTTTTTTGCTGGAACGGTTCA-3'    (SEQ ID NO: 43)
     Age I
```

The fragment was amplified by PCR using an EXPAND® High Fidelity PCR System. The PCR mixture contained 0.5 μl of approximately 25 ng of pBM143b DNA, 1 μl of primer 999003 (50 pmol/μl), 1 μl of primer 999005 (50 pmol/μl), 5 μl of 10×PCR buffer with 15 mM MgCl$_2$, 1 µl of dNTP mix (10 mM each), 40.25 µl of water, and 0.75 µl of DNA polymerase mix (3.5 U/µl). An EPPENDORF® MASTERCYCLER® was used to amplify the fragment programmed for 1 cycle at 94° C. for 2 minutes; 10 cycles each at 94° C. for 15 seconds, 55° C. for 30 seconds, and 72° C. for 30 seconds; 15 cycles each at 94° C. for 15 seconds, 55° C. for 30 seconds, and 72° C. for 30 seconds plus 5 second elongation at each successive cycle; 1 cycle at 72° C. for 7 minutes; and a 10° C. hold.

The resulting 147 bp PCR fragment was purified by 1.8% agarose gel electrophoresis using TAE buffer in conjunction with a QIAQUICK® Gel Extraction Kit and the 147 bp PCR product was ligated with pCR2.1-TOPO® according to the manufacturer's instructions. A 1 µl volume of fresh PCR product, 3 µl of double-distilled water, and 1 µl of the TOPO® cloning vector were mixed with a pipette and incubated at room temperature for 5 minutes.

After the incubation, 2 µl of the mixture was used to transform ONESHOT® TOPIC chemically competent E. coli cells. A 2 µl volume of the ligation mixture was added to the E. coli cells and incubated on ice for 5 minutes. Subsequently, the cells were heat shocked for 30 seconds at 42° C., and then placed on ice for 2 minutes. A 250 µl volume of SOC medium was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Eight colonies that grew on the plates were picked with sterile toothpicks and grown overnight at 37° C., 250 rpm in a 15 ml FALCON® tube containing 3 ml of LB medium supplemented with 100 µg of ampicillin per ml. The plasmids were isolated using a BioRobot 9600.

Figure 10:
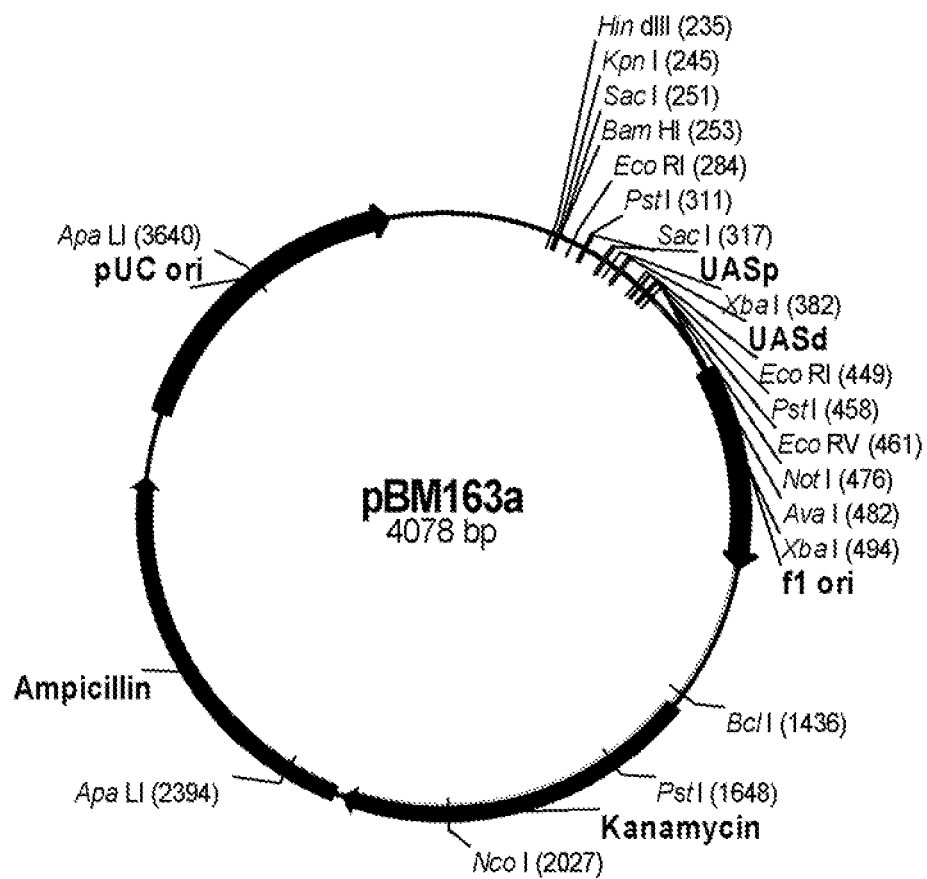

Four µl volumes of the resulting plasmid minipreps were digested with Eco RI. The digestion reactions were analyzed by agarose gel chromatography as previously described for the PCR reaction. Isolated plasmids containing an insert were sequenced using 1 µl of plasmid template, 1.6 ng of M13 primer (forward or reverse), and water to 6 µl. The resulting plasmid was confirmed by DNA sequencing, and designated pBM163a (FIG. 10).

Figure 11:
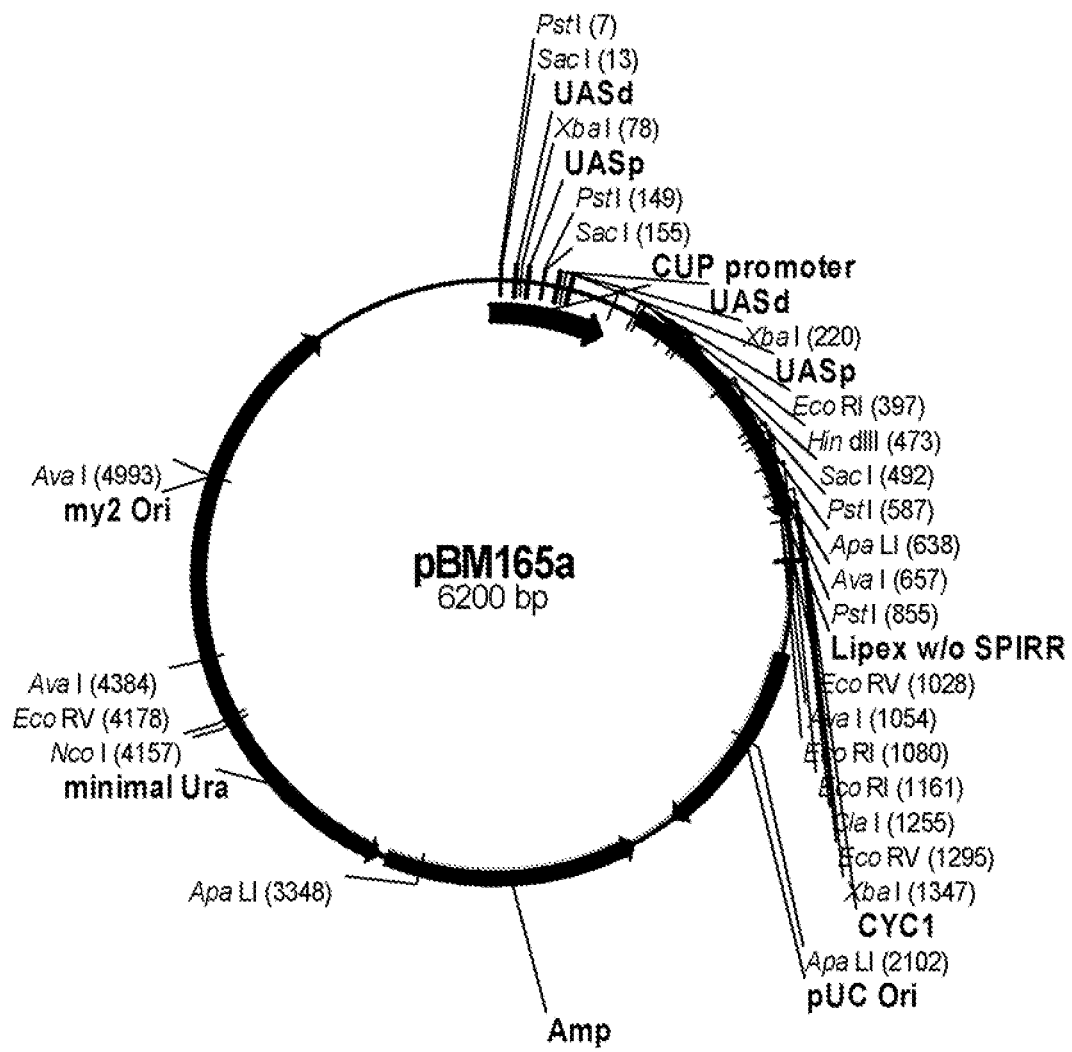

To create the final expression construct containing four UAS sequences, pBM163a was digested with Sph I and Age I, and plasmid pJLin168 with Age I and Hind III. The 132 bp Sph I-Age I and 340 bp Age I-Hind III fragments were cloned into the *Thermomyces lanuginosus* variant lipase expression vector pBM143b, which had been previously digested with Sph I and Hind III. The resulting plasmid was designated pBM165a (FIG. 11).

Example 10

Construction of ACE1 Overproducing Expression Vectors

The following PCR primers were designed to amplify the ACE1 gene from genomic DNA of *Saccharomyces cerevisiae* strain S288C (ATCC 20458). A Bsp HI restriction site was incorporated for cloning into the expression plasmids pBM143b and pJLin195.

```
Primer 999262:
5'-TCATGATACGATCGTGAAAGAATAT-3'    (SEQ ID NO: 44)
    BspHI

Primer 999263:
5'-TCATGAGGATGATGACAAAGAAGAC-3'    (SEQ ID NO: 45)
    BspHI
```

The ACE1 gene fragment was amplified by PCR using an EXPAND® High Fidelity PCR System. Genomic DNA was isolated from *Saccharomyces cerevisiae* strain S288C using a YEASTAR™ Genomic DNA Kit (ZYMO Research, Orange, Calif., USA) according to the manufacturer's instructions. The PCR reaction contained 0.1 µg of *Saccharomyces cerevisiae* S288C genomic DNA, 1 µl of primer 999262 (50 pmol/µl), 1 µl of primer 999263 (50 pmol/µl), 5 µl of 10×PCR buffer with 15 mM MgCl$_2$, 1 µl of dNTP mix (10 mM each), 40.25 µl of water, and 0.75 µl (3.5 U/µl) of DNA polymerase mix in a final volume of 50 µl. An EPPENDORF® MASTERCYCLER® was used to amplify the fragment programmed for 1 cycle at 94° C. for 2 minutes, 10 cycles each at 94° C. for 15 seconds, 55° C. for 30 seconds, and 72° C. for 1 minute 45 seconds; 15 cycles each at 94° C. for 15 seconds, 55° C. for 30 seconds, and 72° C. for 1 minute 45 seconds plus a 5 seconds elongation at each successive cycle; 1 cycle at 72° C. for 7 minutes; and a 10° C. hold.

Figure 12:
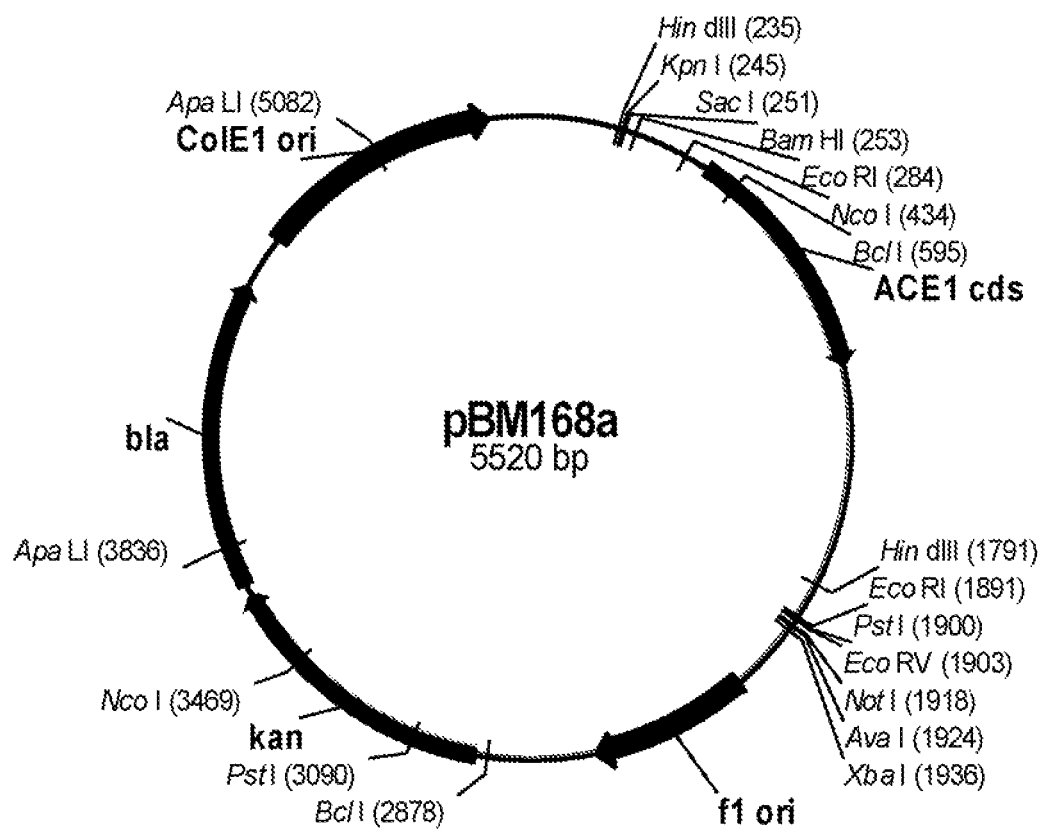

The resulting 1589 bp PCR fragment was purified by 1.8% agarose gel electrophoresis using TAE buffer in conjunction with a QIAQUICK® Gel Extraction Kit. The 1589 bp PCR product was ligated with pCR2.1-TOPO® according to the manufacturer's instructions. The resulting plasmid, designated pBM168a (FIG. 12), was confirmed by nucleotide sequencing.

Figure 13:
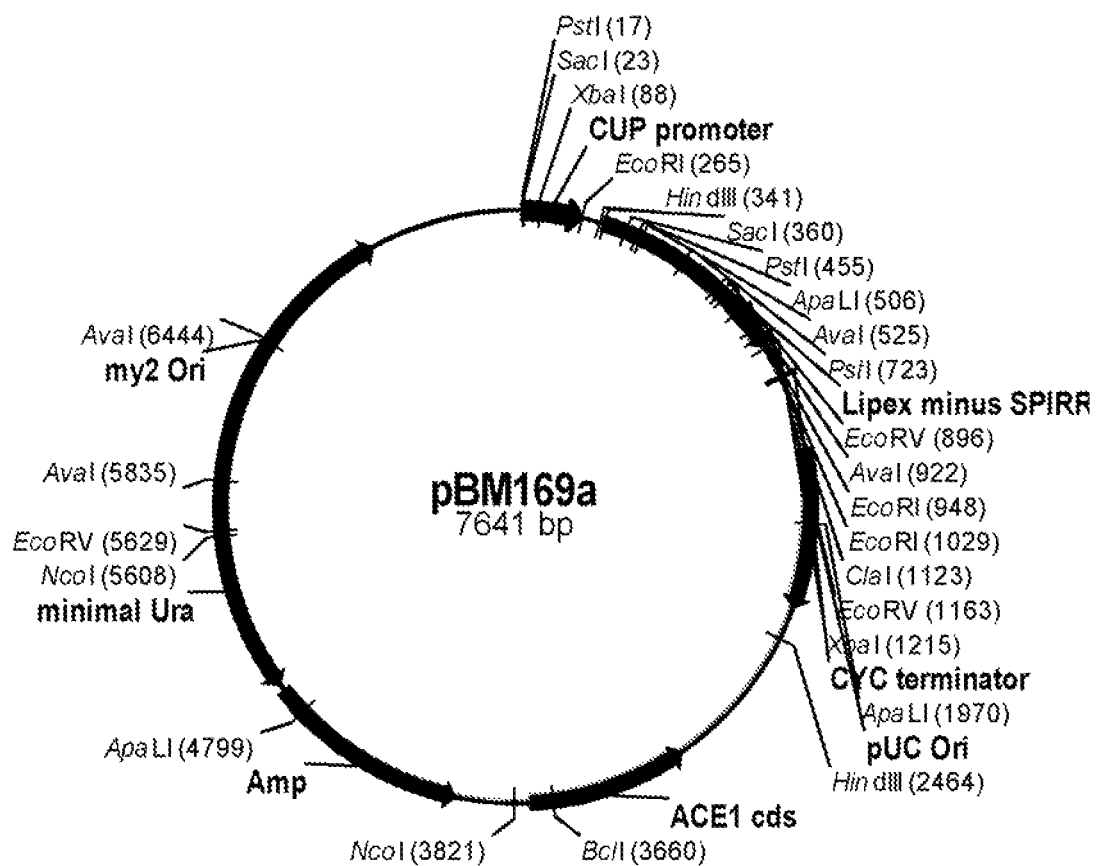
Figure 14:
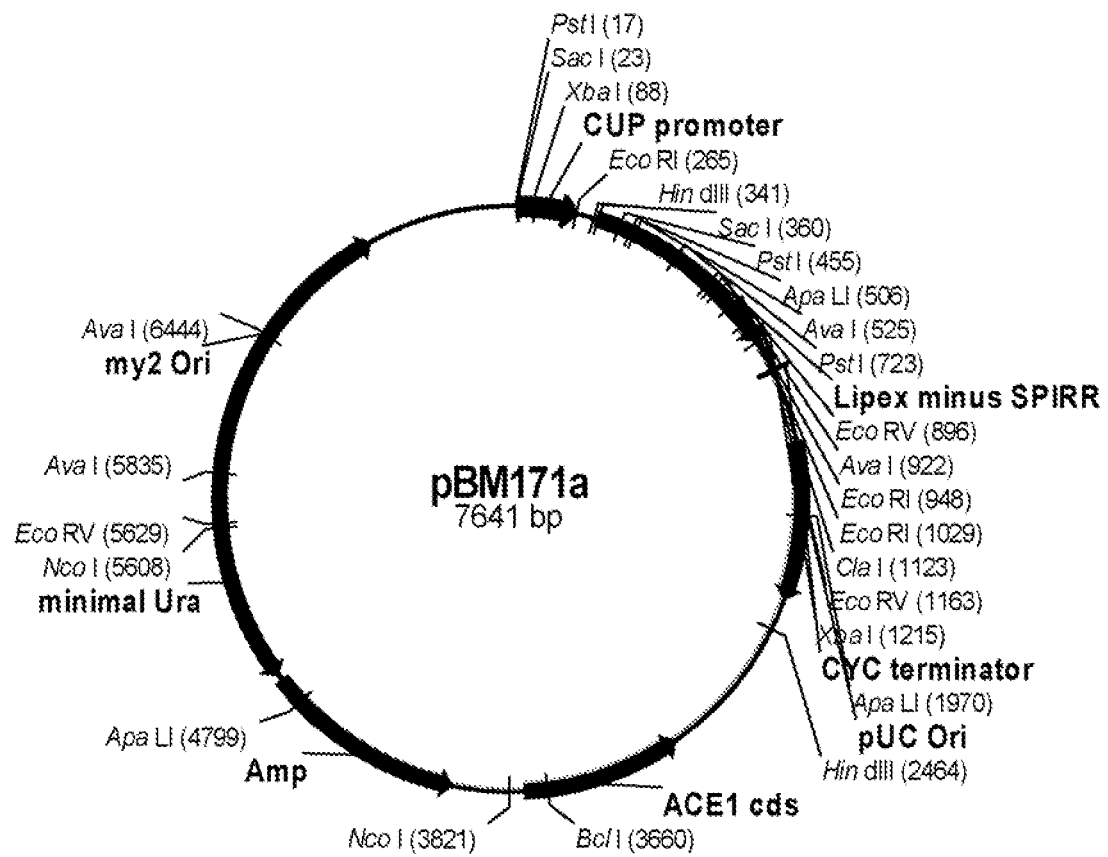
Figure 15:
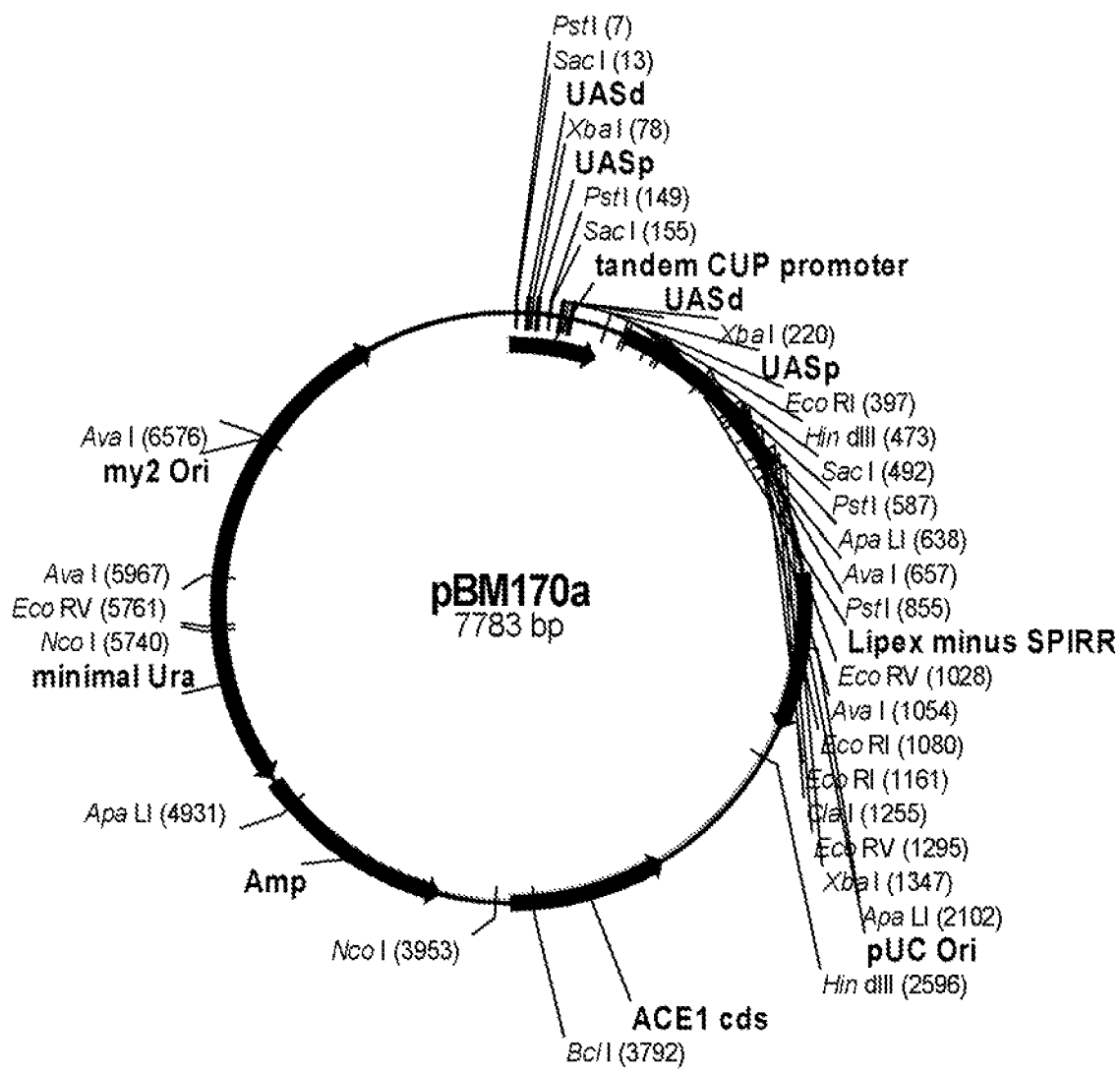

Plasmid pBM168a digested with Bsp HI and the ACE1 gene segment (1583 bp) were cloned into expression vectors pBM143b, pJLin195, and pBM165a, which had been digested with the same enzyme. The fragments were gel extracted with a QIAQUICK® Gel Extraction column. The fragments were ligated together in a molar ratio of vector to insert of 1:2, 1:1, and 3:1 with a vector amount of 50 ng using a Rapid DNA Ligation Kit following the manufacturer's instructions. The resulting plasmids were designated pBM169a (FIG. 13), pBM171a (FIG. 14), and pBM170a (FIG. 15).

Example 11

Yeast Transformation with pBM143b, pJLin195 pBM165a, pBM169a, pBM170a, and pBM171a Plasmids pBM143b, pJLin195, pBM165a, pBM169a, pBM170a, and pBM171a were each transformed into *Saccharomyces cerevisiae* JG169 cells using a YEASTMAKER™ Yeast Transformation System (Clonetech, Palo Alto, Calif., USA) according to the manufacturer's instructions. Briefly, one colony of *Saccharomyces cerevisiae* JG169 was used to inoculate 50 ml of YPD medium and incubated at 30° C. overnight on an orbital shaker (250 rpm).

When the cells reached an absorbance of 0.4 to 0.5 at 600 nm, the cells were centrifuged at 700×g for 5 minutes, the supernatant was discarded, and the pellet was resuspended in 30 ml of deionized water. After centrifugation at 700×g for 5 minutes in a Sorvall RT 6000D centrifuge the cell pellet was resuspended in 1.5 ml of 1.1×TE/lithium acetate solution (110 mM lithium acetate, 11 mM Tris, pH 8, 1.1 mM EDTA). After centrifugation at 12,000×g in a microcentrifuge for 15 seconds, the cell pellet was resuspended in 600 µl of 1.1×TE/lithium acetate solution. After addition of approximately 0.5 µg of pBM143b, pJLin195, pBM165a, pBM170a, or pBM171a, 250 µl of PEG/lithium acetate solution (40% PEG 4000, 0.1 M lithium acetate, 10 mM Tris-HCl, pH 8, 1 mM EDTA), and 5 µl of 10 mg/ml denatured Herring Testes Carrier DNA to 50 µl of competent cells, the mixtures were shaken at 550 rpm at 30° C. for 30 minutes, and cells were mixed by inversion every 10 minutes. A total volume of 20 µl of DMSO was added to each transformation mixture, and incubated at 42° C. for 15 minutes, and the mixture was inverted every 5 minutes. The transformation mixtures were centrifuged for 15 seconds at 12,000×g in a microcentrifuge, and the cells were resuspended in 1 ml of YPD PLUS™ Liquid Medium (YEASTMAKER™ Yeast Transformation System, Clonetech, Palo Alto, Calif., USA) and shaken at 550 rpm and 30° C. for 90 minutes. After centrifugation, the cells were washed with 1 ml of 0.9% NaCl solution and resuspended in 1 ml of yeast ura minus selection medium in the presence of 15% glycerol. Fifty microliters of each transformation reaction were plated in duplicate onto yeast ura minus selection plates and incubated at 30° C. until colonies appeared.

*Saccharomyces cerevisiae* JG169 transformants containing pBM143b, pJLin195, pBM165a, pBM169a, pBM170a, or pBM171a were used to inoculate 180 μl of ura minus selection medium in 96-well plates and were incubated at 30° C., 250 rpm overnight. The overnight cultures were then diluted 100-fold in 180 μl of copper-inducing "original" or "optimal" medium and grown for five days at 30° C.

Lipase activities of culture supernatants were measured using p-nitrophenyl butyrate (pNB) as a substrate in the following assay: Culture supernatants were initially diluted ⅟₁₅-fold in 0.1 M MOPS, 4 mM CaCl$_2$, 0.01% TRITON® X-100 (4-(1,1,3,3-tetramethylbutyl)phenyl-polyethylene glycol) buffer, pH 7.5 (sample buffer), followed by serial dilution from 0-fold to ⅓-fold to ⅑-fold of the diluted sample. A LIPOLASE™ standard (Novozymes A/S, Bagsværd, Denmark) was diluted using two-fold steps starting with a 1.0 LU/ml concentration and ending with a 0.125 LU/ml concentration in the sample buffer. A total of 20 μl of each dilution, including the standard, were transferred to a 96-well flat bottom plate. Two hundred microliters of a p-nitrophenyl butyrate substrate solution (the ratio of p-nitrophenyl butyrate:DMSO:0.1M MOPS pH 7.5 was 1:99:400) was added to each well, and then incubated at 25° C. for 15 minutes. Upon completion of the incubation, the absorbance at 405 nm was measured for the 96-well plate. Sample concentrations were determined by extrapolation from the generated standard curve. For shake flask analysis, representative transformants were inoculated into 2 ml of ura minus selection medium and incubated at 30° C., 250 rpm overnight. The overnight cultures were then diluted 200-fold in 25 ml of CUP minus ura medium in 125 ml glass shake flasks and grown for six days at 30° C. Samples were harvested, centrifuged at 12,000×g, in a microcentrifuge for 10 seconds, and supernatants tested for lipase activity using the p-nitrophenyl butyrate assay described above.

Ten microliters of culture supernatant were mixed with Laemmli Sample buffer (Bio-Rad Laboratories, Inc., Hercules, Calif., USA) in a 1:2 ratio. After boiling for 2 minutes, samples were loaded onto a 10-20% SDS-PAGE gel (Bio-Rad Laboratories, Inc., Hercules, Calif., USA) along with 15 μl of PRECISION PLUS PROTEIN™ Standards (Bio-Rad Laboratories, Inc., Hercules, Calif., USA). Gels were run in 1× Tris-glycine-SDS running buffer (Bio-Rad Laboratories, Inc., Hercules, Calif., USA) at 200 V for 1 hour. The gels were then rinsed 3 times with water for 5 minutes each, and stained with BIO-SAFE™ Coomassie Stain (Bio-Rad Laboratories, Inc., Hercules, Calif., USA) for 1 hour followed by destaining with water for at least 30 minutes.

*Saccharomyces cerevisiae* JG169 transformants containing pBM143b, pJLin195, pBM169a, or pBM171a (24 for each plasmid) were grown in "original" copper containing medium in 96-well plates for five days. Lipase activities in culture broth samples were assayed using p-nitrophenyl butyrate as a substrate as described above. The average relative lipase activities for pBM143b, pBM169a, pJLin195, and pBM171a transformants were 100, 202, 196, and 506, respectively, as shown in Table I.

TABLE I

| plasmid | wild-type promoter UAS sequences | additional UAS sequences | signal sequence | ACE1 | medium | relative activity |
|---|---|---|---|---|---|---|
| pBM143b | 2 | 0 | wild-type | no | original | 100 |
| pJLin195 | 2 | 0 | variant | no | original | 196 |
| pBM169a | 2 | 0 | wild-type | yes | original | 202 |
| pBM171a | 2 | 0 | variant | yes | original | 506 |

The results shown in Table I indicated that by over-producing the Ace1p transcriptional activator with a high copy plasmid, *Thermomyces lanuginosus* variant lipase expression levels were doubled.

*Thermomyces lanuginosus* variant lipase activity in yeast transformants was shown to be improved for transformants grown in "optimal" medium containing succinic acid as a buffer and a mixture of galactose and glucose as the primary carbon source.

To test whether *Thermomyces lanuginosus* variant lipase expression levels in Ace1p over-producing transformants could be further enhanced in "optimal" medium, *Thermomyces lanuginosus* variant lipase activity was measured from *Saccharomyces cerevisiae* strain JG169 transformants containing pBM143b, pJLin195, pBM169a, or pBM171a grown in "original" or "optimal" copper containing medium in 96-well plates. All four expression plasmids were evaluated as described above.

The average relative lipase activities for pBM143b, pBM169a, pJLin195, and pBM171a transformants in "original" medium were 100, 190, 170, and 402, respectively. The average relative lipase activities for pBM143b, pBM169a, pJLin195, and pBM171a transformants grown in "optimal" medium were 240, 318, 285, and 266, respectively, as shown in Table II. Higher overall expression from transformants grown in "optimal" medium was observed from all plasmids. The effect of Ace1p overexpression on *Thermomyces lanuginosus* variant lipase production was approximately 30% higher when comparing plasmid pBM143b to plasmid pBM169a. However, over-expression of the ACE1 gene from pBM171a compared to pJLin195 in "optimal" medium resulted in a slight decrease in *Thermomyces lanuginosus* variant lipase expression.

TABLE II

| plasmid | wild-type promoter UAS sequences | additional UAS sequences | signal sequence | ACE1 | medium | relative activity |
|---|---|---|---|---|---|---|
| pBM143b | 2 | 0 | wild-type | no | original | 100 |
| pJLin195 | 2 | 0 | variant | no | original | 170 |
| pBM169a | 2 | 0 | wild-type | yes | original | 190 |
| pBM171a | 2 | 0 | variant | yes | original | 402 |
| pBM143b | 2 | 0 | wild-type | no | optimal | 240 |
| pJLin195 | 2 | 0 | variant | no | optimal | 285 |
| pBM169a | 2 | 0 | wild-type | yes | optimal | 318 |
| pBM171a | 2 | 0 | variant | yes | optimal | 266 |

Expression of *Thermomyces lanuginosus* variant lipase from pBM143b, pJLin195, pBM169a, or pBM171a was evaluated in shake flasks. Two representative transformants for each plasmid were grown in duplicate 25 ml shake flask cultures using "original" or "optimal" medium. Shake flask samples were harvested 4, 5, and 6 days. Supernatants from day 5 samples were assayed for *Thermomyces lanuginosus* variant lipase activity using the p-nitrophenyl butyrate assay described above.

In shake flasks, *Thermomyces lanuginosus* variant lipase expression due to the effect of over-expression of the ACE1 gene was approximately 1.1-fold higher when comparing pBM143b to pBM169a in "optimal medium" versus approximately 1.6-fold higher in "original" medium, in addition, over-expression of the ACE1 gene from pBM171a compared to pJLin195 in "original" medium resulted in an approximately 3.5-fold increase in expression, while a 1.6-fold decrease in expression in "optimal" medium was observed as shown in Table III. The relative expression levels of pBM171 transformants in both media were identical, whereas lipase expression levels among pJLin195 transformants were significantly higher in "optimal" medium. Growth was monitored as increasing culture turbidity ($OD_{600}$) and by plating on agar medium to determine total CFU/ml. In general, cells in "original" medium grew at least twice as fast as cells grown in "optimal" medium, presumably due to the preference for glucose as a carbon source. Microscopically, yeast cells grown in "optimal" medium appeared bloated with large vacuoles having increased at least three-fold in size compared to yeast cells grown in "original" medium.

TABLE III

| plasmid | wild-type promoter UAS sequences | additional UAS sequences | signal sequence | ACE1 | medium | relative activity |
|---|---|---|---|---|---|---|
| pBM143b | 2 | 0 | wild-type | no | original | 100 |
| pJLin195 | 2 | 0 | variant | no | original | 162 |
| pBM169a | 2 | 0 | wild-type | yes | original | 162 |
| pBM171a | 2 | 0 | variant | yes | original | 566 |
| pBM143b | 2 | 0 | wild-type | no | optimal | 174 |
| pJLin195 | 2 | 0 | variant | no | optimal | 240 |
| pBM169a | 2 | 0 | wild-type | yes | optimal | 190 |
| pBM171a | 2 | 0 | variant | yes | optimal | 465 |

SDS-PAGE was performed, as described above, on supernatants from representative shake flasks and the intensities of the *Thermomyces lanuginosus* variant lipase bands were consistent with the p-nitrophenyl butyrate assay results.

Plasmids pBM165a and pBM170a were transformed into *Saccharomyces cerevisiae* JG169 cells, as described above. Transformants (24 for each plasmid) were selected and grown in "original" medium in 96-well plates as described above. The results demonstrated that the average relative lipase activities for pBM165a, pBM170a, and pBM169a transformants in "original" medium were 100, 277, and 173, respectively, as shown in Table IV.

TABLE IV

| plasmid | wild-type promoter UAS sequences | additional UAS sequences | signal sequence | ACE1 | medium | relative activity |
|---|---|---|---|---|---|---|
| pBM165a | 2 | 2 | wild-type | no | original | 100 |
| pBM170a | 2 | 2 | wild-type | yes | original | 277 |
| pBM169a | 2 | 0 | wild-type | yes | original | 173 |

By duplicating the primary binding sites for the Ace1p transcription factor and by increasing expression of the ACE1 gene from a multicopy plasmid, a 1.6-fold increase in *Thermomyces lanuginosus* variant lipase expression was observed in 96-well plates.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references including accession numbers are cited herein, the disclosures of which are incorporated by reference in their entireties.

What is claimed is:

1. A method for producing a polypeptide, comprising:
   (a) cultivating a fungal host cell in a medium conducive for the production of the polypeptide, wherein the fungal host cell comprises (i) a first polynucleotide comprising a nucleic acid sequence encoding the polypeptide operably linked to a copper-inducible promoter sequence comprising one or more copper-responsive upstream cis-acting activation sequences activated by a copper-dependent trans-acting transcription factor, (ii) a second polynucleotide comprising one or more additional copper-responsive upstream cis-acting activation sequences operably linked upstream to the promoter sequence, and (iii) a third polynucleotide comprising at least one additional copy of a gene encoding the copper-dependent trans-acting transcription factor; wherein the total number of copper-responsive upstream cis-acting activation sequences in (i) and (ii) is at least 3, and wherein the promoter sequence is foreign to the nucleic acid sequence encoding the polypeptide and the copper-responsive upstream cis-acting activation sequences are responsible for copper-induced transcription of the promoter sequence, and
   (b) isolating the polypeptide from the cultivation medium.

2. The method of claim 1, wherein the copper-inducible promoter sequence is obtained from a gene selected from the group consisting of the *Saccharomyces cerevisiae* metallothienein gene of SEQ ID NO: 1, *Saccharomyces cerevisiae* superoxide dismutase gene of SEQ ID NO: 3, *Saccharomyces cerevisiae* cytosolic catalase gene of SEQ ID NO: 5, *Saccharomyces cerevisiae* copper resistant suppressor gene of SEQ ID NO: 7, *Candida glabrata* metallothionein gene of SEQ ID NO: 9, SEQ ID NO: 11 or SEQ ID NO: 48, *Neurospora crassa* metallothionein gene, *Yarrowia lipolytica* metallothionein gene, *Agaricus bisporus* metallothionein gene, *Magnaporthe grisea* metallothionein gene, and *Podospora anserina* metallothionein gene.

3. The method of claim 1, wherein the one or more additional copper-responsive upstream cis-acting activation sequences are obtained from a gene selected from the group consisting of the Saccharomyces cerevisiae metallothienein gene of SEQ ID NO: 1, *Saccharomyces cerevisiae* superoxide dismutase gene of SEQ ID NO: 3, *Saccharomyces cerevisiae* cytosolic catalase gene of SEQ ID NO: 5, *Saccharomyces cerevisiae* copper resistant suppressor gene of SEQ ID NO: 7, *Candida glabrata* metallothionein gene of SEQ ID NO: 9, SEQ ID NO: 11 or SEQ ID NO: 48, *Neurospora crassa* metallothionein gene, *Yarrowia lipolytica* metallothionein gene, *Agaricus bisporus* metallothionein gene, *Magnaporthe grisea* metallothionein gene, and *Podospora anserina* metallothionein gene, and combinations thereof.

4. The method of claim 1, wherein the one or more additional copper-responsive upstream cis-acting activation sequences are selected from the group consisting of SEQ ID NO: 46 and SEQ ID NO: 47.

5. The method of claim 1, wherein the copper-dependent trans-acting transcription factor gene is selected from the group consisting of the *Saccharomyces cerevisiae* ACE1 gene of SEQ ID NO: 13, *Candida glabrata* AMT1 gene of SEQ ID NO: 15, *Yarrowia lipolytica* CRF1 gene of SEQ ID NO: 17, *Schizosaccharomyces pombe* CUF2 gene of SEQ ID NO: 19, *Saccharomyces cerevisiae* HAA1 gene of SEQ ID NO: 21, and *Aspergillus fumigatus* copper fist DNA binding domain protein gene of SEQ ID NO: 23.

6. The method of claim 1, wherein the fungal host cell contains one or more copies of the first polynucleotide.

7. The method of claim 1, wherein the polypeptide is selected from the group consisting of an antigen, enzyme, growth factor, hormone, immunodilator, neurotransmitter, receptor, reporter protein, structural protein, and transcription factor.

8. The method of claim 1, wherein the polypeptide is an albumin, collagen, tropoelastin, elastin, or gelatin.

9. The method of claim 1, wherein the polypeptide is native or foreign to the fungal host cell.

10. The method of claim 1, wherein the first and second polynucleotides are contained in the chromosome of the fungal host cell or on an extrachromosomal element.

11. The method of claim 1, wherein the third polynucleotide is contained in the chromosome of the fungal host cell or on an extrachromosomal element.

12. The method of claim 1, wherein the fungal host cell is a filamentous fungal or yeast cell.

13. A nucleic acid construct comprising (i) a first polynucleotide comprising a nucleic acid sequence encoding a polypeptide operably linked to a copper-inducible promoter sequence comprising one or more copper-responsive upstream cis-acting activation sequences activated by a copper-dependent trans-acting transcription factor, and (ii) a second polynucleotide comprising one or more additional copper-responsive upstream cis-acting activation sequences operably linked upstream to the promoter sequence, wherein the total number of copper-responsive upstream activation sequences in (i) and (ii) is at least 3, and wherein the promoter sequence is foreign to the nucleic acid sequence encoding the polypeptide and the copper-responsive upstream cis-acting activation sequences are responsible for copper-induced transcription of the promoter.

14. The nucleic acid construct of claim 13, wherein the copper-inducible promoter sequence is obtained from a gene selected from the group consisting of the Saccharomyces cerevisiae metallothienein gene of SEQ ID NO: 1, *Saccharomyces cerevisiae* superoxide dismutase gene of SEQ ID NO: 3, *Saccharomyces cerevisiae* cytosolic catalase gene of SEQ ID NO: 5, *Saccharomyces cerevisiae* copper resistant suppressor gene of SEQ ID NO: 7, *Candida glabrata* metallothionein gene of SEQ ID NO: 9, SEQ ID NO: 11 or SEQ ID NO: 48, *Neurospora crassa* metallothionein gene, *Yarrowia lipolytica* metallothionein gene, *Agaricus bisporus* metallothionein gene, *Magnaporthe grisea* metallothionein gene, and *Podospora anserina* metallothionein gene.

15. The nucleic acid construct of claim 13, wherein the one or more additional copper-responsive upstream cis-acting activation sequences are obtained from a gene selected from the group consisting of the Saccharomyces cerevisiae metallothienein gene of SEQ ID NO: 1, *Saccharomyces cerevisiae* superoxide dismutase gene of SEQ ID NO: 3, *Saccharomyces cerevisiae* cytosolic catalase gene of SEQ ID NO: 5, *Saccharomyces cerevisiae* copper resistant suppressor gene of SEQ ID NO: 7, *Candida glabrata* metallothionein gene of SEQ ID NO: 9, SEQ ID NO: 11 or SEQ ID NO: 48, *Neurospora crassa* metallothionein gene, *Yarrowia lipolytica* metallothionein gene, *Agaricus bisporus* metallothionein gene, *Magnaporthe grisea* metallothionein gene, and *Podospora anserina* metallothionein gene, and combinations thereof.

16. The nucleic acid construct of claim 13, wherein the one or more additional copper-responsive upstream cis-acting activation sequences are selected from the group consisting of SEQ ID NO: 46 and SEQ ID NO: 47.

17. A recombinant expression vector comprising the nucleic acid construct of claim 13.

18. A recombinant fungal host cell comprising the nucleic acid construct of claim 13 and a third polynucleotide comprising at least one additional copy of a gene encoding a copper-dependent trans-acting transcription factor.

19. The recombinant fungal host cell of claim 18, wherein the copper-dependent trans-acting transcription factor gene is selected from the group consisting of the *Saccharomyces cerevisiae* ACE1 gene of SEQ ID NO: 13, *Candida glabrata* AMT1 gene of SEQ ID NO: 15, *Yarrowia lipolytica* CRF1 gene of SEQ ID NO: 17, *Schizosaccharomyces pombe* CUF2 gene of SEQ ID NO: 19, *Saccharomyces cerevisiae* HAA1 gene of SEQ ID NO: 21, and *Aspergillus fumigatus* copper fist DNA binding domain protein gene of SEQ ID NO: 23.

* * * * *

SEQUENCE LISTING

```
<160> NUMBER OF SEQ ID NOS: 48

<210> SEQ ID NO 1
<211> LENGTH: 1183
<212> TYPE: DNA
<213> ORGANISM: Saccharomyces cerevisiae

<400> SEQUENCE: 1
ttattgaaat cttacagaat tttatagcaa tcacatttgc tattttccaa cgttgtgaag      60
taatattata tgacgaattt tacaaaaatc tttcaaatga ggagattaat gttcaattgc     120
tattgattca tgacaagatt ttggaaattt taaaaaaaat agaaattatc gtatcctttt     180
tacgagatga aatgaatagc aacggaagtt tcaaatctat taaggtttc aacaaggttt     240 tgaatctgat taaatatatg ctgagattta gcaagaaaaa acaaaattt gcgagaaact     300
```

```
ctgataacaa taatgttaca gattatagtc agtcggcgaa gaacaaaaat gttctcttga      360
aattccccgt tagtgaactg aacagaatct atttaaaatt taaggagatt tcagattttt      420
taatggaaag agaagttgtc caaaggagta taattattga caaggatttg aatctgata       480 atctgggtat tactacggca aacttcaacg atttctatga tgcattttat aattagtaag      540
ccgatcccat taccgacatt tgggcgctat acgtgcatat gttcatgtat gtatctgtat      600
ttaaaacact tttgtattat ttttcctcat atatgtgtat aggtttatac ggatgattta      660
attattactt caccacccct tatttcaggc tgatatctta gccttgttac tagttagaaa      720
aagacatttt tgctgtcagt cactgtcaag agattctttt gctggcattt cttctagaag      780
caaaaagagc gatgcgtctt ttccgctgaa ccgttccagc aaaaaagact accaacgcaa      840
tatggattgt cagaatcata taaaagagaa gcaaataact ccttgtcttg tatcaattgc      900
attataatat cttcttgtta gtgcaatatc atatagaagt catcgaaata gatattaaga      960
aaaacaaact gtacaatcaa tcaatcaatc atcacataaa atgttcagcg aattaattaa     1020
cttccaaaat gaaggtcatg agtgccaatg ccaatgtggt agctgcaaaa ataatgaaca     1080
atgccaaaaa tcatgtagct gcccaacggg gtgtaacagc gacgacaaat gcccctgcgg     1140
taacaagtct gaagaaacca agaagtcatg ctgctctggg aaa                      1183

<210> SEQ ID NO 2
<211> LENGTH: 61
<212> TYPE: PRT
<213> ORGANISM: Saccharomyces cerevisiae

<400> SEQUENCE: 2

Met Phe Ser Glu Leu Ile Asn Phe Gln Asn Glu Gly His Glu Cys Gln
1               5                   10                  15

Cys Gln Cys Gly Ser Cys Lys Asn Asn Glu Gln Cys Gln Lys Ser Cys
            20                  25                  30

Ser Cys Pro Thr Gly Cys Asn Ser Asp Asp Lys Cys Pro Cys Gly Asn
        35                  40                  45

Lys Ser Glu Glu Thr Lys Lys Ser Cys Cys Ser Gly Lys
    50                  55                  60

<210> SEQ ID NO 3
<211> LENGTH: 873
<212> TYPE: DNA
<213> ORGANISM: Saccharomyces cerevisiae

<400> SEQUENCE: 3
actgcgactc atccatgtga aattatcgga tctgcaaaaa gtttcaactt ccacaggtaa       60
tattggcatg atgccaaatt ggacgtaagc atctctgaag tgcagccgat tggacgtgcg      120
actcacccac tcaggacatg atctcagtag cgggttcgat aaggcgatga cagcgcaaat      180
gccgcttact ggaagtacag aacccgctcc cttaggggca cccacccccag cacgccgggg     240 ggttaaaccg gtgtgtcgga attagtaagc ggacatccct tccgctgggc tcgccatcgc      300
agatatatat ataagaagat ggttttgggc aaatgtttag ctgtaactat gttgcggaaa      360 acagggggcaa gaaagcaatc gcgcaaacaa ataaaacata attaatttat aatggttcaa      420
gcagtcgcag tgttaaaggg tgatgccggt gtctctggtg ttgtcaagtt cgaacaggct      480
tccgaatccg agccaaccac tgtctcttac gagatcgctg gtaacagtcc taacgcagaa      540
cgtgggttcc acattcatga gtttggagat gccaccaatg gttgtgtctc tgctggtcct      600
cacttcaatc ctttcaagaa gacacatggt gctccaactg acgaagtcag acatgtcggt      660
```

```
gacatgggta acgtaaagac ggacgaaaat ggtgtggcca agggctcctt caaggactct    720
ttgatcaagc ttatcggtcc tacctccgtt gtaggcagaa gcgtcgttat ccacgccggc    780
caagatgact taggtaaggg tgacactgaa gaatctttga agactggtaa tgccggtcca    840
agaccagcct gtggtgtcat tggtctaacc aac                                 873

<210> SEQ ID NO 4
<211> LENGTH: 154
<212> TYPE: PRT
<213> ORGANISM: Saccharomyces cerevisiae

<400> SEQUENCE: 4

Met Val Gln Ala Val Ala Val Leu Lys Gly Asp Ala Gly Val Ser Gly
1               5                   10                  15

Val Val Lys Phe Glu Gln Ala Ser Glu Ser Pro Thr Thr Val Ser
            20                  25                  30

Tyr Glu Ile Ala Gly Asn Ser Pro Asn Ala Glu Arg Gly Phe His Ile
        35                  40                  45

His Glu Phe Gly Asp Ala Thr Asn Gly Cys Val Ser Ala Gly Pro His
    50                  55                  60

Phe Asn Pro Phe Lys Lys Thr His Gly Ala Pro Thr Asp Glu Val Arg
65                  70                  75                  80

His Val Gly Asp Met Gly Asn Val Lys Thr Asp Glu Asn Gly Val Ala
                85                  90                  95

Lys Gly Ser Phe Lys Asp Ser Leu Ile Lys Leu Ile Gly Pro Thr Ser
            100                 105                 110

Val Val Gly Arg Ser Val Val Ile His Ala Gly Gln Asp Asp Leu Gly
        115                 120                 125

Lys Gly Asp Thr Glu Glu Ser Leu Lys Thr Gly Asn Ala Gly Pro Arg
    130                 135                 140

Pro Ala Cys Gly Val Ile Gly Leu Thr Asn
145                 150

<210> SEQ ID NO 5
<211> LENGTH: 2309
<212> TYPE: DNA
<213> ORGANISM: Saccharomyces cerevisiae

<400> SEQUENCE: 5
aagtgtgctc atagtatttc gacgttgaag attagggttg caagtccgag aactaaactg     60
ccttcacgac gtcaaactta ttgtatggtg acaataaaac gaattcaaga agccagagat    120
gatgaggaac cgatgacgag gcacatgggg atagaacctc cgttatctcc attccgcgtt    180
gagcagctct cctgcgtgct ttcacagaga ccctaagcca agaccgcgga cggccctctt    240
tttcaagggg atcaccggta aggggccaag cggtgaaatt gcgtattgtt tcctcctttc    300
aatgatgagt acgtcgccga tccagaaggg ttattattgt cattgccagt actattcgta    360
tgctgaaaaa gtatagttca cttcaccctc tggctgcagg ctagcctagc cgataatgcc    420
cccgactccc tcaacaggta gaatttgtaa ggattcgacg tagcctggac acattgtgca    480
tttatcgtat cccctactgc tacacgtata agaagtcgtt gctttacctc tattccagaa    540
ctcaatcttg tcgttacttg cccttattaa aaaaatcctt ctcttgtctc atgccaataa    600
gatcaatcag ctcagcttca caaatgaacg tgttcggtaa aaaagaagaa agcaagaaa     660 aagtttactc tctacaaaac ggttttccgt actctcatca cccatacgct tctcaatact    720
```

```
caagaccaga cggccctatc ttactgcaag acttccatct gctggaaaat atcgcaagtt    780
tcgatagaga aagagttccg gagcgtgtag tccatgccaa aggtggtggt tgtagactgg    840
agttcgaact aacagattct tgagtgata  ttacatacgc cgctccatac agaatgtgg     900 gttacaaatg tcctggtctt gttcgttttt ccaccgttgg tggtgaaagt ggtacaccag    960
acactgcaag agacccaaga ggtgtttctt ttaaattcta taccgagtgg gggaaccatg   1020
actgggtctt caacaatact cccgtcttct cctcagaga  cgctattaag tttcccgtat   1080
ttattcattc gcaaaagaga gaccctcagt ctcatctgaa tcagtttcag gacactacca   1140
tatactggga ttatctaaca ttgaatccgg aatcaatcca tcaaataact acatgtttg    1200 gtgatagagg tactcctgct tcgtgggcta gtatgaacgc gtactctggt cattccttca   1260
tcatggtcaa caagaaggt  aaggacacat atgtgcaatt ccacgtcttg tcggatactg   1320
gttttgaaac cttgactgga gataaggctg ctgaactgtc aggctcccac cctgattata   1380
atcaggcaaa gctgttcact caattgcaaa atggcgaaaa gccaaaattt aactgttatg   1440
tgcaaacaat gacacccgaa caagcaacta agttcaggta ttcggtaaat gacctaacga   1500
aaatatggcc acacaaggaa ttcccttga  gaaaatttgg taccatcacc ctaacggaga   1560
atgttgacaa ttatttccaa gaaattgaac aagttgcatt cagtccaacg aacacttgta   1620
tcccaggtat taagccttct aatgattccg ttctacaagc cagacttttc tcctatccag   1680
acactcaacg tcatagattg ggagccaact atcagcaatt gcccgtcaac agaccaagaa   1740
acttgggatg tccatactcc aaaggtgatt cccaatacac tgccgaacag tgtccattta   1800
aagcagtgaa cttccaaagg gacggcccaa tgagttacta caatttcggt cctgagccaa   1860
attatatttc cagtttacca aatcaaactc tgaaattcaa aaatgaagtc aacgacgaag   1920
tatctgataa gttcaaaggg atagttcttg acgaagtaac agaagtttct gtgagaaaac   1980
aggaacaaga ccaaatcaga acgagcata  ttgttgatgc caaaattaat caatattact   2040
acgtttatgg tattagtcca ctagacttcg aacagccaag agctctatat gaaaaggtat   2100
acaacgatga acagaagaaa ttattcgttc ataacgttgt ttgccacgct tgtaagatca   2160
aagatcctaa agtcaaaaag agagttacgc aatactttgg tttgctaaac gaagatttgg   2220
gtaaagtcat tgcagaaggc ttgggagttc cttgggaacc tgttgacctt gaaggttatg   2280
ccaagacttg gtccattgca agtgccaat                                     2309
```

<210> SEQ ID NO 6
<211> LENGTH: 562
<212> TYPE: PRT
<213> ORGANISM: Saccharomyces cerevisiae

<400> SEQUENCE: 6

```
Met Asn Val Phe Gly Lys Lys Glu Glu Lys Gln Glu Lys Val Tyr Ser
1               5                   10                  15

Leu Gln Asn Gly Phe Pro Tyr Ser His His Pro Tyr Ala Ser Gln Tyr
            20                  25                  30

Ser Arg Pro Asp Gly Pro Ile Leu Leu Gln Asp Phe His Leu Leu Glu
        35                  40                  45

Asn Ile Ala Ser Phe Asp Arg Glu Arg Val Pro Glu Arg Val Val His
    50                  55                  60

Ala Lys Gly Gly Gly Cys Arg Leu Glu Phe Glu Leu Thr Asp Ser Leu
65                  70                  75                  80

Ser Asp Ile Thr Tyr Ala Ala Pro Tyr Gln Asn Val Gly Tyr Lys Cys
                85                  90                  95
```

```
Pro Gly Leu Val Arg Phe Ser Thr Val Gly Gly Glu Ser Gly Thr Pro
            100                 105                 110

Asp Thr Ala Arg Asp Pro Arg Gly Val Ser Phe Lys Phe Tyr Thr Glu
            115                 120                 125

Trp Gly Asn His Asp Trp Val Phe Asn Thr Pro Val Phe Phe Leu
            130                 135                 140

Arg Asp Ala Ile Lys Phe Pro Val Phe Ile His Ser Gln Lys Arg Asp
145                 150                 155                 160

Pro Gln Ser His Leu Asn Gln Phe Gln Asp Thr Thr Ile Tyr Trp Asp
            165                 170                 175

Tyr Leu Thr Leu Asn Pro Glu Ser Ile His Gln Ile Thr Tyr Met Phe
            180                 185                 190

Gly Asp Arg Gly Thr Pro Ala Ser Trp Ala Ser Met Asn Ala Tyr Ser
            195                 200                 205

Gly His Ser Phe Ile Met Val Asn Lys Glu Gly Lys Asp Thr Tyr Val
            210                 215                 220

Gln Phe His Val Leu Ser Asp Thr Gly Phe Glu Thr Leu Thr Gly Asp
225                 230                 235                 240

Lys Ala Ala Glu Leu Ser Gly Ser His Pro Asp Tyr Asn Gln Ala Lys
            245                 250                 255

Leu Phe Thr Gln Leu Gln Asn Gly Glu Lys Pro Lys Phe Asn Cys Tyr
            260                 265                 270

Val Gln Thr Met Thr Pro Glu Gln Ala Thr Lys Phe Arg Tyr Ser Val
            275                 280                 285

Asn Asp Leu Thr Lys Ile Trp Pro His Lys Glu Phe Pro Leu Arg Lys
            290                 295                 300

Phe Gly Thr Ile Thr Leu Thr Glu Asn Val Asp Asn Tyr Phe Gln Glu
305                 310                 315                 320

Ile Glu Gln Val Ala Phe Ser Pro Thr Asn Thr Cys Ile Pro Gly Ile
            325                 330                 335

Lys Pro Ser Asn Asp Ser Val Leu Gln Ala Arg Leu Phe Ser Tyr Pro
            340                 345                 350

Asp Thr Gln Arg His Arg Leu Gly Ala Asn Tyr Gln Gln Leu Pro Val
            355                 360                 365

Asn Arg Pro Arg Asn Leu Gly Cys Pro Tyr Ser Lys Gly Asp Ser Gln
            370                 375                 380

Tyr Thr Ala Glu Gln Cys Pro Phe Lys Ala Val Asn Phe Gln Arg Asp
385                 390                 395                 400

Gly Pro Met Ser Tyr Tyr Asn Phe Gly Pro Glu Pro Asn Tyr Ile Ser
            405                 410                 415

Ser Leu Pro Asn Gln Thr Leu Lys Phe Lys Asn Glu Val Asn Asp Glu
            420                 425                 430

Val Ser Asp Lys Phe Lys Gly Ile Val Leu Asp Glu Val Thr Glu Val
            435                 440                 445

Ser Val Arg Lys Gln Glu Gln Asp Gln Ile Arg Asn Glu His Ile Val
            450                 455                 460

Asp Ala Lys Ile Asn Gln Tyr Tyr Val Tyr Gly Ile Ser Pro Leu
465                 470                 475                 480

Asp Phe Glu Gln Pro Arg Ala Leu Tyr Glu Lys Val Tyr Asn Asp Glu
            485                 490                 495

Gln Lys Lys Leu Phe Val His Asn Val Val Cys His Ala Cys Lys Ile
            500                 505                 510
```

```
Lys Asp Pro Lys Val Lys Lys Arg Val Thr Gln Tyr Phe Gly Leu Leu
            515                 520                 525

Asn Glu Asp Leu Gly Lys Val Ile Ala Glu Gly Leu Gly Val Pro Trp
        530                 535                 540

Glu Pro Val Asp Leu Glu Gly Tyr Ala Lys Thr Trp Ser Ile Ala Ser
545                 550                 555                 560

Ala Asn

<210> SEQ ID NO 7
<211> LENGTH: 1104
<212> TYPE: DNA
<213> ORGANISM: Saccharomyces cerevisiae

<400> SEQUENCE: 7
ggatcccctt cacccacctg gaaatctcca atcgaaagaa taagggacag aagaagaaga      60
cataagataa tgaaaagtga gaataaattt gggcaaaatc ccagttttgg aagtaaatcg     120
aatggcaaac ctaatactaa aacgacatta tccaaatatc gacagctatt aaggaagcct     180
aggcgaaaaa ccaattcata tgaaccaaaa aatggcattg gacagaataa agaaggctca     240
actgttagac caggagccga caaacatatt agagattcca attatctagc tacagacatc     300
agtgacaacg aaagtatgga aaccgaactt cgaaccaacc acatttataa ttacgaaaat     360
agtgattaag gcaggcccag tggacgaaaa gacataactg cagaagtaca gctgccttta     420
tttcttgtgg tcatttattg cttttatttt caagtcagat atacaagaaa atcaaatccc     480
atcgtcaacg tcacgtataa acgattaatt tacagtaata ccatactcta ccaacattat     540
tttagtccga cgttcagtcc tgtaggtgtt ccaaatcctt ctggcattga cttctgtgca     600
gaaacccttc aaaatgagtt ccactttacg tcagatcgca taacaaccgg tcatatattt     660 ttttctttg ctaaaccccc tactgcaagc acttttaaga aaagaacaa taaatgcgtc     720 tttattgctg tgtggaagtg attttttgtct ttcggacaaa aaaaggatag ggatgcgaga     780
gggctgtgaa gtagtgatca agcggggcct atataagaag ggcgcacatc gtccccccta     840
agaatagcga agcgatatta cactgaacac tacaatgtca aatagtactc aataaatatg     900
actgtaaaaa tatgtgactg tgaaggcgaa tgttgtaagg actcttgtca ttgtgggagc     960
acctgccttc caagctgttc tggcggtgaa aagtgcaaat gtgatcacag caccggaagc    1020
cctcaatgta agagttgtgg tgaaaaatgc aaatgcgaaa ccacgtgcac ttgtgaaaag    1080
agtaaatgca attgtgaaaa atgt                                          1104

<210> SEQ ID NO 8
<211> LENGTH: 69
<212> TYPE: PRT
<213> ORGANISM: Saccharomyces cerevisiae

<400> SEQUENCE: 8

Met Thr Val Lys Ile Cys Asp Cys Glu Gly Glu Cys Cys Lys Asp Ser
1               5                   10                  15

Cys His Cys Gly Ser Thr Cys Leu Pro Ser Cys Ser Gly Gly Glu Lys
                20                  25                  30

Cys Lys Cys Asp His Ser Thr Gly Ser Pro Gln Cys Lys Ser Cys Gly
            35                  40                  45

Glu Lys Cys Lys Cys Glu Thr Thr Cys Thr Cys Glu Lys Ser Lys Cys
        50                  55                  60

Asn Cys Glu Lys Cys
65
```

<210> SEQ ID NO 9
<211> LENGTH: 503
<212> TYPE: DNA
<213> ORGANISM: Candida glabrata

<400> SEQUENCE: 9

```
gaattccgcc cttcatacac atcctacact cccttaagga gggaagtaca aacaagtgtt    60
cgcccattct cttctctcat gatgtgtaaa gaaaagtgaa atcagcaat aatagcttct    120
gactatgact atctgtattg acagcaataa tagctttcgg gatagcatgc aaaaaaaaaa    180
tttatatata aacagaggtc tttttgaaat gttagatcaa tttctaatta aacattttgt    240
agatcctaca taactcatac aacaaacaac aaacaacaaa caacaaacaa caaacacata    300
caaaaacaaa cacaatggct aacgattgca aatgtcctaa cggttgctcc tgtccaaact    360
gcgccaacgg tggctgccag tgcggtgaca agtgcgagtg caagaagcag agctgtcacg    420
gctgcggtga acaatgcaag tgcggttccc acggttccag ctgtcacggt tcttgtggat    480
gcggtgacaa gtgtgagtgc aag                                            503
```

<210> SEQ ID NO 10
<211> LENGTH: 63
<212> TYPE: PRT
<213> ORGANISM: Candida glabrata

<400> SEQUENCE: 10

Met Ala Asn Asp Cys Lys Cys Pro Asn Gly Cys Ser Cys Pro Asn Cys
1               5                   10                  15

Ala Asn Gly Gly Cys Gln Cys Gly Asp Lys Cys Glu Cys Lys Lys Gln
            20                  25                  30

Ser Cys His Gly Cys Gly Glu Gln Cys Lys Cys Gly Ser His Gly Ser
        35                  40                  45

Ser Cys His Gly Ser Cys Gly Cys Gly Asp Lys Cys Glu Cys Lys
    50                  55                  60

<210> SEQ ID NO 11
<211> LENGTH: 265
<212> TYPE: DNA
<213> ORGANISM: Candida glabrata

<400> SEQUENCE: 11

```
gaattcattt ctcccattta tcctttcttc tatatatcga atcaacacat caacaatacc    60
aacaaacttc aacttataca caacatctaa tatttattat agcttcgaaa tgcctgaaca   120
agtcaactgc caatacgatt gccactgctc caactgtgct tgtgaaaata cttgcaactg   180
ctgtgccaag ccagcatgtg cttgcacaaa ctctgcttcc aatgaatgct cctgccaaac   240
ttgcaagtgt caaacatgca agtgc                                         265
```

<210> SEQ ID NO 12
<211> LENGTH: 52
<212> TYPE: PRT
<213> ORGANISM: Candida glabrata

<400> SEQUENCE: 12

Met Pro Glu Gln Val Asn Cys Gln Tyr Asp Cys His Cys Ser Asn Cys
1               5                   10                  15

Ala Cys Glu Asn Thr Cys Asn Cys Cys Ala Lys Pro Ala Cys Ala Cys
            20                  25                  30

Thr Asn Ser Ala Ser Asn Glu Cys Ser Cys Gln Thr Cys Lys Cys Gln
        35                  40                  45

Thr Cys Lys Cys
    50

<210> SEQ ID NO 13
<211> LENGTH: 870
<212> TYPE: DNA
<213> ORGANISM: Saccharomyces cerevisiae

<400> SEQUENCE: 13
gatcgtgaaa gaatatttgc taagaaaatc gccaaaacga ggcgaagtcg cagggtgcgc      60
gggcacgcag ggtaagagcc gcaaggcctg gttcggtaag tattaagctg tggacgaaat     120
agcagtagcc atggcgatgt aatttattag acggcggctt gataaaagag gactgataat     180
cagtgtattc acagaatggt cgtaattaac ggggtcaaat atgcctgtga acgtgtatc      240 aggggtcaca gggcggcgca gtgtactcac actgatggtc cgctacagat gatcagacgc     300
aagggaagac catcgaccac atgtggccat tgtaaagagc tgagaagaac caagaacttc     360
aacccatccg gtgggtgcat gtgtgcctct gcacgacggc cagctgttgg cagcaaggaa     420
gatgaaacac gatgtcgttg tgatgagggt gaaccttgta aatgtcatac caagaggaaa     480
agcagccgga aatcaaaggg agggtcatgc cacagaaggg caaatgatga agcagcgcat     540
gtcaatggtc tcggtattgc agatctggac gttcttttgg gcctaaatgg tcgctcgtcg     600
gatgtagaca tgacaaccac attgccgagt ttgaagccac ctctgcaaaa cggagaaatt     660
aaggccgaca gcattgacaa tcttgatttg gcttccctcg atccgcttga gcaaagccct     720
agtatatcta tggaacctgt tagtatcaat gaaacaggaa gcgcatatac aactacgaac     780
acagcactaa acgatattga cattccattc tccatcaatg agttgaacga gctatacaaa     840
caagtatctt cgcataactc acattcacaa                                      870

<210> SEQ ID NO 14
<211> LENGTH: 225
<212> TYPE: PRT
<213> ORGANISM: Saccharomyces cerevisiae

<400> SEQUENCE: 14

Met Val Val Ile Asn Gly Val Lys Tyr Ala Cys Glu Thr Cys Ile Arg
1               5                   10                  15

Gly His Arg Ala Ala Gln Cys Thr His Thr Asp Gly Pro Leu Gln Met
            20                  25                  30

Ile Arg Arg Lys Gly Arg Pro Ser Thr Thr Cys Gly His Cys Lys Glu
        35                  40                  45

Leu Arg Arg Thr Lys Asn Phe Asn Pro Ser Gly Gly Cys Met Cys Ala
    50                  55                  60

Ser Ala Arg Arg Pro Ala Val Gly Ser Lys Glu Asp Glu Thr Arg Cys
65                  70                  75                  80

Arg Cys Asp Glu Gly Glu Pro Cys Lys Cys His Thr Lys Arg Lys Ser
                85                  90                  95

Ser Arg Lys Ser Lys Gly Gly Ser Cys His Arg Arg Ala Asn Asp Glu
            100                 105                 110

Ala Ala His Val Asn Gly Leu Gly Ile Ala Asp Leu Asp Val Leu Leu
        115                 120                 125

Gly Leu Asn Gly Arg Ser Ser Asp Val Asp Met Thr Thr Thr Leu Pro
    130                 135                 140

Ser Leu Lys Pro Pro Leu Gln Asn Gly Glu Ile Lys Ala Asp Ser Ile
145                 150                 155                 160

Asp Asn Leu Asp Leu Ala Ser Leu Asp Pro Leu Glu Gln Ser Pro Ser
            165                 170                 175

Ile Ser Met Glu Pro Val Ser Ile Asn Glu Thr Gly Ser Ala Tyr Thr
            180                 185                 190

Thr Thr Asn Thr Ala Leu Asn Asp Ile Asp Ile Pro Phe Ser Ile Asn
        195                 200                 205

Glu Leu Asn Glu Leu Tyr Lys Gln Val Ser Ser His Asn Ser His Ser
    210                 215                 220

Gln
225

<210> SEQ ID NO 15
<211> LENGTH: 1305
<212> TYPE: DNA
<213> ORGANISM: Candida glabrata

<400> SEQUENCE: 15
agatctcatt agtaaaagtg gggtgttcat caagtgagcc aatgcaagtt tgcgtttctc      60
ttacaggagc ccgatgaatt actggggtag ttgctgttgc catcccctt tgccaccatt     120 cacgtcctgg ttagctactt gtatcctgca ttatttgcgg gcaagtttcc aatactattt     180
gaattataga atacgtcatt ttctcagtgg cactcggaga ctaacattct gaaaaaaaaa     240
aaaaaaatca tgataagcta atttggctga cttaaaagta gtggtgggcg tgatgagccc     300
agtgtttagt ccatttttatg gataatattg atctttaaag gcaagtagtt gaatttctat     360
ttggataaaa ggtataaata gtagttgaga atccagacaa agcacctta tattgaagat     420 aatagcgtta cattatatat aagaagcgat aacaacaaaa acaataggca tatataaagc     480
agagagcaca gcagtacaca catttgcagt atggtagtaa tcaacggggt gaagtatgcc     540
tgtgattcat gcatcaaatc acataaagca gcccagtgtg agcataacga tagacccttta    600 aagatactaa agccaagggg aaggccaccg acgacctgcg accattgcaa agatatgaga    660
aagactaaga atgtgaaccc ttcaggaagt tgtaactgta gtaaactcga aaaataagg    720 caagagaaag gcataacgat agaagaggat atgttgatga gcggaaacat ggacatgtgc    780
ttgtgtgtta gaggtgagcc ttgtaggtgt cacgctagga ggaaaaggac acagaaatca    840
aacaaaaaag ataacttaag cattaattcg cccacaaata attctccttc accagcgctc    900
tctgtgaata ttggagggat ggtggtggct aatgatgaca tcctaaaatc attgggacca    960
attcaaaatg tcgatctaac ggctccacta gattttccac cgaatgggat agataataaa   1020
ccgatggaaa gtttctatac acaaacttct aaatccgatg ctgttgattc gcttgaattc   1080
gatcatctaa tgaatatgca aatgaggaat gataactccc tttcatttcc tatgtctgca   1140
aaccagaatg aagtcggtta tcaatttaat aatgaaggga ataactcaat gaattcaaca   1200
atgaaaaata ctattactca aatggatcaa ggtaattcac atagcatgac cttacacgat   1260
atagacgaaa ttctcaataa cggtattgaa cttggtaatg taaat                   1305

<210> SEQ ID NO 16
<211> LENGTH: 225
<212> TYPE: PRT
<213> ORGANISM: Candida glabrata

<400> SEQUENCE: 16

Met Val Val Ile Asn Gly Val Lys Tyr Ala Cys Glu Thr Cys Ile Arg

```
                1               5                  10                 15
        Gly His Arg Ala Ala Gln Cys Thr His Thr Asp Gly Pro Leu Gln Met
                            20                  25                  30

Ile Arg Arg Lys Gly Arg Pro Ser Thr Thr Cys Gly His Cys Lys Glu
                        35                  40                  45

Leu Arg Arg Thr Lys Asn Phe Asn Pro Ser Gly Gly Cys Met Cys Ala
                50                  55                  60

Ser Ala Arg Arg Pro Ala Val Gly Ser Lys Glu Asp Glu Thr Arg Cys
        65                  70                  75                  80

Arg Cys Asp Glu Gly Glu Pro Cys Lys Cys His Thr Lys Arg Lys Ser
                            85                  90                  95

Ser Arg Lys Ser Lys Gly Gly Ser Cys His Arg Arg Ala Asn Asp Glu
                        100                 105                 110

Ala Ala His Val Asn Gly Leu Gly Ile Ala Asp Leu Asp Val Leu Leu
                    115                 120                 125

Gly Leu Asn Gly Arg Ser Ser Asp Val Asp Met Thr Thr Thr Leu Pro
        130                 135                 140

Ser Leu Lys Pro Pro Leu Gln Asn Gly Glu Ile Lys Ala Asp Ser Ile
        145                 150                 155                 160

Asp Asn Leu Asp Leu Ala Ser Leu Asp Pro Leu Glu Gln Ser Pro Ser
                            165                 170                 175

Ile Ser Met Glu Pro Val Ser Ile Asn Glu Thr Gly Ser Ala Tyr Thr
                        180                 185                 190

Thr Thr Asn Thr Ala Leu Asn Asp Ile Asp Ile Pro Phe Ser Ile Asn
                    195                 200                 205

Glu Leu Asn Glu Leu Tyr Lys Gln Val Ser Ser His Asn Ser His Ser
            210                 215                 220

Gln
        225

<210> SEQ ID NO 17
<211> LENGTH: 2694
<212> TYPE: DNA
<213> ORGANISM: Yarrowia lipolytica

<400> SEQUENCE: 17
atcgattatg tttgaaatgt cctgtagaga cgcatctgag ccgttattcg aggggtctaa      60
gtagctgaca tttcgatccc gtgcaggatg cattctctag ggtcggattt ttttattttt    120
ttattttttt attttttat ttttatttta ctttatctt tgttttgtt tttattttg        180 tttttgtttt tattttatt taattatttt ttattttctg cttgttatac tgtgatttct    240
atttctattt tgatttctga ttttcaatt ttatattccg gagatacgga gttatcggac    300
cctgacagat tgcttcggtg catggactgt atgcacgttg tggtgtctag acagtggcag    360
taattaatta atacaaagtc gaggggatgg gagagtggtc gggaggtcgg gaggtcgagt    420
tctggacttt gtgtgaaaag gtggaaagcg gaagtaggac atgattggag gtgattggag    480
atgatgggat gtgaaattag gagaaaaagg gagaaaaaaa caataaaaag gagaaaaaga    540
caataaaaag gagaaaaaga caataaaaag gagaaaaag accataaaga cagcaaaaaa    600
cagtaaataa cgacaactac ggagaatcac aaaggatgtg gtcatcaagt gagatggtga    660
gtgcgaatat aaatgtgagt gtctatggta cgagttggtg ccagttactg tctgaattca    720
aggcactggc aaaaacccca ttcacccgct catcctctga cgaaacgcca ttcaccaact    780
tcattcacca ctccaaaacc tcaacgttaa ctccgagctc gctttgctcg ctcttaggtt    840
```

-continued

```
gaaaactttt gttggattct tttttgcactt ttcgttttgc ccattttttcg tttttgcactt    900 ttccaaagcc tatataaatg gttggactcg ccctaaggtt agagtgggag tgcaggctcc     960 cttttttcatt tcgagcttat gtgcatttgg cctttgtgtc aagttcagaa gcattcgttc   1020
ccaacttagc ccgctcaccc agtatatata cctgcgccag cgaaccacac cgtcaacgat   1080
cagtcagtac gtcattgagt gcacccagca gcagcgtcag accagcagca gtgtcagcca   1140
acagcccaga ccaccagcaa caacattgac agtgacattg acagtgacag tttcagttac   1200
agtgacagct acagtgatac agacagttac accatcgctc cattgacact actgtttgaa   1260
tagttcacca tcaacttctc caaaggcata gcttcgattt gccaccgatt gcgacattct   1320
gattacattg tttgtgacaa gtggacaacc agacacccat cgcagcactc cactaacacc   1380
tccgccacaa ccaccacaac caccacaacc accaacaa gactcttcgt ctcaactcgt   1440
cttcgactaa tcttactcac aatggtagtc atcgaaggaa tcaaatacgc atgcgaacga   1500
tgcatccgcg gccaccgagt gtcgtcgtgc acacacaccc aacagccgtt gatccggatc   1560
aagcccaagg gacgacccgc tacccagtgt ctgcattgtc gagaggcccg caaaaacaag   1620
gcactccacg tcaagtgcaa atgtggctcc tcgtccagta aacacgccgc cacctgcccc   1680
tgctactcgg gcggaggctg catctgcacc aacaaacacc cccaggtgct gcctcccaac   1740
tccaccacca ctggcgccaa cggctgcatc gttatcaaca aggccgtcct cgacgagggc   1800
tcccagcagc aggcccagca ggctcagcag cagtcgcagt ctcagcaggc ccagcagcag   1860
cagcagcagc cccagcccca ggcttctccc atcctgcaac agcccagat gcccacaccc   1920 gtgcacacta ctaacgtgac cacacctccc gtggccacgc cgacacactc gcaccgggcc   1980
ctgtcgacca caccatcgtt atctcctcaa ccacaatcgc cccactcacc ggagagcgcc   2040
ctcaagtcgg tcaacttctt gggccgaaca aactcgtcgt catccctgtc gtcgttgcac   2100
tcgggccgaa acaagaaccg gatcgaaaag gtgcgaccctt cgcataactc gctgagtgcc   2160
gcctcccagc tggccaactc gccgtcatcg ccgttctacg ccgtgacgcc acccgcctgg   2220
gtcgactccc ccaccctggt gcctaccggt gccctcgacg cctcgtacct ccagatcctc   2280
aacgatgacc tttcgtcgcc gctgctggac tcggacgtgt tctcgtcgct tgacatggag   2340
cccgtggcgc attccaacaa caaccacgga ggcatcccta ccggcggctc tcgtgccctc   2400
gcatctacag acattaactt tgaccggttc gagtccacct cgccgtcgtc gattctgtcg   2460
tcgtggaacc tttggggtgg tgtcggtggc agtgatgcgc ccgagatgag cgtggctgcc   2520
aacccgtcgg catcggcatc ggcctccagc atccagaccc ctcccagcag caacgccacg   2580
ccggagtggg tccagggcca gcaacagcct tgctcggtgt ccccggcaga cgtcatgctg   2640
cctttcaaga gggatgatca ggagagcgtg tttttgacgg agccgttgta tctt         2694
```

<210> SEQ ID NO 18
<211> LENGTH: 411
<212> TYPE: PRT
<213> ORGANISM: Yarrowia lipolytica

<400> SEQUENCE: 18

Met Val Val Ile Glu Gly Ile Lys Tyr Ala Cys Glu Arg Cys Ile Arg
1               5                   10                  15

Gly His Arg Val Ser Ser Cys Thr His Thr Gln Gln Pro Leu Ile Arg
            20                  25                  30

Ile Lys Pro Lys Gly Arg Pro Ala Thr Gln Cys Leu His Cys Arg Glu
        35                  40                  45

Ala Arg Lys Asn Lys Ala Leu His Val Lys Cys Lys Cys Gly Ser Ser
 50                  55                  60

Ser Ser Lys His Ala Ala Thr Cys Pro Cys Tyr Ser Gly Gly Gly Cys
 65                  70                  75                  80

Ile Cys Thr Asn Lys His Pro Gln Val Leu Pro Pro Asn Ser Thr Thr
                 85                  90                  95

Thr Gly Ala Asn Gly Cys Ile Val Ile Asn Lys Ala Val Leu Asp Glu
            100                 105                 110

Gly Ser Gln Gln Gln Ala Gln Gln Ala Gln Gln Ser Gln Ser Gln
        115                 120                 125

Gln Ala Gln Gln Gln Gln Gln Pro Gln Pro Gln Ala Ser Pro Ile
    130                 135                 140

Leu Gln Gln Pro Gln Met Pro Thr Pro Val His Thr Thr Asn Val Thr
145                 150                 155                 160

Thr Pro Pro Val Ala Thr Pro Thr His Ser His Arg Ala Leu Ser Thr
                165                 170                 175

Thr Pro Ser Leu Ser Pro Gln Pro Gln Ser Pro His Ser Pro Glu Ser
                180                 185                 190

Ala Leu Lys Ser Val Asn Phe Leu Gly Arg Thr Asn Ser Ser Ser Ser
            195                 200                 205

Leu Ser Ser Leu His Ser Gly Arg Asn Lys Asn Arg Ile Glu Lys Val
210                 215                 220

Arg Pro Ser His Asn Ser Leu Ser Ala Ala Ser Gln Leu Ala Asn Ser
225                 230                 235                 240

Pro Ser Ser Pro Phe Tyr Ala Val Thr Pro Pro Ala Trp Val Asp Ser
                245                 250                 255

Pro Thr Leu Val Pro Thr Gly Ala Leu Asp Ala Ser Tyr Leu Gln Ile
            260                 265                 270

Leu Asn Asp Asp Leu Ser Ser Pro Leu Leu Asp Ser Asp Val Phe Ser
        275                 280                 285

Ser Leu Asp Met Glu Pro Val Ala His Ser Asn Asn Asn His Gly Gly
    290                 295                 300

Ile Pro Thr Gly Gly Ser Arg Ala Leu Ala Ser Thr Asp Ile Asn Phe
305                 310                 315                 320

Asp Arg Phe Glu Ser Thr Ser Pro Ser Ser Ile Leu Ser Ser Trp Asn
                325                 330                 335

Leu Trp Gly Gly Val Gly Gly Ser Asp Ala Pro Glu Met Ser Val Ala
            340                 345                 350

Ala Asn Pro Ser Ala Ser Ala Ser Ser Ile Gln Thr Pro Pro
        355                 360                 365

Ser Ser Asn Ala Thr Pro Glu Trp Val Gln Gly Gln Gln Gln Pro Cys
    370                 375                 380

Ser Val Ser Pro Ala Asp Val Met Leu Pro Phe Lys Arg Asp Asp Gln
385                 390                 395                 400

Glu Ser Val Phe Leu Thr Glu Pro Leu Tyr Leu
                405                 410

<210> SEQ ID NO 19
<211> LENGTH: 531
<212> TYPE: DNA
<213> ORGANISM: Schizosaccharomyces pombe

<400> SEQUENCE: 19
atgatcatta ttgacggtaa gaattatgct tgtgttgtat gccttcgagg tcatcgaggc    60

| | |
|---|---|
| tcatcctgcc agcatcaaga aagggcactg atagaagttc gaactagagg aaggccgtta | 120 |
| ctatgcaaaa aatgcagagc cataaaacaa caacttaaga gtaatttaaa atgcgtttgt | 180 |
| catttgcagc cttttctacc cttcgccaat gagtatcagg agttattaaa tttcactcag | 240 |
| aaaaacccaa tattggctag cctttttttg ttttcaaccg acaaagatat tatgaattct | 300 |
| tctttaaatc ctgcaagtca agcctacacc ttcgatttag gaagaacact acccatcagt | 360 |
| gaagatatat taggatatag gaaacctctt tcactaacag atgcttctaa tcgcattgat | 420 |
| gcaagtcaat tgaatgaaaa agaaaacgat tcttttacca taaaccaaga ggccgatatt | 480 |
| ttcaatttcg caaagtactt acattccaaa gacgatatat ccggaatccc t | 531 |

<210> SEQ ID NO 20
<211> LENGTH: 177
<212> TYPE: PRT
<213> ORGANISM: Schizosaccharomyces pombe

<400> SEQUENCE: 20

Met Ile Ile Ile Asp Gly Lys Asn Tyr Ala Cys Val Val Cys Leu Arg
1               5                   10                  15

Gly His Arg Gly Ser Ser Cys Gln His Gln Glu Arg Ala Leu Ile Glu
            20                  25                  30

Val Arg Thr Arg Gly Arg Pro Leu Leu Cys Lys Lys Cys Arg Ala Ile
        35                  40                  45

Lys Gln Gln Leu Lys Ser Asn Leu Lys Cys Val Cys His Leu Gln Pro
    50                  55                  60

Phe Leu Pro Phe Ala Asn Glu Tyr Gln Glu Leu Asn Phe Thr Gln
65                  70                  75                  80

Lys Asn Pro Ile Leu Ala Ser Leu Phe Leu Phe Ser Thr Asp Lys Asp
                85                  90                  95

Ile Met Asn Ser Ser Leu Asn Pro Ala Ser Gln Ala Tyr Thr Phe Asp
            100                 105                 110

Leu Gly Arg Thr Leu Pro Ile Ser Glu Asp Ile Leu Gly Tyr Arg Lys
        115                 120                 125

Pro Leu Ser Leu Thr Asp Ala Ser Asn Arg Ile Asp Ala Ser Gln Leu
    130                 135                 140

Asn Glu Lys Glu Asn Asp Ser Phe Thr Ile Asn Gln Glu Ala Asp Ile
145                 150                 155                 160

Phe Asn Phe Ala Lys Tyr Leu His Ser Lys Asp Asp Ile Ser Gly Ile
                165                 170                 175

Pro

<210> SEQ ID NO 21
<211> LENGTH: 2082
<212> TYPE: DNA
<213> ORGANISM: Saccharomyces cerevisiae

<400> SEQUENCE: 21

| | |
|---|---|
| atggtcttga taaatggcat aaagtatgcc tgtgagaggt gcataagagg ccatagagta | 60 |
| acaacatgca atcatacaga tcaaccgctt atgatgatca aacccaaagg tagaccttcc | 120 |
| actacatgcg actattgtaa acaacttcga aaaaacaaga atgcaaatcc tgaaggtgtt | 180 |
| tgcacgtgtg ccggctaga gaagaaaaaa ctggcacaga aagccaaaga agaagcaaga | 240 |
| gctaaagcca agaaaaaca agaaaacag tgtacctgcg ggactgatga ggtttgcaaa | 300 |
| tatcatgctc aaaagagaca tctaagaaag tccccttcaa gttctcaaaa gaaaggaaga | 360 |

-continued

```
tccatttctc gttctcaacc aatgtttgaa agggtattgt cttctacttc acttgacagc    420
aatatgttat ccggccacgg agcactatca gatacctcta gcatactgac gagcacattt    480
ttagacagtg agccgggtgt tggtaaaatt tcaaaagatt accatcatgt cccttcattg    540
gcctccattt catccttaca atcctcgcaa tcgttagatc aaaatttcag tataccacaa    600
agcccgccgt tatcttcaat gtcatttaat tttctcacgg aaatatcaa tgaaaccaac     660 caaaatcaca gtaatcatca gcattcaaaa tcaggcaata actggcaaga tagttcggta    720
agcttgccag cgaaagctga ttcacgtctt aacatgatgg ataaaaacaa ctctgtgggt    780
cttgacctat taggccattc aaaacgaata tcgccgatat caaactctcg tgtgggcgaa    840
gttagcgttc cgctagaaga atatattcct tctgacattg atggggttgg aagagttact    900
gataaaagct ctttggtcta cgattggcca tttgatgaaa gtattgagag aaatttcagt    960
acaaccgcaa ccgctgcaac tggtgaaagt aagttcgaca ttaacgacaa ctgtaataga   1020
attaatagca aaagttatag taagactaat agtatgaatg gaaacggtat gaacaatagc   1080
aataataata atatcaacag taatggcaac gacaagaaca ataacaactc ttctagacaa   1140
gaacatcaag gaaatggact atttgacatg tttacagatt catcgtcgat ttcaacgctt   1200
tcccgtgcaa acttattatt gcaagaaaaa attggttcgc aagaaaactc tgtcaaacaa   1260
gaaaactatt cgaaaaatcc tcaacttcgt catcaattaa cttccagaag tagatcattt   1320
attcatcatc cggcaaacga gtatttgaag aatacttttg gaaattcaca tagtaatgac   1380
atcggaaagg gagttgaagt gctatctttg acaccgagtt ttatggatat tcccgaaaaa   1440
gaaagagaaa cggaaagatc gccatcatcc aattacatta ctgacagacc tttcactcga   1500
aaacctagat cttctagcat tgacgtaaac cataggtatc cacctatggc accaacaacc   1560
gtagcgacat ctcccggtgc attgaacaat gccgtagcaa gcaatctcga cgatcaactg   1620
agtttaacat cactaaactc tcagccatca tcgatagcaa atatgatgat ggacccttca   1680
aacctagctg agcaaagttc tattcattca gttcctcagt caataaactc tccgagaatg   1740
cctaaaactg gaagtcgcca agacaagaac attcacacta agaaggaaga agaaatccg    1800 ctaaataaca tacgatctc gtcacaattg gaaaatgtac cagacgagat gaaccaaatg   1860
ttctccccac cattaaaaag tatgaataga ccggatgcca aagggaaaa ttcatctagt   1920 agtaatttca taatccaagg aaatagcatg atctctacgc cttccggaag gaatgacctt   1980
ccagatacct ctccaatgag tagtattcaa acagcgtcac caccaagtca attactgacc   2040
gatcaaggat ttgcggattt ggataatttc atgtcttcgt ta                      2082
```

<210> SEQ ID NO 22
<211> LENGTH: 694
<212> TYPE: PRT
<213> ORGANISM: Saccharomyces cerevisiae

<400> SEQUENCE: 22

```
Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
    50                  55                  60
```

```
Arg Leu Glu Lys Lys Lys Leu Ala Gln Lys Lys Glu Glu Ala Arg
 65                  70                  75                  80

Ala Lys Ala Lys Glu Lys Gln Arg Lys Gln Cys Thr Cys Gly Thr Asp
                 85                  90                  95

Glu Val Cys Lys Tyr His Ala Gln Lys Arg His Leu Arg Lys Ser Pro
                100                 105                 110

Ser Ser Ser Gln Lys Lys Gly Arg Ser Ile Ser Arg Ser Gln Pro Met
            115                 120                 125

Phe Glu Arg Val Leu Ser Ser Thr Ser Leu Asp Ser Asn Met Leu Ser
        130                 135                 140

Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
            180                 185                 190

Asp Gln Asn Phe Ser Ile Pro Gln Ser Pro Leu Ser Ser Met Ser
        195                 200                 205

Phe Asn Phe Leu Thr Gly Asn Ile Asn Glu Thr Asn Gln Asn His Ser
    210                 215                 220

Asn His Gln His Ser Lys Ser Gly Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
            260                 265                 270

Ile Ser Asn Ser Arg Val Gly Glu Val Ser Val Pro Leu Glu Glu Tyr
        275                 280                 285

Ile Pro Ser Asp Ile Asp Gly Val Gly Arg Val Thr Asp Lys Ser Ser
    290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
            340                 345                 350

Asn Gly Asn Gly Met Asn Asn Ser Asn Asn Asn Ile Asn Ser Asn
        355                 360                 365

Gly Asn Asp Lys Asn Asn Asn Ser Ser Arg Gln Glu His Gln Gly
    370                 375                 380

Asn Gly Leu Phe Asp Met Phe Thr Asp Ser Ser Ser Ile Ser Thr Leu
385                 390                 395                 400

Ser Arg Ala Asn Leu Leu Leu Gln Glu Lys Ile Gly Ser Gln Glu Asn
                405                 410                 415

Ser Val Lys Gln Glu Asn Tyr Ser Lys Asn Pro Gln Leu Arg His Gln
            420                 425                 430

Leu Thr Ser Arg Ser Arg Ser Phe Ile His His Pro Ala Asn Glu Tyr
        435                 440                 445

Leu Lys Asn Thr Phe Gly Ser His Ser Asn Asp Ile Gly Lys Gly
    450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Ser Asn Tyr Ile Thr Asp Arg
```

```
            485                 490                 495
Pro Phe Thr Arg Lys Pro Arg Ser Ser Ser Ile Asp Val Asn His Arg
            500                 505                 510

Tyr Pro Pro Met Ala Pro Thr Thr Val Ala Thr Ser Pro Gly Ala Leu
            515                 520                 525

Asn Asn Ala Val Ala Ser Asn Leu Asp Asp Gln Leu Ser Leu Thr Ser
            530                 535                 540

Leu Asn Ser Gln Pro Ser Ser Ile Ala Asn Met Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
            595                 600                 605

Gln Leu Glu Asn Val Pro Asp Glu Met Asn Gln Met Phe Ser Pro Pro
            610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
                645                 650                 655

Arg Asn Asp Leu Pro Asp Thr Ser Pro Met Ser Ser Ile Gln Thr Ala
            660                 665                 670

Ser Pro Pro Ser Gln Leu Leu Thr Asp Gln Gly Phe Ala Asp Leu Asp
            675                 680                 685

Asn Phe Met Ser Ser Leu
            690

<210> SEQ ID NO 23
<211> LENGTH: 2739
<212> TYPE: DNA
<213> ORGANISM: Aspergillus fumigatus

<400> SEQUENCE: 23
atgctcatcg atggcgagaa gtgggcttgt gaagcttgcg tccggggtca ccgagtcagc    60
agctgtcacc atagtggtaa gtgacacatt cctcgcagca aaggacatca ccgatcaggg   120
tggctgacat accttgccaa atatagaccg ccccttgacc cacatcaaca aaaaaggccg   180
tccagtctct caatgcgccc actgtcgcgg cttacgcaag tcacggacaa cccacaccag   240
gtgcgagtgt ggtgataaga agaagaatag ccacaaaaat gatttagatc ccaacgctgt   300
tgacaaacgg gatctcaagc gtgagcatgt tggcgatggc acattggttc agtatttctg   360
attaagattt tacagaggac tcccgtccaa aatgtggctg cactcatggt cagcgctgta   420
tctgcgcgct gaagaaggaa ccccatctag atactgttcc ggaaactggc ctgcctccgc   480
atccgcctgc agcaccgtcg gagcagccaa agaagccgca gttgacttca gccaagtcgg   540
aaagcacgct cactatcttc gcgatggtc accacaagcc ggctcacaag cataatgaca   600
tggcacacaa gtgtggtctg ccctacacaa tcccgcgctc ataccatc acactacgt    660 ccgatgttcc gcgccgatcg gttgaatttc tgcctttgac tgagcccacg tttctggaga   720
aggcctttac cagccaagtg cagtcggaaa cgcagtcgaa cggttcgcaa cagcgacttg   780
tcaattctga acatggatcg cccgatcatg gtccagctgc cgctacggaa gatattacca   840
cgacggtacc tccgctcgac atgtcttcct tcttccctca agctcagccg tctatgggcc   900
```

```
agtcttctgg cggcgcagcg gagtcaatat caacgcccct gggtcagatc cccttgaatc    960
cgcttgatcc tgtcatgacc agcatgccgc ctctcgatgt ctcgttcccc tcatttccga   1020
caacgactgc gacaacgtcg acatccccag tgacctccct ggcgctccaa gatccctaca   1080
aggagccttt cttcgcatcg cccgacagcg acctgccgct gaactccgct gcctttagcg   1140
cgcctccggt cgattggtcc aatttccctc tgtattcctc agatattccc actgcgacca   1200
gcacacaggc tccttcctac gcgagcttcg actacaattc gatggcgccc ggattcaccg   1260
ccccgtcctc gtctggtgac atctccgaag ctgaggattt tgggccgctg tcgggtctgg   1320
gaaatactag tggcgatctg catgatatgc acagtgccag cgatggttcg gatttcgatc   1380
atttccgtat cagctccgcc tcctcgttca ttggcctgcc gcaagctcag ctgttgtctt   1440
caaacaacct tgaggcgatc gacatcgacg agttcctcaa gtccgccaac gagtcgactg   1500
ccgccttgga acatcagcta caggccagca tgggggtaga acctaagccc gtccctgcgc   1560
aaaacacctt tgtcccttty actgatgcag acacctteaa gcctatgcct gattcgacga   1620
cgagcctgcc gatgacgacg tctcctgcgg agaccatgtg gcctactgcg atgtttgatt   1680
ccagtgctcc gtccatggat gacagtaatg gcaacttcta taccccgccc tgggtataaa   1740
attactagtg catcgtctgc tcggtattgt ctttccagct tccctcgatc tagttgcggc   1800
taccttctcc tccaccacct ccacaccgtc tgagtgacga cctccgccct catgaccttg   1860
atgagagatg atgtttattt cctaactatt tttgacattc attttgttcg attagcgcag   1920
ctccgaatcg tctgacgcta ccccagcatt tcagatctat atcaagattc ccgttcaatt   1980
ttcattttgc cttttactgt gcagtcgctg gctctgtata tcccaagacc actgcatcgg   2040
caatggtttg actttgtact catctacaga ccaggcagtc gtgatgcccc ctgtcatggt   2100
ggcttgctat tccgtgtcat tgcatctata gatatcctgc tccaccagtg tttggtggtt   2160
tcatgcagtc caaaagattc tggttatgca caatagattt gatcgtgatt tgatctgcgt   2220
ttagtacgat ccacaaaggt aaaggtacag tacctagttg catgtcacgt attgttctgt   2280
atgcgtcttc tgcatggacc aaggtagcca cctcgacgta caggagcaca gtgcccgccg   2340
gtatcctgcc acatcaagta gcggtgtgta ttccggagta ttatccacct accaacccag   2400
cgaccgatgg aatcgagaag tttattgtca atgtgagact agtaatgatg caattcgcaa   2460
atgattatgc agcttctgaa tactccgcgt gatgaaaagg gaagcgtacg aacactccta   2520
ccagtggagg gtctcgaaag ctaccgccgc agggatgacc cacggtggcc tttctccgta   2580
catattacag ggatacgcag cgcagtaacg caccaacaca ggtacgaatg gaatgcgctg   2640
caaggctggg gtgctcgcat ccaattccag ttccagttcc agttccagtt ccagtccagt   2700
ttcagcttca gcttcagctc agctagcctg ctccgctaa                         2739
```

<210> SEQ ID NO 24
<211> LENGTH: 667
<212> TYPE: PRT
<213> ORGANISM: Aspergillus fumigatus

<400> SEQUENCE: 24

```
Met Leu Ile Asp Gly Glu Lys Trp Ala Cys Glu Ala Cys Val Arg Gly
1               5                   10                  15

His Arg Val Ser Ser Cys His His Ser Asp Arg Pro Leu Thr His Ile
            20                  25                  30

Asn Lys Lys Gly Arg Pro Val Ser Gln Cys Ala His Cys Arg Gly Leu
        35                  40                  45
```

```
Arg Lys Ser Arg Thr Thr His Thr Arg Cys Glu Cys Gly Asp Lys Lys
    50                  55                  60
Lys Asn Ser His Lys Asn Asp Leu Asp Pro Asn Ala Val Asp Lys Arg
65                  70                  75                  80
Asp Leu Lys Gln Asp Ser Arg Pro Lys Cys Gly Cys Thr His Gly Gln
                85                  90                  95
Arg Cys Ile Cys Ala Leu Lys Lys Glu Pro His Leu Asp Thr Val Pro
            100                 105                 110
Glu Thr Gly Leu Pro Pro His Pro Ala Ala Pro Ser Glu Gln Pro
        115                 120                 125
Lys Lys Pro Gln Leu Thr Ser Ala Lys Ser Glu Ser Thr Leu Thr Ile
130                 135                 140
Phe Arg Asp Gly His His Lys Pro Ala His Lys His Asn Asp Met Ala
145                 150                 155                 160
His Lys Cys Gly Leu Pro Tyr Thr Ile Pro Arg Ser His Thr Ile His
            165                 170                 175
Thr Thr Ser Asp Val Pro Arg Arg Ser Val Glu Phe Leu Pro Leu Thr
            180                 185                 190
Glu Pro Thr Phe Leu Glu Lys Ala Phe Thr Ser Gln Val Gln Ser Glu
        195                 200                 205
Thr Gln Ser Asn Gly Ser Gln Gln Arg Leu Val Asn Ser Glu His Gly
    210                 215                 220
Ser Pro Asp His Gly Pro Ala Ala Thr Glu Asp Ile Thr Thr Thr
225                 230                 235                 240
Val Pro Pro Leu Asp Met Ser Ser Phe Phe Pro Gln Ala Gln Pro Ser
            245                 250                 255
Met Gly Gln Ser Ser Gly Gly Ala Ala Glu Ser Ile Ser Thr Pro Leu
        260                 265                 270
Gly Gln Ile Pro Leu Asn Pro Leu Asp Pro Val Met Thr Ser Met Pro
    275                 280                 285
Pro Leu Asp Val Ser Phe Pro Ser Phe Pro Thr Thr Thr Ala Thr Thr
        290                 295                 300
Ser Thr Ser Pro Val Thr Ser Leu Ala Leu Gln Asp Pro Tyr Lys Glu
305                 310                 315                 320
Pro Phe Phe Ala Ser Pro Asp Ser Asp Leu Pro Leu Asn Ser Ala Ala
            325                 330                 335
Phe Ser Ala Pro Pro Val Asp Trp Ser Asn Phe Pro Leu Tyr Ser Ser
        340                 345                 350
Asp Ile Pro Thr Ala Thr Ser Thr Gln Ala Pro Ser Tyr Ala Ser Phe
    355                 360                 365
Asp Tyr Asn Ser Met Ala Pro Gly Phe Thr Ala Pro Ser Ser Ser Gly
    370                 375                 380
Asp Ile Ser Glu Ala Glu Asp Phe Gly Pro Leu Ser Gly Leu Gly Asn
385                 390                 395                 400
Thr Ser Gly Asp Leu His Asp Met His Ser Ala Ser Asp Gly Ser Asp
            405                 410                 415
Phe Asp His Phe Arg Ile Ser Ser Ala Ser Ser Phe Ile Gly Leu Pro
        420                 425                 430
Gln Ala Gln Leu Leu Ser Ser Asn Asn Leu Glu Ala Ile Asp Ile Asp
    435                 440                 445
Glu Phe Leu Lys Ser Ala Asn Glu Ser Thr Ala Ala Leu Glu His Gln
450                 455                 460
Leu Gln Ala Ser Met Gly Val Glu Pro Lys Pro Val Pro Ala Gln Asn
```

```
              465                 470                 475                 480
          Thr Phe Val Pro Leu Thr Asp Ala Asp Thr Phe Lys Pro Met Pro Asp
                              485                 490                 495

Ser Thr Thr Ser Leu Pro Met Thr Thr Ser Pro Ala Glu Thr Met Trp
                          500                 505                 510

Pro Thr Ala Met Phe Asp Ser Ser Ala Pro Ser Met Asp Asp Ser Asn
                      515                 520                 525

Gly Asn Phe Tyr Thr Pro Pro Trp Val Ala Thr Ser Thr Tyr Arg Ser
                  530                 535                 540

Thr Val Pro Ala Gly Ile Leu Pro His Gln Val Ala Val Cys Ile Pro
          545                 550                 555                 560

Glu Tyr Tyr Pro Pro Thr Asn Pro Ala Thr Asp Gly Ile Glu Lys Phe
                              565                 570                 575

Ile Val Asn Leu Leu Asn Thr Pro Arg Asp Glu Lys Gly Ser Val Arg
                          580                 585                 590

Thr Leu Leu Pro Val Glu Gly Leu Glu Ser Tyr Arg Arg Arg Asp Asp
                      595                 600                 605

Pro Arg Trp Pro Phe Ser Val His Ile Thr Gly Ile Arg Ser Ala Val
                  610                 615                 620

Thr His Gln His Arg Tyr Glu Trp Asn Ala Leu Gln Gly Trp Gly Ala
          625                 630                 635                 640

Arg Ile Gln Phe Gln Phe Gln Phe Gln Phe Gln Phe Gln Ser Ser Phe
                              645                 650                 655

Ser Phe Ser Phe Ser Ser Ala Ser Leu Leu Arg
                          660                 665

<210> SEQ ID NO 25
<211> LENGTH: 36
<212> TYPE: DNA
<213> ORGANISM: Saccharomyces cerevisiae

<400> SEQUENCE: 25
caccggtgca tgcctgcagg agctcctagt tagaaa                                  36

<210> SEQ ID NO 26
<211> LENGTH: 36
<212> TYPE: DNA
<213> ORGANISM: Saccharomyces cerevisiae

<400> SEQUENCE: 26
aactattctt gaatggaatt ctagtcgatg acttct                                  36

<210> SEQ ID NO 27
<211> LENGTH: 918
<212> TYPE: DNA
<213> ORGANISM: Thermomyces lanuginosus

<400> SEQUENCE: 27
atgaggagct cccttgtgct gttctttgtc tctgcgtgga cggccttggc cagtccatt         60 cgtcgagagg tctcgcagga tctgtttaac cagttcaatc tctttgcaca gtattctgca       120
gccgcatact gcggaaaaaa caatgatgcc ccagctggta caaacattac gtgcacggga       180
aatgcctgcc ccgaggtaga aaggcggat gcaacgtttc tctactcgtt tgaagactct       240
ggagtgggcg atgtcaccgg cttccttgct ctcgacaaca cgaacaaatt gatcgtcctc       300
tctttccgtg gctctcgttc catagagaac tggatcggga tcttaacttc gacttgaaa       360 gaaataaatg acatttgctc cggctgcagg ggacatgacg gcttcacttc gtcctggagg       420
```

-continued

```
tctgtagccg atacgttaag gcagaaggtg gaggatgctg tgagggagca tcccgactat    480
cgcgtggtgt ttaccggaca tagcttgggt ggtgcattgg caactgttgc cggagcagac    540
ctgcgtggaa atgggtatga tatcgacgtg ttttcatatg gcgcccccg agtcggaaac     600 agggcttttg cagaattcct gaccgtacag accggcggaa cactctaccg cattacccac    660
accaatgata ttgtccctag actcccgccg cgcgaattcg gttacagcca ttctagccca    720
gagtactgga tcaaatctgg aaccttgtc cccgtcaccc gaaacgatat cgtgaagata     780
gaaggcatcg atgccaccgg cggcaataac cagcctaaca ttccggatat ccctgcgcac    840
ctatggtact tcgggttaat tgggacatgt ctttagtggc cggcgcggct gggtccgact    900
ctagcgagct cgagatct                                                   918
```

```
<210> SEQ ID NO 28
<211> LENGTH: 291
<212> TYPE: PRT
<213> ORGANISM: Thermomyces lanuginosus

<400> SEQUENCE: 28

Met Arg Ser Ser Leu Val Leu Phe Phe Val Ser Ala Trp Thr Ala Leu
1               5                   10                  15

Ala Ser Pro Ile Arg Arg Glu Val Ser Gln Asp Leu Phe Asn Gln Phe
            20                  25                  30

Asn Leu Phe Ala Gln Tyr Ser Ala Ala Ala Tyr Cys Gly Lys Asn Asn
        35                  40                  45

Asp Ala Pro Ala Gly Thr Asn Ile Thr Cys Thr Gly Asn Ala Cys Pro
    50                  55                  60

Glu Val Glu Lys Ala Asp Ala Thr Phe Leu Tyr Ser Phe Glu Asp Ser
65                  70                  75                  80

Gly Val Gly Asp Val Thr Gly Phe Leu Ala Leu Asp Asn Thr Asn Lys
                85                  90                  95

Leu Ile Val Leu Ser Phe Arg Gly Ser Arg Ser Ile Glu Asn Trp Ile
            100                 105                 110

Gly Asn Leu Asn Phe Asp Leu Lys Glu Ile Asn Asp Ile Cys Ser Gly
        115                 120                 125

Cys Arg Gly His Asp Gly Phe Thr Ser Ser Trp Arg Ser Val Ala Asp
    130                 135                 140

Thr Leu Arg Gln Lys Val Glu Asp Ala Val Arg Glu His Pro Asp Tyr
145                 150                 155                 160

Arg Val Val Phe Thr Gly His Ser Leu Gly Gly Ala Leu Ala Thr Val
                165                 170                 175

Ala Gly Ala Asp Leu Arg Gly Asn Gly Tyr Asp Ile Asp Val Phe Ser
            180                 185                 190

Tyr Gly Ala Pro Arg Val Gly Asn Arg Ala Phe Ala Glu Phe Leu Thr
        195                 200                 205

Val Gln Thr Gly Gly Thr Leu Tyr Arg Ile Thr His Thr Asn Asp Ile
    210                 215                 220

Val Pro Arg Leu Pro Pro Arg Glu Phe Gly Tyr Ser His Ser Ser Pro
225                 230                 235                 240

Glu Tyr Trp Ile Lys Ser Gly Thr Leu Val Pro Val Thr Arg Asn Asp
                245                 250                 255

Ile Val Lys Ile Glu Gly Ile Asp Ala Thr Gly Gly Asn Asn Gln Pro
            260                 265                 270

Asn Ile Pro Asp Ile Pro Ala His Leu Trp Tyr Phe Gly Leu Ile Gly
```

Thr Cys Leu
290

<210> SEQ ID NO 29
<211> LENGTH: 26
<212> TYPE: DNA
<213> ORGANISM: Saccharomyces cerevisiae

<400> SEQUENCE: 29
tctagagggc cgcatcatgt aattag                                    26

<210> SEQ ID NO 30
<211> LENGTH: 30
<212> TYPE: DNA
<213> ORGANISM: Saccharomyces cerevisiae

<400> SEQUENCE: 30
gacgccatgg tgaagctttc ttttaatcgt                                30

<210> SEQ ID NO 31
<211> LENGTH: 95
<212> TYPE: DNA
<213> ORGANISM: Thermomyces lanuginosus

<400> SEQUENCE: 31
caagaagatt acaaactatc aatttcatac acaatataaa cgattaaaag aaagcttcac    60
catgaggagc tcccttgtgc tgttctttgt ctctg                              95

<210> SEQ ID NO 32
<211> LENGTH: 87
<212> TYPE: DNA
<213> ORGANISM: Thermomyces lanuginosus

<400> SEQUENCE: 32
gagggcgtga atgtaagcgt gacataacta attacatgat gcggccctct agattatcaa    60
agacatgtcc caattaaccc gaagtac                                       87

<210> SEQ ID NO 33
<211> LENGTH: 873
<212> TYPE: DNA
<213> ORGANISM: Thermomyces lanuginosus

<400> SEQUENCE: 33
atgaggagct cccttgtgct gttctttgtc tctgcgtgga cggccttggc cagtcctatt    60
cgtcgagagg tctcgcagga tctgtttaac cagttcaatc tctttgcaca gtattctgca   120
gccgcatact gcgaaaaaaa caatgatgcc ccagctggta caaacattac gtgcacggga   180
aatgcctgcc ccgaggtaga aaggcggat gcaacgtttc tctactcgtt tgaagactct    240
ggagtgggcg atgtcaccgg cttccttgct ctcgacaaca cgaacaaatt gatcgtcctc   300
tctttccgtg gctctcgttc catagagaac tggatcggga atcttaactt cgacttgaaa   360
gaaataaatg acatttgctc cggctgcagg ggacatgacg gcttcacttc gtcctggagg   420
tctgtagccg atacgttaag gcagaaggtg gaggatgctg tgagggagca tcccgactat   480
cgcgtggtgt ttaccggaca tagcttgggt ggtgcattgg caactgttgc cggagcagac   540
ctgcgtggaa atgggtatga tatcgacgtg ttttcatatg gcgcccccg agtcggaaac    600 agggcttttg cagaattcct gaccgtacag accggcggaa cactctaccg cattacccac   660

```
accaatgata ttgtccctag actcccgccg cgcgaattcg gttacagcca ttctagccca    720
gaatactgga tcaaatctgg aaccttgtc cccgtccggc gacgagacat cgtgaagata     780
gaaggcatcg atgccaccgg cggcaataac cagcctaaca ttccggatat ccctgcgcac    840
ctatggtact tcgggttaat tgggacatgt ctt                                 873
```

<210> SEQ ID NO 34
<211> LENGTH: 291
<212> TYPE: PRT
<213> ORGANISM: Thermomyces lanuginosus

<400> SEQUENCE: 34

```
Met Arg Ser Ser Leu Val Leu Phe Phe Val Ser Ala Trp Thr Ala Leu
1               5                   10                  15

Ala Ser Pro Ile Arg Arg Glu Val Ser Gln Asp Leu Phe Asn Gln Phe
            20                  25                  30

Asn Leu Phe Ala Gln Tyr Ser Ala Ala Tyr Cys Gly Lys Asn Asn
        35                  40                  45

Asp Ala Pro Ala Gly Thr Asn Ile Thr Cys Thr Gly Asn Ala Cys Pro
    50                  55                  60

Glu Val Glu Lys Ala Asp Ala Thr Phe Leu Tyr Ser Phe Glu Asp Ser
65                  70                  75                  80

Gly Val Gly Asp Val Thr Gly Phe Leu Ala Leu Asp Asn Thr Asn Lys
                85                  90                  95

Leu Ile Val Leu Ser Phe Arg Gly Ser Arg Ser Ile Glu Asn Trp Ile
            100                 105                 110

Gly Asn Leu Asn Phe Asp Leu Lys Glu Ile Asn Asp Ile Cys Ser Gly
        115                 120                 125

Cys Arg Gly His Asp Gly Phe Thr Ser Ser Trp Arg Ser Val Ala Asp
    130                 135                 140

Thr Leu Arg Gln Lys Val Glu Asp Ala Val Arg Glu His Pro Asp Tyr
145                 150                 155                 160

Arg Val Val Phe Thr Gly His Ser Leu Gly Gly Ala Leu Ala Thr Val
                165                 170                 175

Ala Gly Ala Asp Leu Arg Gly Asn Gly Tyr Asp Ile Asp Val Phe Ser
            180                 185                 190

Tyr Gly Ala Pro Arg Val Gly Asn Arg Ala Phe Ala Glu Phe Leu Thr
        195                 200                 205

Val Gln Thr Gly Gly Thr Leu Tyr Arg Ile Thr His Thr Asn Asp Ile
    210                 215                 220

Val Pro Arg Leu Pro Pro Arg Glu Phe Gly Tyr Ser His Ser Ser Pro
225                 230                 235                 240

Glu Tyr Trp Ile Lys Ser Gly Thr Leu Val Pro Val Arg Arg Arg Asp
                245                 250                 255

Ile Val Lys Ile Glu Gly Ile Asp Ala Thr Gly Gly Asn Asn Gln Pro
            260                 265                 270

Asn Ile Pro Asp Ile Pro Ala His Leu Trp Tyr Phe Gly Leu Ile Gly
        275                 280                 285

Thr Cys Leu
    290
```

<210> SEQ ID NO 35
<211> LENGTH: 95
<212> TYPE: DNA
<213> ORGANISM: Thermomyces lanuginosus

<400> SEQUENCE: 35
caagaagatt acaaactatc aatttcatac acaatataaa cgattaaaag aaagcttcac    60
catgaggagc tcccttgtgc tgttctttgt ctctg    95

<210> SEQ ID NO 36
<211> LENGTH: 87
<212> TYPE: DNA
<213> ORGANISM: Thermomyces lanuginosus

<400> SEQUENCE: 36
gagggcgtga atgtaagcgt gacataacta attacatgat gcggccctct agattatcaa    60
agacatgtcc caattaaccc gaagtac    87

<210> SEQ ID NO 37
<211> LENGTH: 46
<212> TYPE: DNA
<213> ORGANISM: Thermomyces lanuginosus

<400> SEQUENCE: 37
ctctgcgtgg acggccttgg ccgaggtctc gcaggatctg tttaac    46

<210> SEQ ID NO 38
<211> LENGTH: 45
<212> TYPE: DNA
<213> ORGANISM: Thermomyces lanuginosus

<400> SEQUENCE: 38
ttaaacagat cctgcgagac ctcggccaag gccgtccacg cagag    45

<210> SEQ ID NO 39
<211> LENGTH: 26
<212> TYPE: DNA
<213> ORGANISM: Thermomyces lanuginosus

<400> SEQUENCE: 39
ctaggaaccc atcaggttgg tggaag    26

<210> SEQ ID NO 40
<211> LENGTH: 114
<212> TYPE: DNA
<213> ORGANISM: Thermomyces lanuginosus
<220> FEATURE:
<221> NAME/KEY: misc_feature
<222> LOCATION: (40)..(93)
<223> OTHER INFORMATION: N = A, C, G, OR T

<400> SEQUENCE: 40
ctgtgcaaag agattgaact ggttaaacag atcctgcgan nnnnnnnnn nnnnnnnnnn    60 nnnnnnnnnn nnnnnnnnnn nnnnnnnnnn nnncatggtg aagctttctt ttaa    114

<210> SEQ ID NO 41
<211> LENGTH: 51
<212> TYPE: DNA
<213> ORGANISM: Thermomyces lanuginosus

<400> SEQUENCE: 41
atgaagagct cccttgtgct gttctttgtc tctgcgtgga cggccttggc c    51

<210> SEQ ID NO 42
<211> LENGTH: 25
<212> TYPE: DNA
<213> ORGANISM: Saccharomyces cerevisiae

```
<400> SEQUENCE: 42
ccggtgcatg cctgcaggag ctcct                                              25

<210> SEQ ID NO 43
<211> LENGTH: 27
<212> TYPE: DNA
<213> ORGANISM: Saccharomyces cerevisiae

<400> SEQUENCE: 43
accggtcttt tttgctggaa cggttca                                            27

<210> SEQ ID NO 44
<211> LENGTH: 25
<212> TYPE: DNA
<213> ORGANISM: Saccharomyces cerevisiae

<400> SEQUENCE: 44
tcatgatacg atcgtgaaag aatat                                              25

<210> SEQ ID NO 45
<211> LENGTH: 25
<212> TYPE: DNA
<213> ORGANISM: Saccharomyces cerevisiae

<400> SEQUENCE: 45
tcatgaggat gatgacaaag aagac                                              25

<210> SEQ ID NO 46
<211> LENGTH: 34
<212> TYPE: DNA
<213> ORGANISM: Saccharomyces cerevisiae

<400> SEQUENCE: 46
tcttttgctg gcatttcttc tagaagcaaa aaga                                    34

<210> SEQ ID NO 47
<211> LENGTH: 32
<212> TYPE: DNA
<213> ORGANISM: Saccharomyces cerevisiae

<400> SEQUENCE: 47
tcttttccgc tgaaccgttc cagcaaaaaa ga                                      32

<210> SEQ ID NO 48
<211> LENGTH: 52
<212> TYPE: PRT
<213> ORGANISM: Candida glabrata

<400> SEQUENCE: 48

Met Pro Glu Gln Val Asn Cys Gln Tyr Asp Cys His Cys Ser Asn Cys
1               5                   10                  15

Ala Cys Glu Asn Thr Cys Asn Cys Cys Ala Lys Pro Ala Cys Ala Cys
            20                  25                  30

Thr Asn Ser Ala Ser Asn Glu Cys Ser Cys Gln Thr Cys Lys Cys Gln
        35                  40                  45

Thr Cys Lys Cys
    50
```